(12) United States Patent
Daniell

(10) Patent No.: US 7,803,991 B2
(45) Date of Patent: *Sep. 28, 2010

(54) UNIVERSAL CHLOROPLAST INTEGRATION AND EXPRESSION VECTORS, TRANSFORMED PLANTS AND PRODUCTS THEREOF

(75) Inventor: Henry Daniell, Winter Park, FL (US)

(73) Assignee: Auburn University, Auburn, AL (US)

( * ) Notice: Subject to any disclaimer, the term of this patent is extended or adjusted under 35 U.S.C. 154(b) by 654 days.

This patent is subject to a terminal disclaimer.

(21) Appl. No.: 11/379,833

(22) Filed: Apr. 24, 2006

(65) Prior Publication Data

US 2008/0189803 A1 Aug. 7, 2008

Related U.S. Application Data

(63) Continuation of application No. 09/079,640, filed on May 15, 1998, now Pat. No. 7,129,391.

(60) Provisional application No. 60/079,042, filed on Mar. 23, 1998, provisional application No. 60/055,314, filed on Aug. 7, 1997.

(51) Int. Cl.
 C12N 15/82 (2006.01)
 A01H 5/00 (2006.01)
 C12N 15/52 (2006.01)
 C12N 15/54 (2006.01)

(52) U.S. Cl. .................. 800/300; 800/278; 800/282; 800/300.1; 800/317.3; 435/463

(58) Field of Classification Search .................. None
 See application file for complete search history.

(56) References Cited

U.S. PATENT DOCUMENTS

| 5,545,817 A | 8/1996 | McBride et al. |
| 5,550,038 A | 8/1996 | Goodman et al. |
| 5,693,507 A | 12/1997 | Daniell et al. |
| 5,932,479 A | 8/1999 | Daniell et al. |

FOREIGN PATENT DOCUMENTS

| EP | 251654 | 1/1998 |
| WO | WO9102066 | 2/1991 |

OTHER PUBLICATIONS

Stable Cholorplast Transformation Using a Universal Integration Vector, Chittibabu Guda et al. Mar. 1997 *Botany & Micro* No. 705.
Correct Splicing of a Group II intron from a chimeric reporter gene transcript in tobacco plastids, Bock et al. *Nucleic Acids Research* 1995, vol. 23, No. 13.
Integration of foreign sequences into the tobacco plastome via ployethylene glycol-mediated protoplast transformation, Koop et al. *Planta* 1996 199: 193-201.
Containment of herbicide resistance through genetic engineering of the chloroplast genome, Daniell et al. *Nature Biotechnology* vol. 18 Apr. 1998 pp. 345-348.
Marker free transgenic plants: engineering the chloroplast genome without the use of antibiotic selection, *Curr Genet* (2001) 39: 109-116.
Expression of the Native Cholera Toxin *B* Subunit Gene and Assembly as Functional Oligomers in Transgenic Tobacco Chloroplasts, Daniell et al. *J. Mol. Biol* (2001) 311, 1001-1009.
Overexpression of the *Bt cry*2Aa2 operon in chloroplasts leads to formation of insecticidal crystals, Cosa et al., *Nature Biotechnology* vol. 19 Jan. 2001 pp. 71-74.
Expression of an antimicrobial Peptide via the Chloroplast Genome to Control Phytopathogenic Bacteria and Fungi, DeGray et al., *Plant Physiology*, Nov. 2001, vol. 127, pp. 852-862.
Enhanced translation of a chloroplast-expressed R*bc*S gene restores small subunit levels and photosynthesis in nuclear R*bc*S antisense plants, Dhingra et al. *PNAS* Apr. 20, 2004, vol. 101, No. 16, 6315-6320.
In vivo analysis of plastid *psb*A, *rbc*1 , and *rp*132 UTR element by chloroplast transformation: tobacco plastid gene expression is controlled by modulation of transcript levels and translation efficiency, Eibl et al. Plant Journal (1999) 19(3) 333-345.
The stem-loop region of the tobacco *psbA* 5'UTR is an important determinant of mRNA stability and translation efficiency, Zou et al., *Mol. Gen Genocmics* (2003) 269: 340-349.
Chloroplast transformation in oilseed rape, Bing-Kai Hou et al., *Transgenic Research* 12: 111-114, 2003.
Efficient plastid transformation in tobacco using the *aphA-6* gene and kanamycin selection, F.-C. Huang et al., *Mol Genet Genomics* (2002) 268: 19-27.
Dicistronic expression of the green fluorescent protein and antibiotic resistance genes in the plastid for selection and tracking of plastid-transformed cells in tobacco, S.-W. Jeong et al. *Plant Cell Rep.* (2004) 22: 747-751.
Expression of the *B* subunit of *E. coli* heat-labile enterotoxin in the chloroplasts of plants and its characterization, Kang et al., *Transgenic Research* 12: 683-691, 2003.

(Continued)

Primary Examiner—David T Fox
(74) Attorney, Agent, or Firm—Timothy H. Van Dyke; Beusse Wolter Sanks Mora & Maire

(57) ABSTRACT

The invention provides universal chloroplast integration and expression vectors which are competent to stably transform and integrate genes of interest into chloroplast genome of multiple species of plants. Transformed plants and their progeny are provided. Monocotyledonous and dicotyledonous plants are transformed which have never been transformed heretofore. Plants transformed with a synthetic gene express valuable biodegradable protein-based polymers (PBPs). Transformed plants produce high value molecules. Resistance is provided to agricultural crops against the major classes of chemical herbicides. Herbicide resistance is used as a lethal selectable marker for chloroplast transformation. The transformed plants are capable of expressing in addition to the targeted trait, a desirable, secondary non-targeted trait. Insect resistance is provided to transformed plants, both against insects that are susceptible to Bt toxins and against insects that have developed resistance to Bt toxins.

29 Claims, 35 Drawing Sheets

OTHER PUBLICATIONS

Rapid and proven production of transplastomic tobacco plants by restoration of pigmentation and photosynthesis, Klaus et al., *The Plant Journal* (2003) 35, 811-821.

Overexpression of the *Bacillus thuringiensis* (Bt) Cyr2Aa2 protein in chloroplasts confers resistance to plants against susceptible and Bt-resistant insects, Kota et al., *Proc. Natl. Acad. Sci, USA* vol. 96, pp. 1840-1845 Mar. 1999.
Accumulation of trehalose within transgenic chloroplasts confers drought tolerance, Lee et al., *Molecular Breeding* 11: 1-13, 2003.
Phytoremediation of Organomercurial Compounds via Chloroplast Genetic Engineering, Ruiz et al., *Plant Physiology*, Jul. 2003, vol. 132, pp. 1-9.
Plastid Transformation in *Arabidopsis thaliana*, S. R. Sikdar et al., *Plant Cell Reports* (1998) 18: 20-24.
Engineering of the *rp123* gene cluster to replace the plastid RNA polymerase x subunit with the *Escherichia coli* homologue, J. Y. Suzuki et al., *Curr. Genet* (2000) 38: 218-225.
Analysis of Barley chloroplast *psbD* light-responsive promoter elements in transplastomic tobacco, Thum et al., Plant Molecular Biology 47: 353-366, 2001.
Expression of a chimeric uid*A* gene indicates that polycistonic mRNAs are efficiently translated in tobacco plastids, Staub et al., *The Plant Journal* (1995) 7(6), 845-848.
Kumar, S., Dhingra, A. and Daniell, H. (2004) Plastid expressed betaine aldehyde dehydrogenase gene in carrot cultured cells, roots and leaves confers enhanced salt tolerance. *Plant Physiol*. 136: 2843-2854.
Ruiz, O.N., Hussein, H., Terry, N., Daniell, H. (2003) Phytoremediation of organomercurial compounds via chloroplast genetic engineering. *Plant Physiol*. 132: 1-9.1344-1352.
Watson, J., Koya V., Leppla S. and Daniell, H. (2004) Expression of *Bacillus anthracis* protective antigen in transgenic chloroplasts of tobacco, a non-food/feed crop. *Vaccine* 22, 4374-4384.
Fernandez-San Millan, A., Mingo-Castel, A. and Daniell, H. (2003) A chloroplast transgenic approach to hyper-express and purify human serum albumin, a protein highly susceptible to proteolytic degradation. *Plant Biotechnol. J*. 1,71-79.
Daniell, H., Carmona-Sanchez, O., and Burns, B. B. (2004) Chloroplast derived antibodies, biopharmaceuticals and edible vaccines. In R. Fischer & S. Schillberg (Eds.) *Molecular Farming* pp. 113-133. Weinheim: WILEY-VCH Verlag.
Sidorov, V.A., Kasten, D., Pang, S.Z., Hajdukiewicz, P.T.J., Staub, J.M., Nehra, N.S. (1999) Stable chloroplast transformation in potato: use of green fluorescent protein as a plastid marker. *Plant J*. 19, 209-216.
Ruf, S., Hermann, M., Berger, I. J., Carrer, H. and Bock, R. (2001) Stable genetic transformation of tomato plastids and expression of a foreign protein in fruit. *Nat. Biotechnol*. 19, 870-875.
Kumar, S., Dhingra, A. and Daniell, H. (2004) Stable transformation of the cotton plastid genome and maternal inheritance of transgenes. *Plant Mol. Biol*.56, 203-216.
Dufourmantel, N., Pelissier, B., Garcon, F., Peltier, J.M. and Tissot. G. (2004). Generation of Fertile Transplastomic soybean. Plant Mol Biol. 55: 727-741.
Guda, C., Lee, S. B. and Daniell, H. (2000) Stable expression of biodegradable protein based polymer in tobacco chloroplasts. *Plant Cell Rep*. 19, 257-262.
Muhlbauer, S. K., Lossl, A., Tzekova, L., Zou, Z. R. and Koop, H. U. (2002) Functional analysis of plastid DNA replication origins in tobacco by targeted inactivation. *Plant J*. 32, 175-184.
Jeong, S. W., Jeong, W. J., Woo, J. W., Choi, D. W., Park, Y. I. and Liu, J. R. (2004) Dicistronic expression of the green fluorescent protein and antibiotic resistance genes in the plastid for selection and tracking of plastid-transformed cells in tobacco. *Plant Cell Rep*. 22, 747-751.
Svab, Z. and Maliga, P. (1993) High frequency plastid transformation in tobacco by selection for a chimeric aadA gene. Proc. Natl. Acad. Sci. USA 90: 913-917.
Viitanen, P. V., Devine, A. L., Khan, M. S., Deuel, D. L., Dyk, D. E. V. & Daniell, H. (2005). Metabolic engineering of the chloroplast genome using the *E. coli ubi*C gene reveals that chorismate is a readily abundant plant precursor for p-Hydroxybenzoic acid biosynthesis. *Plant Physiol*. in press.
Zoubenko, O. V., Allison, L. A., Svab, Z. and Maliga, P. (1994) Efficient targeting of foreign genes into the tobacco plastid genome. *Nuc. Acids Res*. 22, 3819-3824.
Staub, J. M. and Maliga, P. (1993) Accumulation of D1 Polypeptide in tobacco plastids is regulated via the untranslated region of the *psb*A messenger RNA. *EMBO J*. 12, 601-606.
Maier et al. J. Mol. Biol. 251: 614-628, 1995.
Daniell et al. "Chloroplast Genetic Engineering to Improve Agronomic Traits." Manuscript submitted 2003.
Jeffrey M. Staub and Pal Maliga: Expression of a chimeric *uid*A gene indicates that polycistronic mRNAs are efficiently translated in tobacco plastics; *The Plant Journal* (1995) 7(5), 845-848.
Tony A. Kavanagh et al. Homeologous Plastid DNA Ttransformation in Tobacco is Mediated by Multiiple Recombination Events. Genetics 152: 1111-1122 (Jul. 1999).
Datta T. et al. Transformation of the tobacco chloroplast genome with the *aro*A gene to confer glyphosate; Plant Physiology. Supplement vol. 111, No. 2 Jun. 1996 p. 1681.
Gordon-Kamm et al. Plant Cell 2:603-618. Jul. 1990.
Chasan, R. Plant Cell 4(1):1-2.
Bonnard et al. Curr. Genet. 9(5):417-422 1985.
Massenet et al. Plant Mol. Biol 10(1): 53-63 1987.
Lanversin et al. Theor. Appl. Genet. 76(3): 443-448 1988.
McBride et al. Amplification of a Chimeric Bacillus gene in chloroplasts leads to an extraordinary level of an insecticidal protein in tobacco, Biotechnology, vol. 13, Apr. 13, 1995, pp. 362-365.
Lu, Z. et al. Characterization of replication origins flanking the 23S rRNA gene in tobacco chloroplast DNA: Plant Molecular Biology, vol. 32, 1996, pp. 693-706.
Daniell et al. "Containment of herbicide resistance through genetic engineering of the chloroplast genome" (Apr. 1998) Nature Biotechnology 16, 345-348.
PhD thesis "Stable Expression of Foreign Genes in Chloroplasts," Chittibabu Guda, Mar. 21, 1997.
Hornung et al. "Sequence Variation in the putative replication origins of the five genetically distinct basic *Euoenothera* plastid chromosome (plastomes)"(1996) Mol. Gen Genet. 25: 609-612.
Sugita and Sugiura Regulation of gene expression in chloroplasts of higher plants (1996) Plant molecular Biology 32: 315-326.
Della-Ciopps et al. "Targeting a Herbicide Resistant Enzyme From *Escherichia coli* to Chloroplasts of Higher Plants" (1987) Bio/Technology 5: 579-584.
Penaloza-Vazques et al., "Expression of the hygromycin B phosphotransferase gene confers tolerance to the herbicide glyphosate," Plant Cell Reports, vol. 14, No. 8, May 1995, pp. 492-487 (abstract).

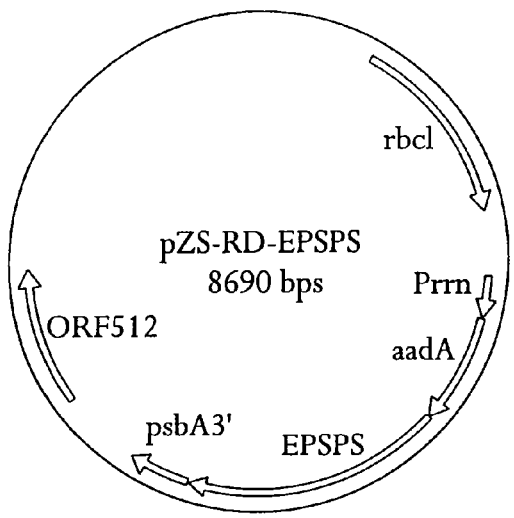# 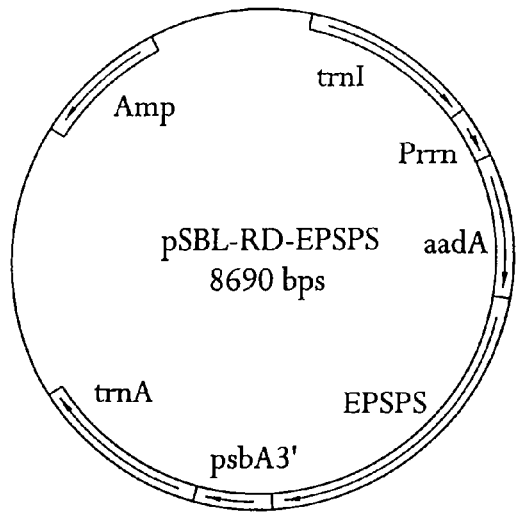
FIG. 2A  FIG. 2B
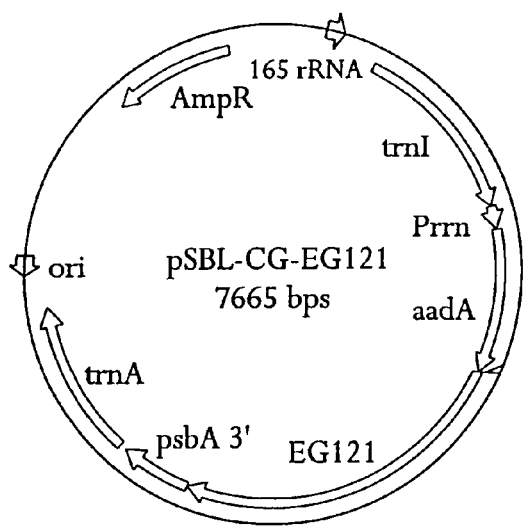 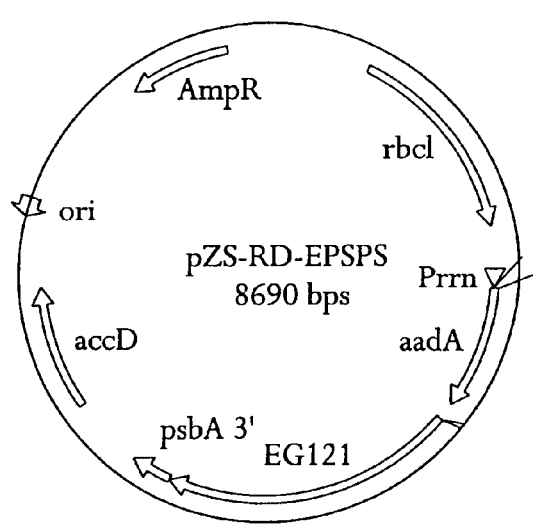
FIG. 3A  FIG. 3B

Sequence alignment of 16S-23S rDNA spacer region from several crop species

```
        ************************ * ****** *** ******* **** ***************  ***** * *********
     S  GTACACACGGCCCGTCACACTATGGAGCTGGCCATGCC-GAAGTCGTTACC-TTAACCGCAAG-AGGGGGATGCCGAAGGCAGGCTAGTGACTGGAGT
     T  GTACACACCGCCCGTCACACTATGGAGCTGGCCATGCCGAAGTCGTTACC-TTAACCGCGAAGTCGTTACC-TTAACCGCAAGGAGGGGGATGCCGAAGGCAGGCTAGTGACTGGAGT
     M  GTACACACCGCCCGTCACACTATAGAGCTGGCCATGCCGAAGTCGTTACC-TTAACCGCGAAGTCGTTACC-TTAACCGCAAGGAGGGGGATGCCGAAGGCTAGGCTTGCGACTGGAGT
1

******************************************************** *   ******  *** *******************
     S  GAAGTCGTAACAAGGTAGCCGTACTGGAAGGTGCGGCTGGATCACCCTCCTTTCAGGGAGAGCTAATGCTTGT------TGGGTAGTTTAGTTTGACACTGCTTCA
     T  GAAGTCGTAACAAGGTAGCCGTACTGGAAGGTGCGGCTGGATCACCCTCCTTTCAGGGAGAGCTAATGCTTGT------TGGGTATTTTGGTTTGACACTGCTTCA
     M  GAAGTCGTAACAAGGTAGCCGTACTGGAAGGTGCGGCTGGATCACCCTCCTTTCAGGGAGAGCTAAGTCTTATGCTTATTGGTATTTGGTATTTTGACACTGCTTCA
101

* ***   ****** ** ** ******** ****  *** ****** ****************** * ************
     S  CACCC-----AAAAAGAAGCGAGTTATGTCTGAGTCAAATTGGAGATGGAAGTCTTCTTCGTTTCTCGATGGTGAAGTAAGACTAAACTCATGAGCTTA
     T  CACCCCCAAAAAGAAGAGAAAGGGAGCTACGTCTGAGTTCAAACTGTAAACTTGGAGATGGATGGAAGTCTTCTTCTCCTCTCGACGGTGAAGTAAGACCA-GCTCATGAGCTTA
     M  CGCCC-----AAAAAGAAGCAGCTACGTCTGAGCTCAAACTTGGATATGGAATGGAAGTCTCTTTTCGTTT----AGGGTGAAGTAAGACCAAGCTCATGAGCTTA
201

************************ ** ******  ****** ******    ******** ** ***
     S  TTATCCTAGGTCGGAACAAGTT-------GATAGGAGCTACTTTTCA-CCCCCAT-------27bp-------ATGGGGTGAAAAAGGAAAAAGGAAAGAGAAGAGGATGGG
     T  TTATCCTAGGTCGGAACAAGTT---------GATAGGACCCCCTTTTTACGTCCCATGTCCCCCGTGTGGCACATGGGC-GAAAAAGGAAGGAAAGAGAAGAGGATGGG
     M  TTATCCTAGGTCGGAACAAATTAGTTGATAGTGATAGGAATAGGAATCCCCTTTTGACGTCCCATGT-CCCCCGTCGTGTGGCCATGGGCATGGGATGTCAAAAGGAAAGGAAAGGGATGGA----

**** *** *********** *********  ******  ********************************* ************
     S  GTTTCTTGCTTTGGCATAGGGCCCGGC-GGGAGGCCCGCACGACGGGCTATTAGCTCAGTGGTAGAGCGCCCCCTGATAATTGCGTCGTTGTG
     T  GTTTCTCTGCTTTTGGCATAGGGCCCCCCAGTGGGAGGCTCGCACGACGGGCTATTAGCTCAGTGGTAGAGCGCTATTAGCTCAGTGGTAGAGCGCCCCCCTGATAATTGCGTCGTTGTG
     M  GTTTTTCGCTTTTGGCGTAGCGGCCTCCCTTTGGGAGGC-CGGCGACGGGCCTCCCTTTGGGAGGC-CGGCGACGGGCTATTAGCTCAGTGGTAGAGCGCTATTAGCTCAGTGGTAGAGCGCCCCTGATAATT-CGTCGTTGTG
401
```

```
      ** ******** * ********************     ***** * ** *** ***** ******************  *****
    S TCCTTTTCTCTCATCGGAGTTATTCCCAAAGACTACTGCCATGGTAAAGAAGA-AGGG-GGAACAAGCAGCACACTTGGAGAGGCCAGTACAACGGATAGTTG
1001 T TCTTTTTCTCTCATCGGAGTTATTCACAAAGACTACTGCCAGGGTAAGGAAGA-AGGGGGGAACAAGCAGCACACTTGGAGAGGCCAGTACAACGGAGAGTTG
    M TCTTTTTCTGCCATCGGAGTTATTCCCAAGGACTACTGCCGTGGTAAGGAAGAAGGGGGGAAGAGCAGCACACTTGAAGAGGCCAGTACAACGGGGAGTTG

**************** ***************************  ***** ************* **** ********************
    S TATGCTGCGTTCGGGAAGGATGAATCGCTCCCGAAAAGAATCTATTGATTCTCTCCCAATTGGTTGGACCGTAGGTGGATGATTACTTCACGGGCGA
1101 T TATGCTGCGTTCGGGAAGGATGAATCGCTCCCGAAAAGAATCTATTGATTCTCTCCCAATTGGTTGCCGTAGGTGCGATGATTACTTCACGGCGA
    M TATGCTGCGTTCGGGAAGGATGGATCGCTCCCGAAAAGGAGTCTATTGATTCTCTCCCAATTGGTTGGATCGTAGGGCGATGATTACTTCACGGGCGA

↓ site of foreign gene insertion
      ********************* ********** * ***** ***************** *** ******************* ***
    S GGTCTCGGTCAAGTCCAAGATGGCCCAGTCGCCAGTGCGTCAAGGAAAGATAGAAAACTGACTCTTCATGCATGCTCCACTTGGCTCGGGGGG-ATA
1201 T GGTCTCGGTCAAGTCCAGATGCCCAGTGCCCAGTGCGCTGCAGGAAAGAATAGAAGAACATCATGCATGCTCCACTCATCATGCTCCACTTGGCTCGGGGGG-ATA
    M GGTCTCGGTCAAGTCCAGGATGCCCAGTCGCG-CAGGGAAAGATAGAAGAATAGAAGAACATCGACTCTTTCATGCATACTCCACTTGGCTCGGGGGATA

****************** *******     ***** *********************** ** ******************
    S TAGCTCAGTTGGTAGAGCTCCGCTTGCAATTGGGTCGTTGCGATTACGGGGTTGGATGTCTAAGGCGGTAATGTCTAGGCGGTAATGATAGTATCTGTACCTGAA
1301 T TAGCTCAGTTGGTAGAGCTCCGCTCTTGCAATTGGGTCGTTGCGATTACGGGTCGTTGCGATTACGGGTCGTGCAATTGTCCAGGCGGTAATGATAGTATCTGTACCTGAA
    M TAGCTCAGTTGGTAGAGCTCCGCTCTTGCAATTGGGTCGTTGCGATTACGGGTCGTTGCGATTACGGGTCGTGCAATTGTCCAGGCGGTAATGATAGTATCTGTACCTGAA

****************************     *******                  ** ******** ** *********
    S CCGGTGGCTCACTTTTCTAAGTAATGGGAAAGAGGACCGAAACATGCCACTGAGACTCTACTGAGACAAA--GACGGGCTGTCAAGAACGTAGAACGAGGAGG
1401 T CCGGTGGCTCACTTTTTCTAAGTAATGGGAAGAGGAGGACCGAAACGTGCCACTGCCACTGAGACTCTACTGAGACAAA--GATGGGCTGTCAAGAACGTCAAGAACGTAGAGGAGG
    M CCGGTGGCTCACTTTTTCTAAGTAATGGGAAGAGGAGGACCGAAACATGCCACTGAAACTGAAACTGAGACTCTACTGAGACAAAAGATAGAGAAGGTAGAGGAGG
```

FIG. 4C

```
                ****************************************** **** ** ****** ** ********
     S  TAGGATGGGCAGTTGGTCAGTTGGTCAGATCTAGTAGTGATGTAGATGGAACGGTAGTGTTGGAGTCGGTGGCTCTCCTAGGGTTCCTCATTTGGGATC-CTGGGGAAG
1501 T  TAGGATGGGCAGTTGGTCAGTTGGTCAGATCTAGTAGTCGATCATGGACGGTAGTGTTGGAGTCCGGCGGCTCCTCCAGGGTCCCTCATCTGAGATCTCTGGGGAAG
     M  TAGGATGGGCAGTTGGTCAGTTGGTCAGATCTAGTAGATCTAGTATGGATCGTACATGGACGATAGTGTTGGAGTCGGCGGCTTCCTCCCTATCTGGGATCCCTGGGGAAG

********** *********************** *** ********        *********** *
     S  AGGATCAAGCTGGCCCTTGCGAACAGCTTGATGCACTATCCCTTCAACCCTTTGAGCGAAATGTGGC------AAAAGGAAAAAGAATCCATGGACCGA
1601 T  AGGATCAAGTTGGCCCTTGCGAACAGCTTGATGCACTATCCCTTCAACCCTTTGAGCGAAATGCGGCAAAAGAAAAAGGAAGAAAATCCATGGACCGA
     M  AGGATCAAGTTGGCCCTTGCGAATAGCTTGATGCACTATCCCTTCAACCCTTTGAGCGAAATGTGGC------AAAAGGAAGAAAATCCATGGACCGA

******   ********************************** ***  *  ** * ** * **********  *** **********
     S  CCCCATCGTCTCCACCCGTAGGAACTACGAGATCACCCCAAGGAAGCCTTCGGCATCCAGGGTCGGGACCGACCATAGAACCCTGTTCAAAAAGCG
1701 T  CCCCATCATCTCCACCCGTAGGAACTACGAGATCACCCCAAGGAACGCCTTCGGCATCCAGGGTCGGGACCGACCATAGAACCCTGTTCAATAAGTG
     M  CCCCATTGTCTCCACCCGTAGGAACTACGAGATCACCCCAAGGAGTTCGTCCTCCAATGGGGGTCTATCGGACCGACCATAG-ATCCTGTTCAATAAGTG

**** ** **** *********  ******  ***** ************ *********
     S  GAACGCATTAGCTATCCGCTCTCAGGTTGGACAGTAAGGGTCGGAGAAGGGCCAATACTCATTCTTA-112bpGTTAGAATGGATCCAACTCAGCACCTTT---
1801 T  GAACGCATTAGCTGTCCGCTCTCAGGTTGGGCAGTCAGGGTCGGCAGTAAGGGTCGGGAGAAGGGCCAATCATTCTTA------GTTAGAATGGATTCCAACTCAGCACCTTTGA
     M  GAACACAATAGCCGTCCGGTCTCCGGTCTGGGCAGTAAGGGTCGGGGAGGAGGGCAATGACTCACTCGTTCTTA-103bp-TTAGAATGGATTCCAACTCAGCACCTTTGT

** *** ********* ************ ***** *************************
     S  --TGAGATTTGAGAAGAGTTGCTCTTTGGAGAGCACAGTGAAAAGTGTGAGCTGTGTTCGGGGGAGTATTGTCTATCGTTGGCCTCTATGGT
1901 T  G-TGAGATTTGAGAAGAGTTGCTCTTTGGAGAGCACAGTGAAAAGTGTAAGCTGTGTTCGGGGGGAGTGTTGTAAGCGTTGGCCTCTATGGT
     M  TTTGGGATTTGAGAAGAGTTGTAAGCTGAAAGTTGTAAGCTGTGTTCGGGGGAGTATTGCCTATCGTTGTCCTCTATGGT
```

FIG. 4D

```
          ****  *  ********           *************************              ******************************  *  ***********     *****
     S AGAATCAGTCGGGG---CCTGAGAGGCGGTGGTTTACCCTGTGGCGGATGTGTCAGCGGTTCGAGTCCGCTTATCTCCAACTCGTGAACTTAGTCGATACAAA
2001 T AGAATCAGTCGGGG-GACTGAGAGGCCTGAGAGGCCTGGTTTACCCTGCGGCGGATGTGTCAGCGGTTCGAGTCCGCTTATCTCCAACTCGTGAACTTAGCCGATACAAA
     M AGAACCCGTCGGGGAGGCCTGAGAGGCGTGGTTTACCCTGTGGCGGATGTCAGCGGTTCGAGTCCGCTTATCTCCAGCCCGTGAACTTAGCGGATAC---

***
     S GCTA
2101 T GCTT
     M ---
```

\* indicates homology
- indicates gaps in the sequence compared to each other sequences
Nucleotide number corresponds to tobacco sequences only
S-soybean, T-tobacco, M-maize

FIG. 4E

```
PEA      (89 %)  GCTGCGCCAAGGAAAAGACTAAAAGACGGATTTGACTCCTTCATGCATGCTCCAACTTGGCTCGG
SPINACH  (89 %)  ACTGCGCCAAGAATAAGAATCGAAGAAGCGTCTGACTCCTTCATGCATGCTCCA-CTTGGCTCGG
                            /\
                            CGCCAGGGAA

TOBACCO  (-) --- CCGAGCCAAGTGGAGCATGCATGAAGTAGTCAGATGCTTCTTCTATTCTTTCCCTGGGCAGC
CUSCUTA  (96 %)  CCGAGCCAAGTGGAGCATGGGAGCATGAAGTAGTCAGTAGTCAGATACTTCTTCGATTCTTTTCCCTGGCGCAGC
```

FIG. 4G

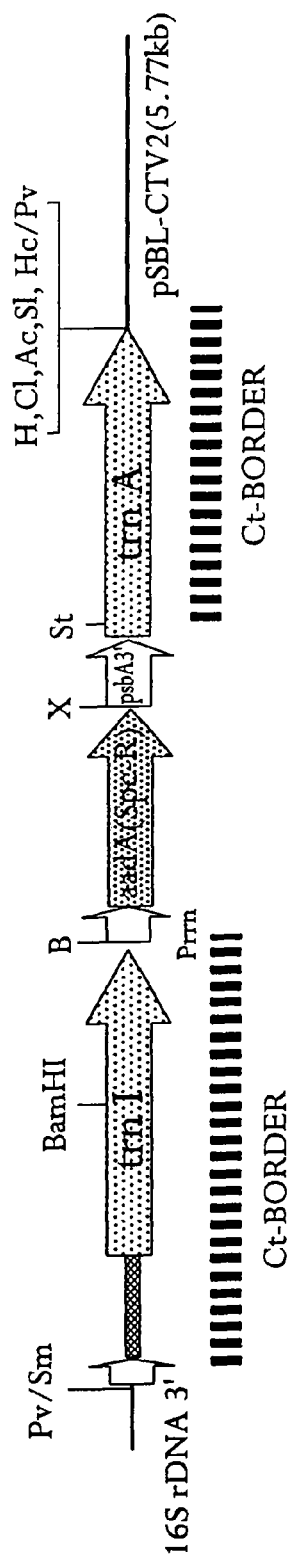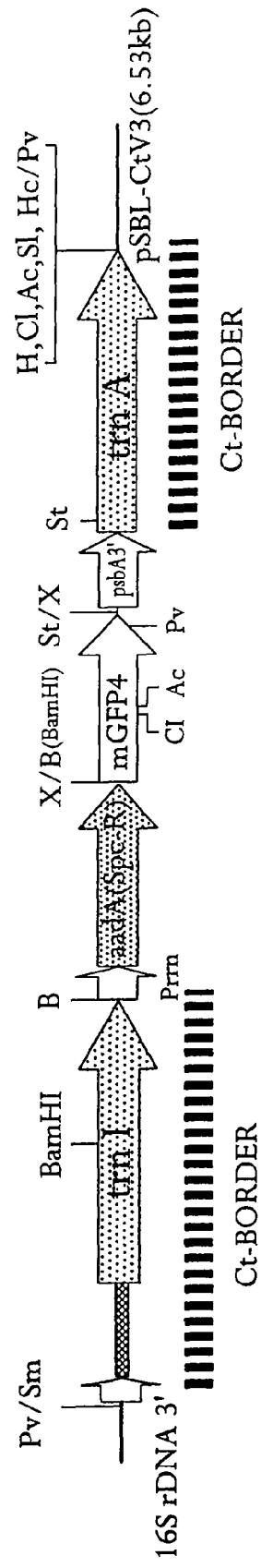
FIG. 7A
FIG. 7B

```
                        SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
        (A) LENGTH: 2050 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Soybean (xi) SEQUENCE DESCRIPTION: SEQ ID NO:1:

GTACACACCG CCCGTCACAC TATGGGAGCT GGCCATGCCG AAGTCGTTAC CTTAACCGCA         60

AGAGGGGAT GCCGAAGGCA GGGCTAGTGA CTGGAGTGAA GTCGTAACAA GGTAGCCGTA         120

CTGGAAGGTG CGGCTGGATC ACCTCCTTTT CAGGGAGAGC TAATGCTTGT TGGGTAGTTT        180

AGTTTGACAC TGCTTCACAC CCAAAAAGAA GCGAGTTATG TCTGAGTCAA ATTTGGAGAT        240

GGAAGTCTTC TTTCGTTTCT CGATGGTGAA GTAAGACTAA ACTCATGAGC TTATTATCCT       300

AGGTCGGAAC AAGTTGATAG GAGCTACTTT TTTCACCCCC ATATGGGGGT GAAAAAGGA        360

AAGAGAGGGA TGGGGTTTCT CTTGCTTTTG GCATAGCGGG CCCCGGCGGG AGGCCCGCAC       420
```

-continued

```
GACGGGCTAT TAGCTCAGTG GTAGAGCGCG CCCCTGATAA TTGCGTCGTT GTGCCTGGAC      480

TGTGAGGGCT CTCAGCCACA TGGATAGTTT AATGTGCTCA TCGGCGCCTG ACCCTGAGAT      540

GTGGATCATC CAAGGCACAT TAGCATGGCG TACTTCTCCT GTTTGAACCG GGGTTTGAAA      600

CCAAACTTAT CCTCAGGAGG ATAGATGGGG CGATTCAGGT GAGATCCAAT GTAGATCCAA      660

CTTTCTCTTC ACTCGTGGGA TCCGGGCGAT CCGGGGGGGA CCACCACGGC TCCTCTCTTC      720

TCGAGAATTC ATACATCCCT TATCAGTATA TGGACAGTTA TCTCTCGAGC ACAGGTTTAG      780

GTTTGGCCTC AATGGAAAAA AACGGAGCAC CTAACAACGT ATCTTCACAG ACCAAGAACT      840

ACGAGATCGC CCCTTTCATT CTGGGGTGAC GGTGGGATCG TACCATTCGA GCCTGGGAGC      900

AGGTTTGAAA AAGGATCTTA GAGTGTCTAG GGTTGTGCTA GGAGGGTCTC ATAATGCCTT      960

CCTTTTTCTT CTCATCGGAG TTATTTCCCA AAGACTTGCC ATGGTAAAGA AGAAGGGGGA     1020

ACAAGCACAC TTGGAGAGCG CAGTACAACG GATAGTTGTA TGCTGCGTTC GGGAAGGATG     1080

AATCGCTCCC GAAAAGGAAT CTATTGATTC TCTCCCAATT GGTTGGACTG TAGGTGCGAT     1140

GATTTACTTC ACGGGCGAGG TCTCTGGTTC AAGTCCAAGA TGGCCCAGCT GCGTCAAGGA     1200

AAAGAATAGA AAACTGACTT GACTCCTTCA TGCATGCTCC ACTCGGCTCG GGGGATATA     1260

GCTCAGTTGG TAGAGCTCCG CTCTTGCAAT TGGGTCGTTG CGATTACGGG TTGGATGTCT     1320

AATTGTCTAG GCGGTAATGA TAGTATCTTG TACCTGAACC GGTGGCTCAC TTTTTCTAAG     1380

TAATGGGAAA GAGGACCGAA ACATGCCACT GAAAGACTCT ACTGAGACAA AGACGGGCTG     1440

TCAAGAACGT AGAGGAGGTA GGATGGGCAG TTGGTCAGAT CTAGTATGGA TCGTACATGG     1500

ACGGTAGTTG GAGTCGGTGG CTCTCCTAGG GTTTCCTCAT TTGGGATCCT GGGGAAGAGG     1560

ATCAAGCTGG CCCTTGCGAA CAGCTTGATG CACTATCTCC CTTCAACCCT TTGAGCGAAA     1620

TGTGGCAAAA GGAAAAAGAA TCCATGGACC GACCCCATCG TCTCCACCCC GTAGGAACTA     1680

CGAGATCACC CCAAGGAACG CCTTCGGCAT CCAGGGGTCG CGGACCGACC ATAGAACCCT     1740

GTTCAAAAAG CGGAACGCAT TAGCTATCCG CTCTCAGGTT GGACAGTAAG GGTCGGAGAA     1800

GGGCAATCAC TCATTCTTAG TTAGAATGGG ATTCCAACTC AGCACCTTTT GAGATTTTGA     1860

GAAGAGTTGC TCTTTGGAGA GCACAGTACG ATGAAAGTTG TGAGCTGTGT TCGGGGGGA     1920

GTTATTGTCT ATCGTTGGCC TCTATGGTAG AATCAGTCGG GGCCTGAGAG GCGGTGGTTT     1980

ACCCTGTGGC GGATGTCAGC GGTTCGAGTC CGCTTATCTC CAACTCGTGA ACTTAGTCGA     2040

TACAAAGCTA                                                            2050

(2) INFORMATION FOR SEQ ID NO:2:

(i) SEQUENCE CHARACTERISTICS:
        (A) LENGTH: 2103 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Tobacco (xi) SEQUENCE DESCRIPTION: SEQ ID NO:2:

GTACACACCG CCCGTCACAC TATGGGAGCT GGCCATGCCC GAAGTCGTTA CCTTAACCGC       60

AAGGAGGGGG ATGCCGAAGG CAGGGCTAGT GACTGGAGTG AAGTCGTAAC AAGGTAGCCG      120

TACTGGAAGG TGCGGCTGGA TCACCTCCTT TTCAGGGAGA GCTAATGCTT GTTGGGTATT      180

TTGGTTTGAC ACTGCTTCAC ACCCCCAAAA AAAAGAAGGG AGCTACGTCT GAGTTAAACT      240
```

```
TGGAGATGGA AGTCTTCTTT CCTTTCTCGA CGGTGAAGTA AGACCAGCTC ATGAGCTTAT      300

TATCCTAGGT CGGAACAAGT TGATAGGACC CCCTTTTTTA CGTCCCCATG TTCCCCCCGT      360

GTGGCGACAT GGGGCGAAAA AAGGAAAGAG AGGGATGGGG TTTCTCTCGC TTTTGGCATA      420

GCGGGCCCCC AGTGGGAGGC TCGCACGACG GGCTATTAGC TCAGTGGTAG AGCGCGCCCC      480

TGATAATTGC GTCGTTGTGC CTGGGCTGTG AGGGCCTCTC AGCCACATGG ATAGTTCAAT      540

GTGCTCATCG GCGCCTGACC CTGAGATGTG GATCATCCAA GGCACATTAG CATGGCGTAC      600

TCCTCCTGTT CGAACCGGGG TTTGAAACCA AACTCCTCCT CAGGAGGATA GATGGGCGA      660

TTCGGGTGAG ATCCAATGTA GATCCAACTT TCGATTCACT CGTGGGATCC GGGCGGTCCG      720

GGGGGACCAC CACGGCTCCT CTCTTCTCGA GAATCCATAC ATCCCTTATC AGTGTATGGA      780

CAGCTATCTC TCGAGCACAG GTTAGCAAT GGGAAAATAA AATGGAGCAC CTAACAACGC      840

ATCTTCACAG ACCAAGAACT ACGAGATCGC CCCTTTCATT CTGGGGTGAC GGAGGGATCG      900

TACCATTCGA GCCGTTTTTT TCTTGACTCG AAATGGGAGC AGGTTTGAAA AAGGATCTTA      960

GAGTGTCTAG GGTTGGGCCA GGAGGGTCTC TTAACGCCTT CTTTTTTCTT CTCATCGGAG      1020

TTATTTCACA AAGACTTGCC AGGGTAAGGA AGAAGGGGGG AACAAGCACA CTTGGAGAGC      1080

GCAGTACAAC GGAGAGTTGT ATGCTGCGTT CGGGAAGGAT GAATCGCTCC CGAAAAGGAA      1140

TCTATTGATT CTCTCCCAAT TGGTTGGACC GTAGGTGCGA TGATTTACTT CACGGGCGAG      1200

GTCTCTGGTT CAAGTCCAGG ATGGCCCAGC TGCGCCAGGG AAAAGAATAG AAGAAGCATC      1260

TGACTACTTC ATGCATGCTC CACTTGGCTC GGGGGGATAT AGCTCAGTTG GTAGAGCTCC      1320

GCTCTTGCAA TTGGGTCGTT GCGATTACGG GTTGGATGTC TAATTGTCCA GGCGGTAATG      1380

ATAGTATCTT GTACCTGAAC CGGTGGCTCA CTTTTTCTAA GTAATGGGGA AGAGGACCGA      1440

AACGTGCCAC TGAAAGACTC TACTGAGACA AAGATGGGCT GTCAAGAACG TAGAGGAGGT      1500

AGGATGGGCA GTTGGTCAGA TCTAGTATGG ATCGTACATG GACGGTAGTT GGAGTCGGCG      1560

GCTCTCCCAG GGTTCCCTCA TCTGAGATCT CTGGGGAAGA GGATCAAGTT GGCCCTTGCG      1620

AACAGCTTGA TGCACTATCT CCCTTCAACC CTTTGAGCGA AATGCGGCAA AAGAAAAGGA      1680

AGGAAAATCC ATGGACCGAC CCCATCATCT CCACCCCGTA GGAACTACGA GATCACCCCA      1740

AGGAACGCCT TCGGCATCCA GGGGTCACGG ACCGACCATA GAACCCTGTT CAATAAGTGG      1800

AACGCATTAG CTGTCCGCTC TCAGGTTGGG CAGTCAGGGT CGGAGAAGGG CAATGACTCA      1860

TTCTTAGTTA GAATGGGATT CCAACTCAGC ACCTTTTGAG TGAGATTTTG AGAAGAGTTG      1920

CTCTTTGGAG AGCACAGTAC GATGAAAGTT GTAAGCTGTG TTCGGGGGGG AGTTATTGTC      1980

TATCGTTGGC CTCTATGGTA GAATCAGTCG GGGGACCTGA GAGGCGGTGG TTTACCCTGC      2040

GGCGGATGTC AGCGGTTCGA GTCCGCTTAT CTCCAACTCG TGAACTTAGC CGATACAAAG      2100

CTT                                                                   2103
```

(2) INFORMATION FOR SEQ ID NO:3:

(i) SEQUENCE CHARACTERISTICS:
        (A) LENGTH: 2103 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Maize (xi) SEQUENCE DESCRIPTION: SEQ ID NO:3:

```
GTACACACCG CCCGTCACAC TATAGGAGCT GGCCAGGTTT GAAGTCATTA CCCTTAACCG      60
TAAGGAGGGG GATGCCTAAG GCTAGGCTTG CGACTGGAGT GAAGTCGTAA CAAGGTAGCC     120
GTACTGGAAG GTGCGGCTGG ATCACCTCCT TTTCAGGGAG AGCTAAGTCT TATGCTTATT     180
GGGTATTTTG GTTTGACACT GCTTCACGCC CAAAAAGAAG GCAGCTACGT CTGAGCTAAA     240
CTTGGATATG GAAGTCTTCT TTCGTTTAGG GTGAAGTAAG ACCAAGCTCA TGAGCTTATT     300
ATCCTAGGTC GGAACAAATT AGTTGATAGT GATAGGATCC CCTTTTTGAC GTCCCCATGT     360
CCCCCCGTGT GGCGGCATGG GGATGTCAAA AGGAAAGGGA TGGAGTTTTT CTCGCTTTTG     420
GCGTAGCGGC CTCCCTTTGG GAGGCCGCGC GACGGGCTAT TAGCTCAGTG GTAGAGCGCG     480
CCCCTGATAA TTCGTCGTTG TGCCTCGGCT GTGAGGGCTC TCAGCCACAT GGATAGTTCA     540
ATGTGCTCAT CAGCGCCTGA CCCGAAGATG TGGATCATCC AAGGCACATT AGCATGGCGT     600
ACTCCTCCTG TTTGAATCGG AGTTTGAAAC CAAACAAACT TCTCCTCAGG AGGATAGATG     660
GGGCGATTCA GGTGAGATCC CATGTAGATC GAACTTTCTA TTCACTCGTG GGATCCGGGC     720
GGTCCGGGGG GGGGCCACCG GGGCTCCTCT CTTCTCGAGA ATCCATACAT CCCTTATCAG     780
TGTATGGAGA GCTATCTCTC GAGCACAGGT TGAGGTTCGT CCTCAATGGG AAAATGGAGC     840
ACCTAACAAC GCATCTTCAC AGACCAAGAA CTACGAGATC ACCCCTTTCA TTCTGGGGTG     900
ACGGAGGGAT CGTACCATTC GAGCCCTTGA CTCGAAATGG GAGCAGAGCA GGTTTGAAAA     960
AGGATCTTAG AGTGTCTAGG GTTGGGCCAG GAGGGTCTCT TAACCCCTTC TTTTTTCTGC    1020
CCATCGGAGT TATTTCCCAA GGACTTGCCG TGGTAAGGGG GAGAAGGGGG AAGAAGCACA    1080
CTTGAAGAGC GCAGTACAAC GGGGAGTTGT ATGCTGCGTT CGGGAAGGAT GGATCGCTCC    1140
CGAAAAGGAG TCTATTGATT CTCTCCCAAT TGGTTGGATC GTAGGGGCGA TGATTTACTT    1200
CACGGGCGAG GTCTCTGGTT CAAGTCCAGG ATGGCCCAGC TGCGCAGGGA AAAGAATAGA    1260
AGAAGCATCT GACTCTTTCA TGCATACTCC ACTTGGCTCG GGGGGATAT AGCTCAGTTG    1320
GTAGAGCTCC GCTCTTGCAA TTGGGTCGTT GCGATTACGG GTTGGCTGTC TAATTGTCCA    1380
GGCGGTAATG ATAGTATCTT GTACCTGAAC CGGTGGCTCA CTTTTTCTAA GTAATGGGGA    1440
AGAGGACTGA ACATGCCAC TGAAAGACTC TACTGAGACA AAAAGATGGG CTGTCAAAAA    1500
GGTAGAGGAG GTAGGATGGG CAGTTGGTCA GATCTAGTAT GGATCGTACA TGGACGATAG    1560
TTGGAGTCGG CGGCTCTCCT AGGCTTCCCT CATCTGGGAT CCCTGGGGAA GAGGATCAAG    1620
TTGGCCCTTG CGAATAGCTT GATGCACTAT CTCCCTTCAA CCCTTTGAGC GAAATGTGGC    1680
AAAAGGAAGG AAAATCCATG GACCGACCCC ATTGTCTCCA CCCCGTAGGA ACTACGAGAT    1740
CACCCCAAGG AGTTCGTCCT CAATGGGGGT CTATCGGACC GACCATAGAT CCTGTTCAAT    1800
AAGTGGAACA CAATAGCCGT CCGCTCTCCG GTTGGGCAGT AAGGGTCGGA GGAGGGCAAT    1860
CACTCGTTCT TATTAGAATG GGATTCCAAC TCAGCACCTT TTGTTTTGGG ATTTTGAGAA    1920
GAGTTGCTCT TTGGAGAGCA CAGTACGATG AAAGTTGTAA GCTGTGTTCG GGGGGAGTT    1980
ATTGCCTATC GTTGTCCTCT ATGGTAGAAC CCGTCGGGGA GGCCTGAGAG GCGGTGGTTT    2040
ACCCTGTGGC GGATGTCAGC GGTTCGAGTC CGCTTATCTC CAGCCCGTGA ACTTAGCGGA    2100
TAC                                                                 2103
```

(2) INFORMATION FOR SEQ ID NO:4:

(i) SEQUENCE CHARACTERISTICS:
        (A) LENGTH: 50 base pairs (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Epifagus (xi) SEQUENCE DESCRIPTION: SEQ ID NO:4:

GCTGCGCTAG GAAAAAATA TAAAAAGCAT CTGATTACTT CATGCATGCT                    50

(2) INFORMATION FOR SEQ ID NO:5:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Tobacco (xi) SEQUENCE DESCRIPTION: SEQ ID NO:5:

GCTGCGCCAG GGAAAAGAAT AGAAGAAGCA TCTGACTACT TCATGCATGC TCCACTTGGC        60

TCGG                                                                     64

(2) INFORMATION FOR SEQ ID NO:6:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Helianthus (xi) SEQUENCE DESCRIPTION: SEQ ID NO:6:

CGTGCGCCAG GGAAAAGAAT AGAAGAAGCG TCTGACTCCT TCATGCATGC TCCACTTGGC        60

TCGG                                                                     64

(2) INFORMATION FOR SEQ ID NO:7:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Oenothera (xi) SEQUENCE DESCRIPTION: SEQ ID NO:7:

GCTGCGCAAA GGAAAAGAAT AGAAGAAGCA TCTGACTCCT TCATGCATGC TCCACTTGGC        60

TCGG                                                                     64

(2) INFORMATION FOR SEQ ID NO:8:

(i) SEQUENCE CHARACTERISTICS:
        (A) LENGTH: 64 base pairs
        (B) TYPE: nucleic acid

```
            (C) STRANDEDNESS: single
            (D) TOPOLOGY: linear (ii) MOLECULE TYPE: DNA (genomic)

(vi) ORIGINAL SOURCE:
            (A) ORGANISM: Alnus (xi) SEQUENCE DESCRIPTION: SEQ ID NO:8:

GCTGCGCCAA GTAAAAGAAT AGAAGAAGCA TCTGACTCCT TCATGCATGC TCCACTTGGC      60

TCGG                                                                  64

(2) INFORMATION FOR SEQ ID NO:9:

(i) SEQUENCE CHARACTERISTICS:
            (A) LENGTH: 64 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Rice (xi) SEQUENCE DESCRIPTION: SEQ ID NO:9:

GCTGCGCCAG GGAAAAGAAT AGAAGAAGCA TCTGACTCTT TCATGCATAC TCCACTTGGC      60

TCGG                                                                  64

(2) INFORMATION FOR SEQ ID NO:10:

(i) SEQUENCE CHARACTERISTICS:
            (A) LENGTH: 63 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Maize (xi) SEQUENCE DESCRIPTION: SEQ ID NO:10:

GCTGCGCAGG GAAAAGAATA GAAGAAGCAT CTGACTCTTT CATGCATACT CCACTTGGCT      60

CGG                                                                   63

(2) INFORMATION FOR SEQ ID NO:11:

(i) SEQUENCE CHARACTERISTICS:
            (A) LENGTH: 64 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Soybean (xi) SEQUENCE DESCRIPTION: SEQ ID NO:11:

GCTGCGTCAA GGAAAAGAAT AGAAAACTGA CTTGACTCCT TCATGCATGC TCCACTCGGC      60

TCGG                                                                  64

(2) INFORMATION FOR SEQ ID NO:12:

(i) SEQUENCE CHARACTERISTICS:
            (A) LENGTH: 65 base pairs
```

```
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pea (xi) SEQUENCE DESCRIPTION: SEQ ID NO:12:

GCTGCGCCAA GGAAAAGACT AAAAGACGGA TTTGACTCCT TCATGCATGC TCCAACTTGG      60

CTCGG                                                                 65

(2) INFORMATION FOR SEQ ID NO:13:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Spinach (xi) SEQUENCE DESCRIPTION: SEQ ID NO:13:

ACTGCGCCAA GAATAAGAAT CGAAGAAGCG TCTGACTCCT TCATGCATGC TCCACTTGGC      60

TCGG                                                                  64

(2) INFORMATION FOR SEQ ID NO:14:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CGCCAGGGAA                                                            10

(2) INFORMATION FOR SEQ ID NO:15:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Tobacco (xi) SEQUENCE DESCRIPTION: SEQ ID NO:15:

CCGAGCCAAG TGGAGCATGC ATGAAGTAGT CAGATGCTTC TTCTATTCTT TTCCCTGGCG      60

CAGC                                                                  64

(2) INFORMATION FOR SEQ ID NO:16:

(i) SEQUENCE CHARACTERISTICS:
        (A) LENGTH: 64 base pairs
        (B) TYPE: nucleic acid
        (C) STRANDEDNESS: single
        (D) TOPOLOGY: linear
```

-continued

```
    (ii) MOLECULE TYPE: DNA (genomic)

(vi) ORIGINAL SOURCE:
         (A) ORGANISM: Cuscuta (xi) SEQUENCE DESCRIPTION: SEQ ID NO:16:

CCGAGCCAAG TGGAGCATGC ATGAAGTAGT CAGATACTTC TTCGATTCTT TTCCCTGGCG        60

CAGC                                                                    64

(2) INFORMATION FOR SEQ ID NO:17:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:17:

Gly Val Gly Val Pro
1               5

(2) INFORMATION FOR SEQ ID NO:18:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:18:

Val Pro Gly Val Pro
1               5
```

UNIVERSAL CHLOROPLAST INTEGRATION AND EXPRESSION VECTORS, TRANSFORMED PLANTS AND PRODUCTS THEREOF

RELATED APPLICATIONS

This application is a continuation of U.S. Ser. No. 09/079,640 filed May 15, 1998, now U.S. Pat. No. 7,129,391, which claims benefit of provisional application Ser. No. 60/079,042 filed Mar. 23, 1998, and provisional application No. 60/055,314 filed Aug. 7, 1997, both incorporated herein by reference in their entirety.

FIELD OF THE INVENTION

This application pertains to the field of genetic engineering of plant genomes, particularly the genetic engineering of the genome of plant plastids, such as chloroplasts and to the stable transformation of chloroplast genome of any plant species.

RELATED CASES

This application relates in particular to a universal chloroplast expression and integration vector which is competent to transform any plant with one or more genes of interest. The earlier U.S. Pat. No. 5,932,479 teaches plant cells transformed by means of an expression cassette comprising an exogenous DNA sequence which is stably integrated (covalently linked) to the chloroplast genome of the cell of a target plant. "Stably" integrated DNA sequences are those which are inherited through genome replication by daughter cells or organisms. This stability is exhibited by the ability to establish permanent cell lines, clones, or transgenic plants comprised of a population containing the exogenous DNA.

Likewise, U.S. Pat. No. 5,693,507 (1997) to Daniell and McFadden discloses such stable integration by means of an expression cassette which comprises an exogenous DNA sequence which codes for a desired trait, and the transformed plants.

BACKGROUND OF THE INVENTION

Advantages of Chloroplast Transformation Over Nuclear Transformation. The attractiveness of transformation of the chloroplast genome over transformation of the nuclear genome is attributable to the serious risks resulting from the latter. One common concern is the escape of foreign genes through pollen dispersal from transgenic crop plants to their weedy relatives. It has been demonstrated that transgenic pollen will deliver foreign (transgenic) genes to other sexually-compatible plants (detected by marker gene prevalence in progeny harvested from non-transgenic plants grown in surrounding area). For Example, dispersal of pollen from a central test plot containing transgenic cotton plants to surrounding non-transgenic plants has been observed at varying distances in different directions. (Lewellyn and Fitt, 1996); (Umbeck, P. F., et al., 1991). In addition, the frequencies of marker genes in wild sunflowers averaged about 28 to 38%; in wild strawberries growing within 50 meters of a strawberry field, more than 50% of the wild plants contained marker genes from cultivated strawberries. (King, J., 1996).

The escape of foreign genes through pollen is especially a serious environmental concern, in the case of herbicide resistance genes, because of the high rates of gene flow from crops to wild relatives. The concern is that gene escape from transgenic crops to their weedy relatives will create super weeds. In rice (*Oryza sativa*), gene flow from cultivated varieties to wild relatives has been noted, into *O. perennis* (Barrett, 1983) and red rice (*O. sativa*; Langevin et al., 1990). In the southern US, red rice has become a major weed because herbicides that kill it also kills cultivated rice. Decreased prices are paid for cultivated rice contaminated with red rice. Some researchers have introduced the bar gene conferring resistance to glufosinate (Liberty) into cultivated rice to combat this weed (Oard et al., 1996; Sankula et al., 1996). However, due to sexual compatibility, introduction of a nuclear-expressed gene will allow transmission of that resistance trait into red rice via pollen.

Similarly, transgenic oil seed rape, genetically engineered for herbicide resistance outcrossed with a weedy relative, *Brassica campestris* (field mustard) and conferred herbicide resistance even in the first back-cross generation under field conditions. (Mikkelson, T. R., et al., 1996).

Maternal inheritance of introduced genes prevents gene escape through pollen. Engineering foreign genes through chloroplast genomes (which are maternally inherited for most of the crops) is a solution to this problem. Also, the target enzymes or proteins for most herbicides (e.g. amino acid/ fatty acid biosynthetic pathways or photosynthesis) are compartmentalized within the chloroplast. Another important advantage of chloroplast transformation is the higher levels of foreign gene expression due to a very high copy number (5000-10,000) of chloroplast genomes in plant cells. Because the transcriptional and translational machinery of the chloroplast is prokaryotic in nature, herbicide resistant genes of bacterial origin can be expressed at extraordinarily high levels in chloroplasts.

Transformation of the Chloroplast Genome. Early investigations on chloroplast transformation focused on the development of in organello systems using intact chloroplasts capable of efficient and prolonged transcription and translation (Daniell and Rebeiz, 1982; Daniell et al., 1983) and expression of foreign genes in isolated chloroplasts (Daniell and McFadden, 1987). These experiments were done under the premise that it was possible to introduce isolated intact chloroplasts into protoplasts and regenerate transgenic plants (Carlson, 1973). The discovery of the gene gun as a transformation device opened the possibility of direct plastid transformation in plants (Daniell, 1993). Transient expression of foreign genes in plastids of dicots (Daniell et al., 1990; Ye et al., 1990), monocots (Daniell et al., 1991), prolonged foreign gene expression using autonomously replicating chloroplast expression vectors (Daniell et al., 1990) and stable integration of a selectable marker into the tobacco chloroplast genome (Svab and Maliga, 1993) were accomplished using the gene gun. Tobacco plants resistant to certain insects were obtained by integrating the cryIAc gene into the tobacco chloroplast genome (McBride et al., 1995; U.S. Pat. No. 5,451,513, incorporated herein by reference). Stable plastid transformation of higher plants has been accomplished so far only in tobacco.

Prior Studies on the Chloroplast Genome. To date, stable integration of a foreign gene into the chloroplast genome of a higher plant has been reported only in tobacco. This was achieved with a vector which was specific for tobacco and which was derived from the tobacco chloroplast genome, that is, the vector contained a sequence homologous only to the tobacco chloroplast genome and which is not highly conserved in the chloroplast genomes of other plants. Such vector is unsuitable for stably transforming plant species other than tobacco. The only published report of foreign gene expression in a plant species other than tobacco is that of wheat leaves and embryos (Daniell et al., 1991), but stable integration was not accomplished. Stable integration of a foreign gene into the chloroplast genome of a monocotyledonous plant has never been reported. At least in cereals (monocots), previously developed transformation/regeneration protocols may not be amenable to plastid transformation due to inherent inefficiencies within those systems. Also, sequential/serial selections (repeated selections), deemed important for achieving homoplasmy (Daniell, 1997), may not be feasible using those regeneration systems employed. Recent development of unique corn (Rudraswamy, 1997) and rice (unpublished) transformation/regeneration protocols have the potential to exhibit substantially increased efficiencies and allow more than one round of selection during regeneration.

Maliga et al. in U.S. Pat. No. 5,451,513 and Svab et al., 1990 propose a transformation of the plastid genome of tobacco by a non-lethal selection technique which employs plastid DNA encoding a non-lethal selectable phenotype. According to Maliga et al. a non-lethal selection is absolutely essential for obtaining transplastgenic lines.

Unlike the Maliga et al. technique, the method of the invention provides a selection which is lethal to all non-transformed plants, but for tobacco. Only the transformed plants survive and continue to grow. This lethal selection takes place with virtually all antibiotics, including spectinomycin and streptomycin in a medium containing the antibiotic in a concentration of 500-1,000 µg/ml. Similar conditions were shown to be non-lethal for tobacco by Maliga et al. Moreover, unlike the technique of Maliga et al., in accordance with the invention, transformation to homoplasmy can be achieved even in the first round of selection.

In European Patent Application No. 0 251 654, Cannon et al. describe transposon-mediated chloroplast transformation of tobacco for instance, using the bacterial transposon Tn5. The vector containing the transposon is targeted at a chromosomal region known to be a "transcriptionally silent" region in order to preserve the transcriptional integrity of the native genes. Such a transcriptionally silent region is identified to be located between two known divergent promoters of chloroplast genes, e.g. the promoters for the genes for the chloroplast large subunit of ribulose bisphosphate carboxylate (RbcL, "LS RuBis Co") and for β-ATPase (atpB). These promoters transcribe the genes in opposite directions away from the silent region of the chromosome. No transcription terminator is provided in the expression vector of Cannon et al., such terminator regions are known to be absolutely essential for gene expression in plastids. Finally, no stable chloroplast transformation is shown to be accomplished by Cannon et al.

The invention described herein has several distinguishing features over Cannon et al. The invention teaches stable transformation transmittable to the progeny. The integration is not directed into a transcriptionally inactive region of the chloroplast chromosome. The invention integrates a cassette (which contains a transcription terminator as described further hereinafter) into a transcriptionally active region of the chloroplast genome. Promoters controls the expression of one or more genes. Unlike Cannon et al. no transposon is involved in the transformation of the chloroplast in accordance with the invention.

In NATO Asi Series, Daniell et al., 1994 report engineering insect resistance via chloroplast genomes showing the expression of CryII-A protein in plants to control insects. McBride et al, 1995, and U.S. Pat. No. 5,545,818 (1996), confirm report of Daniell et al and show the expression of *Bacillus thuringiensis* CRYIAc protein into plant plastids. The vectors reported by McBride are designed to introduce the construct only into the tobacco chloroplast genome.

The Need for a Vector to Transform a Variety of Plants. It is evident from the state of the art that an important need exists for a chloroplast integration and expression vector for transforming, preferably stably, the chloroplast genomes of many different species of plants. Such a "universal vector" would permit the transformation of the chloroplast genome of a selected target plant with a heterologous (foreign) DNA coding sequence and eliminate the need to construct vectors which each one is specifically suited to transform the chloroplast genome of the particular plant species which is to be transformed.

The problem to construct such a universal vector competent to transform different plants has to the knowledge of the inventor, not yet been solved.

Prior Art Concepts of the Intergenic Spacer Region. While the nucleotide sequence of coding regions of the genome, including the chloroplast genome, are often conserved between species, in contrast the sequences flanking functional genes, i.e. the spacer regions between coding regions typically are not conserved. The accepted dogma for lack of conservation, and thus the low degree of homology between species of spacer regions, is that the spacer regions typically do not perform essential functions. Therefore, there is little, if any, selective pressure to conserve the sequence of spacer regions between species. The sequence of the spacer regions may be altered without undesirable effects.

Stummann et al., 1988, disclose that the gene order of the ribosomal RNA operon of the chloroplast genome is the same between different species of plants, including tobacco, maize, and a liverwort, *Marchantia*, and that the coding sequences of this operon are highly homologous. Stummann also discloses that the interspecies homology of the operon is less than the interspecies homology of the gene coding regions. This is consistent with the lack of conservation of spacer regions; and suggests that the interspecies homology of spacer regions in the ribosomal RNA operon is relatively low.

The invention, contrary to the dogma of lack of conservation of the spacer regions, uses spacer regions that are highly conserved between different plants to construct vectors competent to transform a variety of plants.

OVERVIEW OF THE INVENTION

The invention provides universal chloroplast integration and expression vectors which are competent to stably transform and integrate genes of interest into chloroplast genome of multiple species of plants. Transformed plants and their progeny are provided. Monocotyledonous and dicotyledonous plant are transformed which have never been transformed heretofore. Plants transformed with a synthetic gene express valuable biodegradable protein-based polymers (PBPs). Transformed plants produce high value molecules. Resistance is provided to agricultural crops against the major classes of chemical herbicides. Herbicide resistance is used as a lethal selectable marker for chloroplast transformation. The transformed plants are capable of expressing in addition to the targeted trait, a desirable, secondary non-targeted trait. Insect resistance is provided to transformed plants, both against insects that are susceptible to Bt toxins and against insects that have developed a resistance to Bt toxins.

SUMMARY OF THE INVENTION

The Intergenic Spacer Region. The Invention's Concept.

It has been discovered contrary to the conventional belief, that the chloroplast (ct) genome of plants contains spacer regions with highly conserved nucleotide sequences. The highly conserved nature of the nucleotide sequences of these spacer regions of the chloroplast genome makes such spacer regions, it has been discovered, ideal for the construction of vectors to transform chloroplasts of widely varying species of plant, this without the necessity of constructing individual vectors for different plants or individual crop species, which would require first a determination of the DNA sequence of each of the chloroplast genomes. This finding has numerous useful consequences and important practical applications.

The Several Embodiments of the Invention

The Universal Vector. The invention has several useful embodiments. The invention provides a universal integration and expression vector hereinafter referred to as "UV" and its use for the expression of at least one phenotype in a variety of different plants.

The integration expression universal vector of the invention comprises an expression cassette (further described below) which comprises the necessary genetic elements to transiently or preferably stably transform the plastids e.g. chloroplast genome of a target plant cell with a foreign (heterologous) DNA coding for a molecule of interest, like a phenotype to be expressed by the plant or a non-plant high value molecule, like a biologically active peptide (or polypeptide). The universal vector is constructed with a transcriptionally active region of a chloroplast genome that is highly conserved in a broad range of chloroplast genomes of higher plants. Preferably that region is the spacer 2 region; the intergenic spacer region between the t-RNA$^{Ile}$ and the tRNA$^{Ala}$ region. Such region is often referred to herein as a "spacer" region because in the chloroplast genome it is intergenic between several genes in the rRNA operon which is transcribed by one promoter. When built into the universal vector such region is generally referred to herein as a "border" or preferably as a "flanking sequence" or "flanking sequences". This is because in the universal vector, the operably joined genetic elements for transforming stably the plastid of the target plant are flanked on each side by a sequence i.e. a fragment of the spacer region. The flanking sequences in the vector and the spacer sequences in the chloroplast genome have sufficient homology to each other to undergo homologous recombination. The universal vector is inserted into the spacer of a transcriptionally active region in the chloroplast genome. Generally, the spacer region is positioned in the inverted repeat region of the chloroplast genome. The rest of the construct, i.e. other than the flanking sequences and the expression cassette, is generally referred to herein as the "vector" which comprises bacterial sequences, like the plasmid cloning vectors pUC, pBR322, pGEM or pBlueScript.

The Expression Vector or Cassette. The universal vector comprises an expression cassette which is flanked on each side by a flanking sequence. A suitable expression cassette for use in the invention is described in U.S. Pat. No. 5,693,507 (1997), which is incorporated herein by reference. That cassette comprises, operably joined, a transcriptional initiation region functional in plant chloroplast, at least one heterologous DNA sequence coding for a target molecule of interest, e.g. a gene (or functional fraction thereof) encoding a biologically active compound, and control sequences positioned upstream for the 5' and downstream from the 3' ends and a transcription termination region to provide expression of the coding sequence in the chloroplast genome of a target plant. Preferably, the expression cassette is flanked by plant DNA sequences, like chloroplast DNA sequences, in order to facilitate stable integration of the expression vector into the chloroplast genome. In the construction of the expression cassette, the DNA sequence comprises one or more cloning site(s) for integration of the gene(s) of interest.

The spacer sequences that have been identified in plastids of higher plants are ubiquitously conserved between a great variety of plants. These sequences were found to be ideal to construct the universal vectors of the invention which are, as a result, competent to transform the chloroplast genome of a large variety (or multiplicity) of target plants by homologous recombination. It is thus immaterial from which individual spacer of a particular plant the universal vector is constructed.

As is known, it will be generally advisable to have at least one additional heterologous nucleotide sequence coding for a selectable phenotype, such as a gene providing for antibiotic resistance or a functional portion thereof to serve as a marker associated with the expression cassette or with the universal integration expression vector. This facilitates identification of the plant cells in which the foreign gene has been stably integrated. Marker genes are known in the literature, for instance β-lactanase, herbicide resistant genes such as the mutant psbA gene or EPSPS-aroA, the cat gene which encodes chloramphenicol acetotranferase, and the uidA gene encodes β-glucuronidase (gus) and others.

It is recognized that tobacco is unique in being not susceptible to the lethal affect of streptomycin and spectinomycin. Though tobacco leaves lack the pigmentation when exposed to a medium with such an antibiotic, continued growth is observable. However, this property of tobacco is readily circumvented. There are numerous antibiotics available which are lethal for tobacco, like hygromycin. Another approach is to select a gene which expresses a visible marker like a color, fluorescence, etc., like the reporter gene mGFP, that codes for a green fluorescent protein.

Method of Transformation. The invention provides a transformation method which can produce homoplasmy (integration of foreign genes into all of the chloroplast genomes of the plant cell) after a first round of selection without the need for a further selection process. The method for transforming a plant uses the universal vector constructed with flanking sequences from a plant species other than the species of the target plant to be transformed. Alternatively, the vector may contain flanking sequences from the same plant species as the target plant, including from tobacco.

Method to Construct the Universal Vector. The invention further provides a method to construct the universal chloroplast integration and expression vector. To this effect, a spacer portion of the chloroplast genome from any plant is determined to be highly homologous to more than one species of plants. A nucleotide sequence corresponding to that spacer region is obtained from the identified chloroplast genome (or synthesized) and is incorporated into a suitable vector, such as by subcloning into a plasmid. The spacer region is positioned as flanking sequences to the expression cassette comprising the necessary genetic elements for transformation of the plastid and expression of the foreign gene(s).

Any method of transformation of the chloroplast may be used. Any gene (or functional portion thereof) which may be utilized to transform a plant chloroplast and encode a desired peptide to confer the desired trait to the target plant is suitable for transformation with the universal vector.

Transformed Plants. The invention further provides plants in which the chloroplast genome has been stably, that is, permanently transformed with the universal vector of the invention, including the progeny thereof.

The invention includes monocotyledonous plants like cereals or plant cells, such as maize, rice, barley, oat, wheat and grasses, and their progeny in which the chloroplast genome has been stably transformed with the universal vector derived from the same species or from a different species than the transformed plant. The invention provides dicotyledonous and monocotyledonous plants, stably transformed following a single round of selection, due to homoplasmy achievable with the universal vector comprising a chloroplast origin of replication (ori). The invention also provides stably transformed plants of differing species, including varieties of the same species, genera, families, orders, and divisions of plants.

In accordance with the invention, a plant in which the chloroplast genome has been stably transformed with one or more foreign genes of interest includes mature plants and progeny thereof, like seedlings and embryos. The term "plant" in this context also includes portions of plants such as explants like cuttings, tissue cultures, cell suspensions, and calli.

Thus, the invention includes the stably transformed multicellular plants, their progeny, the seed, and the transformed plastids, e.g. the chloroplast, etc., and method of regenerating the transformed plants.

In this specification and in the claims, when reference is made to different "species", the term "species" refers not only to "species" but to varieties within a species, genera, families, order, and divisions of the plant kingdom. Thus, a universal vector which can be used to transform plants of different species is understood to be able to transform plants of different varieties within a species, different genera, different families, different orders, and different divisions. The term "plant" (or "plants") is intended to be generic as used herein.

Expression of Non-plant Products

Biopolymer genes. Another embodiment of the invention using the universal integration and expression vector provides plants transformed with a synthetic biopolymer gene that codes for biodegradable protein-based polymers (PBPs).

These polymers have important properties of practical importance, discussed hereinafter.

Production of High Value Molecules-Biologically Active Molecules. The intriguing discovery that transformation with a synthetic gene which need not have a natural analogue in plant or animal, to produce PBPs, is feasible, has shown the wide applicability of the vector in yet another field of human endeavor: the production of biologically active molecules, like pharmaceuticals in plants, from any gene or functional fraction thereof, synthetic or natural.

A further embodiment of the invention is therefore the use of transformed plants as bioreactors (as factories) for biopharmaceuticals. There are at least two capabilities often needed for the production of proteins of pharmaceutical value, not possible in prokaryotic systems. Plants, unlike bacteria, are able to produce the foreign protein in a biological active conformation. Plants are also often more tolerant to the alteration of their biosynthetic pathways. Thus, the plants can be transformed with a gene non-functional in (or foreign to) plants, that may be synthetic or not, that may normally be functional (competent) in animals (mammals), in oviparous, in pesces or other species.

The invention further provides transformed plants comprising a gene provided by an expression cassette, preferably by a universal vector, which codes for a variety of desired products, especially biologically active molecules like peptides (polypeptides), proteins, insulin, human serum albumin (HSA) and other molecules further described hereinafter. The plants are allowed or caused to grow, and the products are isolated from the transformed crop, like tobacco, maize, etc., and if desirable, harvested first and if necessary, purified.

Herbicide Tolerance. Another important embodiment of the invention provides transgenic herbicide resistant plants in which a foreign transgene conferring resistance to one or more herbicides are integrated, preferably stably, into the chloroplast genome by means of the universal vector. Of particular importance are transformed plants which exhibit glyphosate resistance and thus be resistant to "ROUNDUP™", a herbicide available commercially from Monsanto Company. The universal vector provides an effective means to transform the chloroplast genome of any plant and to confer resistance (or tolerance) to any of the herbicidal chemicals.

A different aspect of the invention provides a method to transform a plant by means of an expression cassette, preferably by means of the universal vector, to cause it to produce a non-targeted (secondary or other) trait (or phenotype). [See, for example, Penazloza, V., et al. (1995), who report that expression by gromycin β-phosphotransferace gene confers resistance to the herbicide glyphosate.]

In another aspect of the invention, herbicide tolerance is used as a marker gene for chloroplast transformation.

Insect Resistance. A further embodiment of the invention provides insect resistance. With the increased concerns of using chemical pesticides, the use of *Bacillus thuringiensis* (Bt) formulations has been widely advocated. *Bacillus thuringiensis* produces many types of crystalline inclusions which are toxic to insects. The proteins comprising these inclusions have been categorized based on insecticidal host range, and protein homology. The CRYI and CRYII toxins have insecticidal activity against lepidoptera, or lepidoptera and diptera, respectively. CRYI protoxins are 130-135 kDa in size which are enzymatically cleaved into proteins of 65 kDa for insecticidal activity. CRYII protoxin is 65 kDa in size with a protein with a molecular mass of 60-62 kDa for insecticidal activity. Many commercially important insects pests (especially in the family Pyralidae) are susceptible to CryIIA toxin, including European corn borer, *Ostrinia nubilalis*, lesser cornstalk borer, *Elasmopalpus lignosellus*, cowpea pod borer, *Maruca testulalis*, tobacco budworm, *Heliothis virescens*, tobacco hornworm, *Manduca sexta* and gypsy moth *Lymantria dispar*, Daniell et al. 1994.

However, Bt formulations have not been as effective as anticipated primarily due to their susceptibility to UV radiation, inadequate coverage, expense and limited host range. Delivery of Bt toxins via Bt-transgenic plants is therefore appealing.

Acceptable insect control has occurred with nuclear-transgenic Bt cotton against the tobacco budworm, *Heliothis virescens*, but these plants do not express enough Bt toxin to control the cotton bollworm, *Helicoverpa zea*. Additionally, these Bt genes may outcross to related plant species via pollen. To circumvent these concerns, chloroplast transformation and expression has been evaluated in accordance with the invention because of the following reasons. 1) Plant cells containing chloroplasts can contain up to 10,000 gene copies per cell, 2) chloroplasts can read intact bacterial DNA, including operons, and 3) chloroplast genomes are maternally inherited, and therefore, foreign gene escape via the pollen is drastically eliminated because chloroplast DNA is generally degraded in pollen.

CRY2A was chosen because CRY2A is relatively non-homologous to CRY1A and therefore, displays only slight cross resistance against some CRY1A-resistant *H. virescens* populations. Because CRY2A is a "naturally truncated" high expression levels may be achieved without sacrificing the 3' region.

According resistance has been provided to tobacco chloroplast genome transformed with a universal vector of the invention to insects normally susceptible to Bt toxins and also to insects that have developed resistance or less susceptibility to Bt toxins. Insects that had never been killed by any CRY toxin showed 100% mortality on transformed tobacco.

The expression of cry2A in a plant could therefore be a valuable tool in controlling multiple insect pests while overcoming the development of Bt resistance. Other insecticidal proteins such as cholesterol oxidase that kill boll weevil by a different mechanism, are expressed to high levels in chloroplasts.

Other embodiments of the invention will become apparent hereinafter.

DESCRIPTION OF THE DRAWINGS

FIG. 2A shows the tobacco chloroplast vector (TV) pZS-RD-EPSPS for expression of herbicide resistance.

FIG. 2B shows the universal chloroplast expression and integration vector (UV), pSBL-RD-EPSPS for expression of herbicide resistance.

FIG. 3A shows the universal chloroplast integration and expression vector, pSBL-CG-EG121 for biopolymer expression.

FIG. 3B shows the tobacco integration and expression and vector, pZS-CG-EG121 for biopolymer expression.

FIGS. 7A-D shows vectors pSBL-CtV2, pSBL-CtV3, pSBL-CtVH, pSBL-CtVHF, respectively.

Preferred embodiments of the invention are described in greater detail hereinafter.

DETAILED DESCRIPTION OF THE INVENTION

The Universal Integration and Expression Vector. The universal integration and expression vector of the invention is competent for stably transforming chloroplasts of various different target plants. Heterologous DNA coding sequences can be provided in the cassette to code for a phenotype such as herbicide resistance, insect resistance or other traits. The vector further comprises a flanking sequence on each side of the DNA coding sequence which is homologous to a spacer sequence of the chloroplast genome, which spacer sequence is conserved in the chloroplast genomes of different plants. In this manner, stable integration of the heterologous gene into the chloroplast genome of the target plant is facilitated through homologous recombination of the flanking border sequences with complimentary spacer sequences in the chloroplast genome. The universal vector is competent to transform any plant species.

Figure 4B:
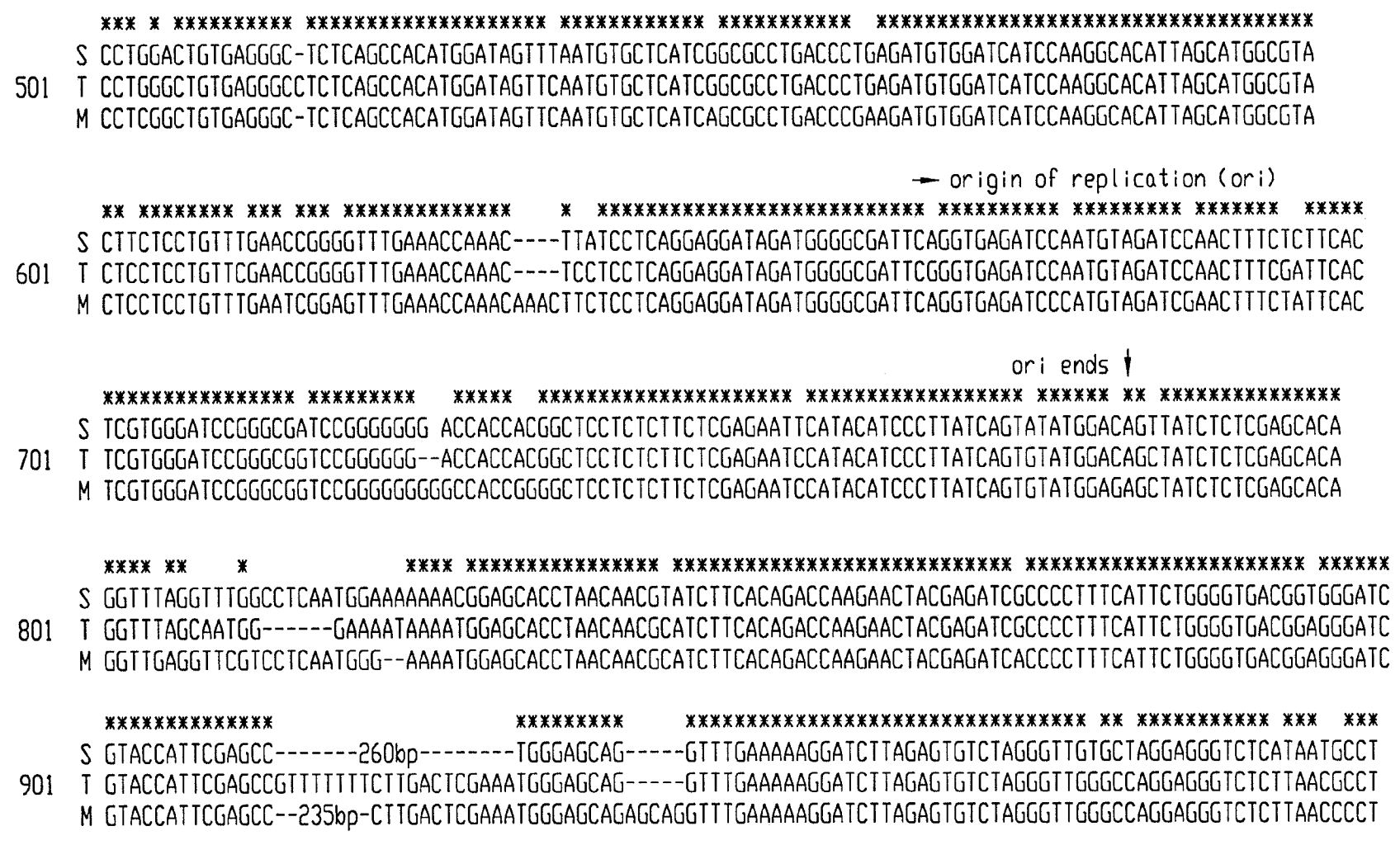
Figure 4F:
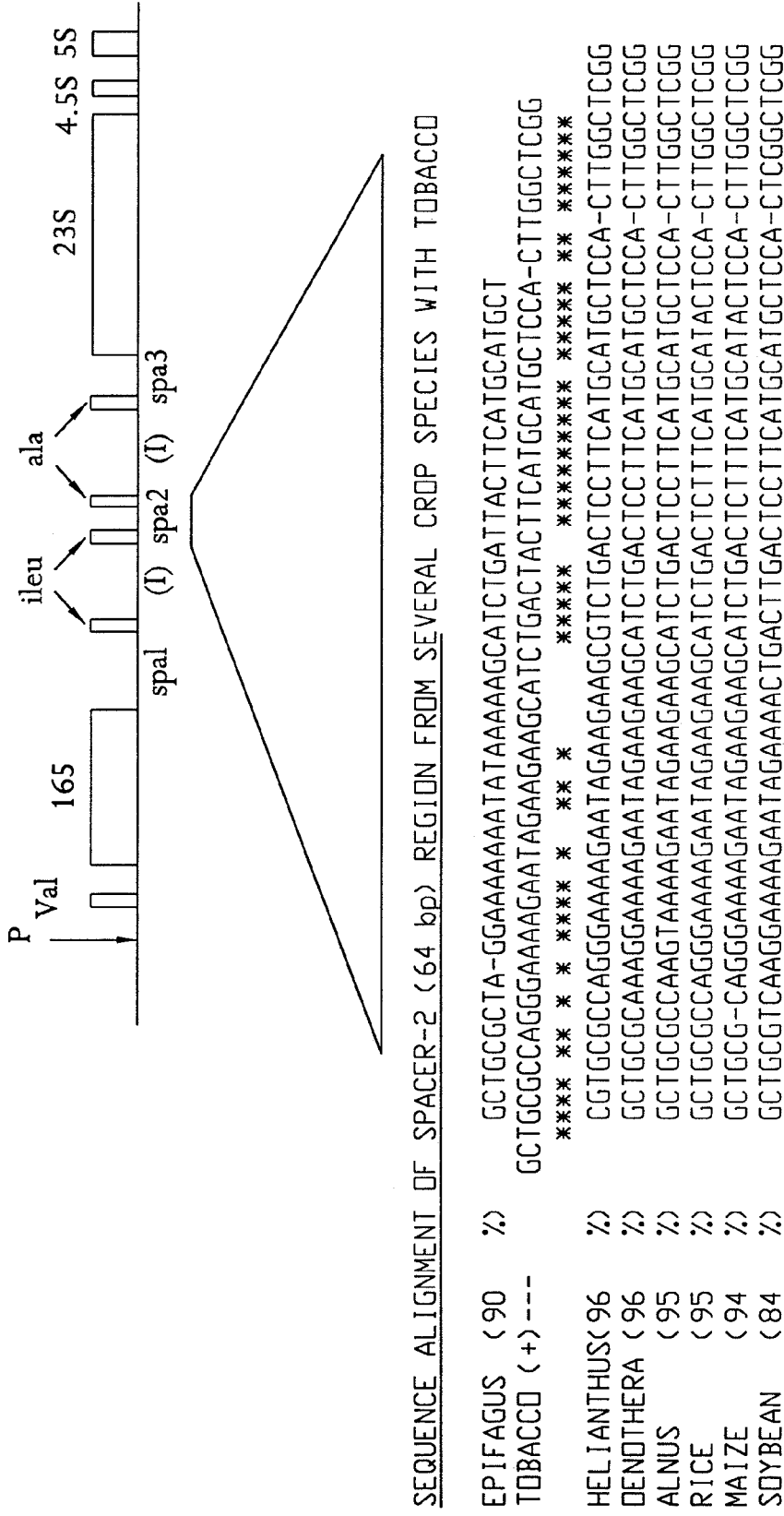
FIGS. 4A-4E show the sequence homology (SEQ ID NO: 1, SEQ ID NO: 2, and SEQ ID NO:3) of spacer regions between tobacco and other crop species. A site for foreign gene insertion is shown by arrows. Upstream of the site for foreign gene insertion the site of an origin or replication (ori) is shown.
FIGS. 4-F-4G show the sequence alignment SEQ ID NO: 4 (Epifagus), SEQ ID NO: 5 (Tobacco), SEQ ID NO: 6 (Helianthus), SEQ ID NO: 7 (Oenothera), SEQ ID NO: 8 (Alnus), SEQ ID NO: 9 (Rice), SEQ ID NO: 10 (Maize), SEQ ID NO: 11 (Soybean), SEQ ID NO: 12 (Pea), SEQ ID NO: 13 (Spinach), SEQ ID NO: 14, SEQ ID NO: 15 (Tobacco) and SEQ ID NO: 16 (Cuscuta) of the spacer (64 bp) region 16S-23S rDNA from several crop species with the tobacco chloroplast sequence where (+) represents the positive and (−) the negative strands, respectively.

The trnI and trnA spacer region, has been found to be highly conserved in a great variety of plant species, from cyanobacteria to higher plants, such as monocotyledonous and dicotyledonous. The trnI and trnA genes flank on each side a spacer region, referred to as spacer 2 "or 'spa 2' region" (FIG. 4F-4G). The regions on either side of the spacer region likewise have almost perfect homology with corresponding regions between species of plants from cyanobacteria to higher plants, except that the higher plants contain two introns in the trnI and trnA genes. Longer border sequences tend to favor more efficient integration of foreign DNA. Therefore, although not essential, the homology between species of the trnI and trnA genes, in addition to the homology of the spacer region, contributes to the efficiency of transformation and integration (FIG. 4A-4E).

If longer border sequences which include non-homologous portions, are incorporated into the vector, the non-homologous portion of the sequence will be "looped out" and "clipped off", in the recombination process and will not integrate into the target chloroplast genome.

Different universal vectors can be constructed with the spacer region. For instance, shorter or longer flanking sequences can be constituted with part or all of the trnA and trnI genes adjacent to spa '2'.

A preferred universal vector comprises the flanking sequences and an expression cassette which comprises the following genetic elements to provide for transcription and translation of the DNA coding sequence organized in the following order (from the 5' to the 3' ends): a 5' part of the flanking sequence, a promoter functional in chloroplast, a DNA sequence with appropriate cloning site(s) for insertion of one or more coding sequence(s) for the desired phenotype or molecule of interest, and for a selectable marker, a terminator of transcription and a 3' part of the flanking sequence. The order of the DNA sequences coding the desired phenotype and the selectable marker can be switched. Additional flanking plant DNA sequences can be provided to promote stable integration. Preferably, the flanking sequence comprises an origin of replication (ori).

In a particular illustration, the highly conserved spacer region resides in the inverted repeat of the chloroplast genome. However, the particular location of the spacer in the chloroplast genome is not as important as its high homology with the spacer region of different plants.

Further, as may be seen in FIGS. 4F-4G, the spacer 2 (or spa 2) sequence which is 64 bp long is too short to include the chloroplast genome ori which resides upstream, of that spacer. If it is desired to include the ori, a longer spacer sequence encompassing the ori will be selected which will include the spacer sequence and an additional sequence in the flanking sequences. This will provide a longer template for homologous recombination into the recipient chloroplast genome and promote homoplasmy.

Another preferred vector is one in which the flanking sequences comprise, each one, in addition to the spacer 2 region, a portion or all of the intergenic spacer region between the tRNA$^{Ile}$ and the tRNA$^{Ala}$ genes of the chloroplast genome (FIG. 4A-4E). Further, the flanking sequences may include part or all of the tRNA$^{Ile}$ and the tRNA$^{Ala}$ genes, respectively. Optionally, the flanking sequences comprise each one part or all of the 16S and/or 23S rRNA gene sequences.

Illustrative Universal Vectors. A preferred universal vector comprises a DNA sequence which comprises the sequence of the spacer 2 region between the highly conserved trnI and the trnA genes between the 16S-23S rRNA genes of the chloroplast genome. Preferably, this region comprises part or all of the DNA sequence (FIG. 4F-4G) of the trnI and the trnA genes. That region is excised from a selected plant like tobacco and subcloned into a commonly available plasmid like pUC19, e.g. at the PvuII site. Into the plasmid there is inserted the expression cassette which contains a selectable marker gene, a chloroplast 16SrRNA promoter, a gene encoding an enzyme conferring a resistance to an antibiotic like the aadA gene encoding aminoglycoside 3' adenyl transferase conferring resistance to streptomycin/spectinomycin and 3' untranslated region of the chloroplast psbA gene.

Figure 5:
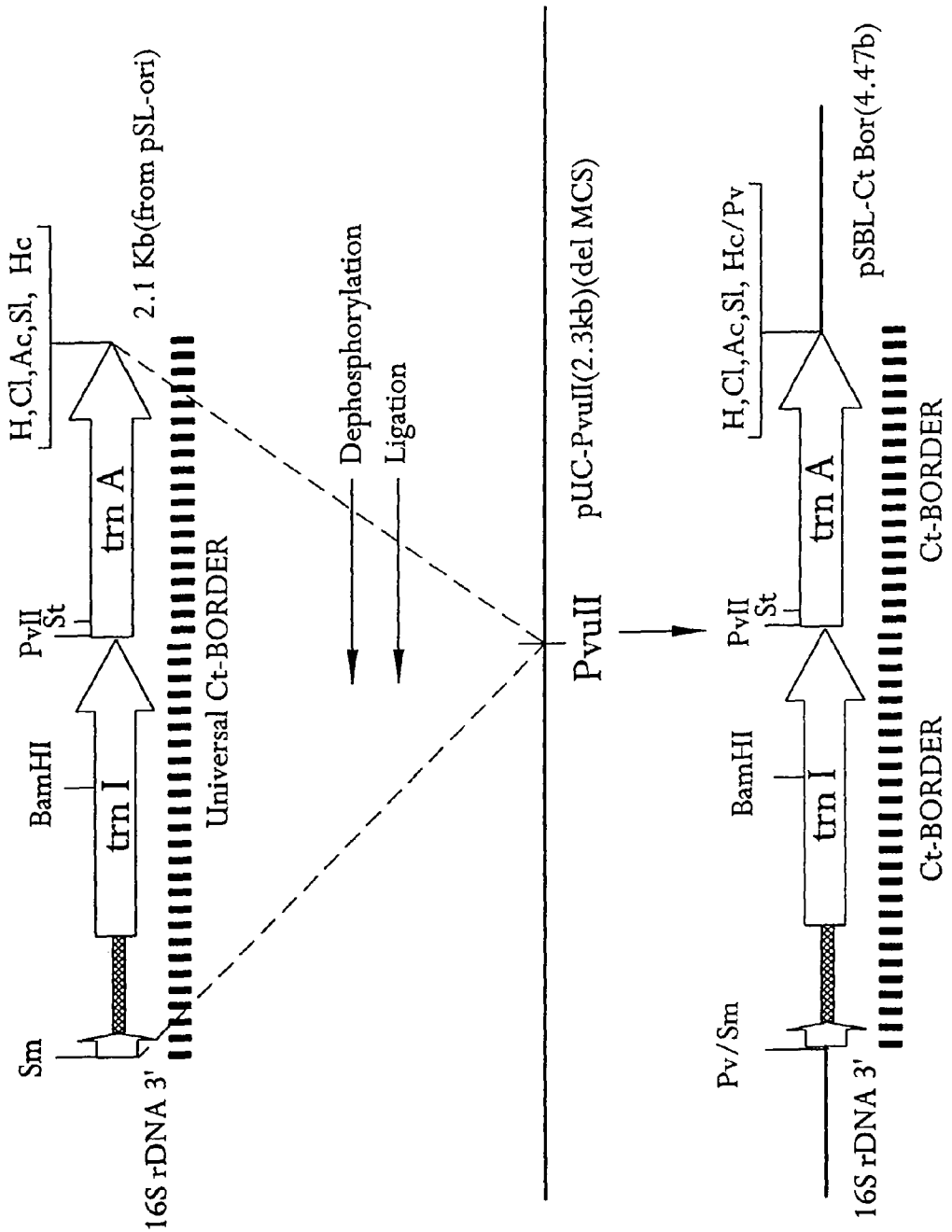
FIG. 5 shows construction of the vector pSBL-Ct border.
Figures 6A, 6B, 6C:
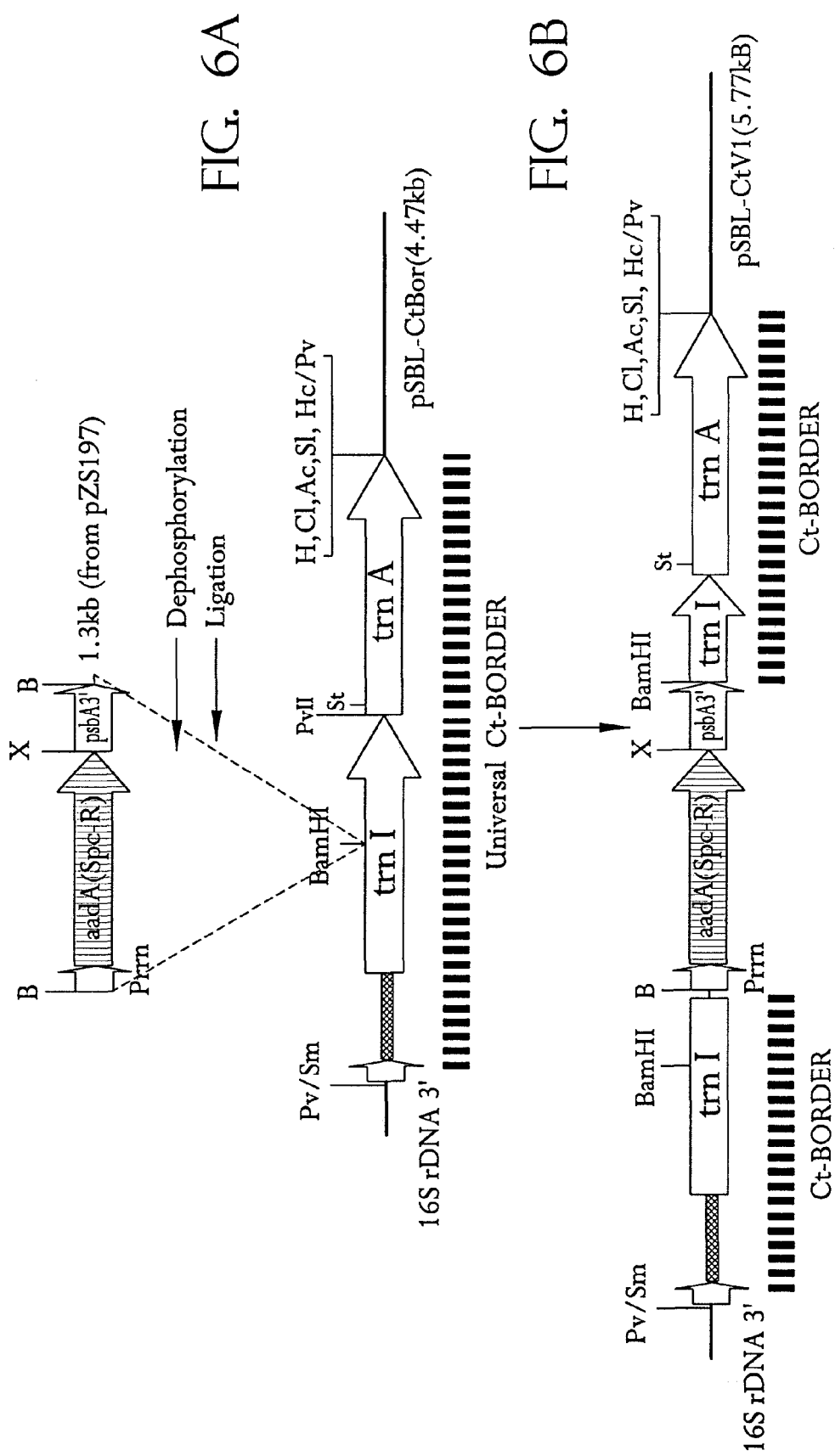
FIGS. 6A-C shows construction of the vector pSBL-CtV1 selectable marker gene cassette containing a chloroplast 16S rRNA promoter (Prrn), the aadA gene and a 3' untranslated region of the chloroplast psbA gene.
Figure 7C:
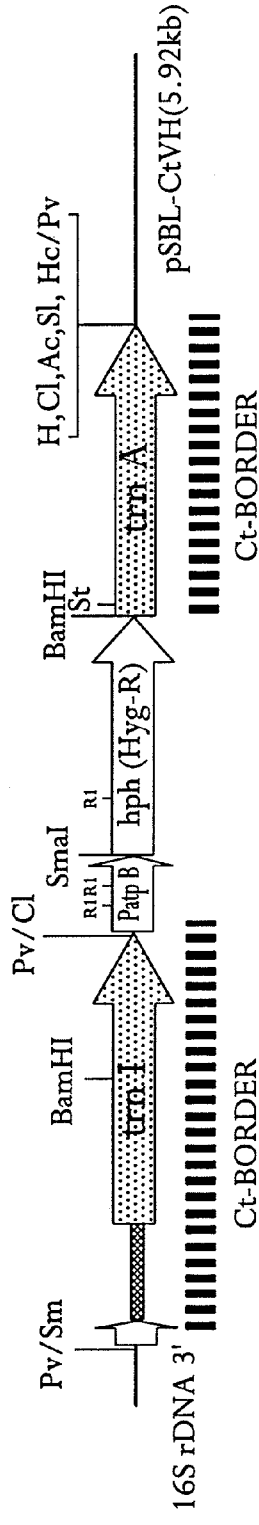

Specifically, when a universal vector is constructed with plasmid pSBL-Ct-bor (FIG. 5), a selectable marker gene cassette containing a chloroplast 16S rRNA promoter, the aadA gene encoding aminoglycoside 3'-adenyl transferase conferring resistance for streptomycin/spectinomycin, or a herbicide resistance gene and a 3' untranslated region of the chloroplast psbA gene, was inserted into the plasmid. (FIG. 6) This selectable marker gene cassette was then inserted into the universal border in two different orientations. In the vector pSBL-CtV1, the selectable marker gene cassette was inserted into the trnI gene (FIG. 6A). In the vector pSBL-CtV2 (FIG. 7A), the selectable marker gene cassette was inserted between the trnI and trnA genes in the spacer region, in the direction of the 16S rDNA transcription. In the vector pSBL-CtV2 R (map not shown), the selectable marker gene cassette was inserted between the trnI and trnA genes in the spacer region, in the direction opposite of the 16S rDNA transcription.

Several genes of interest have been inserted into the pSBL-CtV2 vector, a preferred embodiment of the universal vector. For example, the vector pSBL-CtV3 (FIG. 7B) contains the reporter gene mGFP that codes for a green fluorescent protein, isolated from jelly fish. This gene may also be useful for visible selection of transformed plants or in ornamental horticulture, for example, in ornamental crops like Christmas trees or even lawn grass, which may glow with green fluorescence upon illumination with blue light.

The vector pSBL-CtVH (FIG. 7C) contains a different selectable marker, hygromycin phosphotransferase (hph gene driven by the chloroplast atpB gene promoter), which confers resistance to the antibiotic hygromycin. This vector may be used to transform plants that are resistant to other antibiotics and is particularly useful for transforming monocots, which are generally resistant to other commonly used antibiotics. This gene may confer additional traits such as herbicide resistance, a non-targeted trait.

Figure 7D:
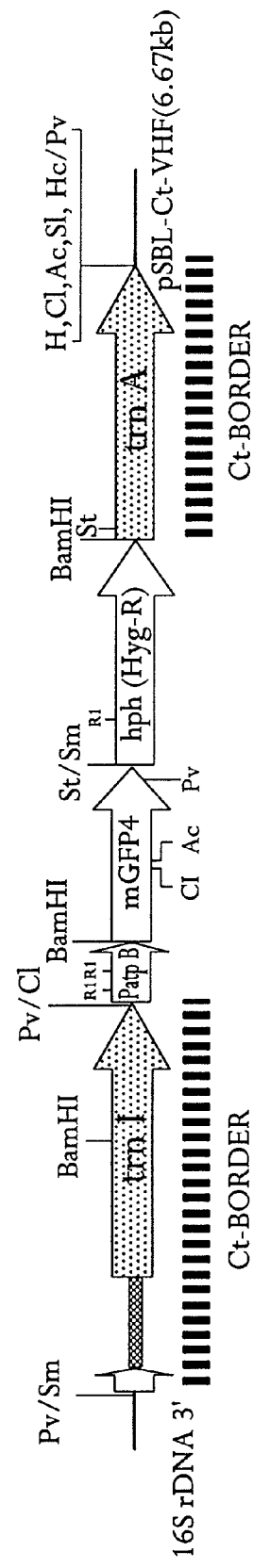

Vector pSBL-CtVHF (FIG. 7) contains the GFP and hph genes, which can be used for lethal or a combination of lethal/visible selection.

A Chloroplast Vector Specific for Tobacco and a Universal Chloroplast Vector. The tobacco chloroplast vector pZS-RD-EPSPS (FIG. 2A)("TV") and the universal vector pSBL-RD-EPSPS (FIG. 2B)("UV") contain both the Prrn promoter (of the 16S rRNA), the aadA gene (for spectinomycin selection), the mutant aroA gene that codes for the enzyme EPSPS synthase (for glyphosate selection) and the psbA 3' region. The flanking sequences in pZS-RD-EPSPS contain rbcL and orf 512 and in pSBL-RD-EPSPS contain the trnI and trnA genes facilitating integration into either the Large Single Copy region (FIG. 1 at the "TV" arrow) or the inverted repeat regions (FIG. 1 at the UV arrows) of the tobacco chloroplast genome, respectively.

Glyphosate is the active ingredient in Monsanto's herbicide ROUNDUP™ and is used as a selectable marker for herbicide selection of transgenic plants.

Construction of Chloroplast Vectors. Standard protocols for vector construction including Klenow filing the dephospphorylation, were used. The tobacco chloroplast expression vector pZS-RD-EPSPS is shown in FIG. 2A. The universal chloroplast vector PSBL-RD-EPSPS is shown in FIG. 2A. The construction of these vectors is further shown in the examples. Both plasmids were amplified in the XL1 Blue Strain of *E. coli*. Growth curves were recorded in M-9 minimal medium. Both vectors are used for selection on glyphosphate to confirm resistance to ROUNDUP™.

The chloroplast expression vector pZS-RD-EPSPS is specific for tobacco and as noted earlier is not useful to transform other plants (Maier et al., 1995). In contrast, the universal chloroplast expression and integration vector PSBL-RD-EPSPS (FIG. 2B) is competent to transform chloroplast genomes of numerous other plant species because of the universality of the vector as described above. The universal vector integrates foreign genes into the 16S-23S spacer region of the chloroplast genome. The universal vector uses the trnA and trnI genes (chloroplast transfer RNAs) coding for alanine and isoluceine) from the inverted repeat region of the chloroplast genome as flanking sequences for homologous recombination. The chloroplast border sequence used in this invention also contains the chloroplast origin of replication (oriA), as confirmed in several crop species including pea (Nielsen et al., 1993) and tobacco (Lu et al., 1996), which may explain the highly conserved sequence homology in this region. This origin of replication provides increased number of plasmid templates for efficient integration into the recipient chloroplast genome and achieve homoplasmy.

As shown above, in the construction of the universal vector, an expression cassette containing a chloroplast promoter, a selectable maker gene conferring resistance to an antibiotic (or other selected marker), a gene encoding the target molecule, and the other elements (as described herein) are inserted at a convenient restriction site into the DNA fragment containing the spacer region. If desired, the foreign gene encoding the target molecule may be inserted into the expression cassette after insertion of the cassette into the DNA fragment containing the conserved spacer region so that, before insertion, the cassette will include multiple cloning sites for insertion of one or more DNA coding sequences.

The position of the restriction site in the spacer sequence can determine the respective length of the two flanking sequences, which will be fractions (of different or same length) of the spacer region. Thus, the two flanking sequences need not be identical in length as long as each one contains enough of complementarity to the target chloroplast genome to promote homologous recombination.

Because the vector of the invention has such a high degree of homology to the spacer region of the chloroplast genomes of multiple species of plants, it is competent to transform, not only the species of plants from which the border sequence of the vector is derived, but any plant species.

As used in this specification, the term "homologous" means that a DNA sequence from one plant species possesses regions of sequence identity to portions of a DNA sequence from another plant species. That is, if two DNA sequences are highly homologous, the DNA species may have 100% sequence identity or less than 100% identity. For example, for purposes of chloroplast genome integration, a 400 bp sequence which is only 25% homologous overall, but which contains a 100 bp portion which is 85% to 90% or more homologous, is considered to be highly homologous with the chloroplast genome.

The inclusion of a chloroplast ori within the flanking sequences of the universal vector has also been shown to be beneficial. Without being bound by theory, it is believed that the presence of the ori in the universal vector promotes homoplasmy following a single round of selection, without the need for a second selection step. This is especially important in the transformation of monocotyledonous plants, such as maize or rice, in which a second selection step is not feasible due to the difficulty of growing these plants in culture from leaf cuttings with the resultant need to grow these plants from embryos. If an ori is desired but is lacking, it may be introduced into a flanking sequence or elsewhere. If it is desired to increase the copy number of the introduced universal vector, a chloroplast DNA fragment containing an ori will be inserted outside the flanking sequences so that it will function only to amplify the copy number of the universal vector and does not become integrated into the chloroplast genome.

As opposed to being derived from a specific plant, the flanking sequences can be derived from a spacer region synthetically made as shown below.

For transcription and translation of the DNA sequence encoding the polypeptide of interest, the entire promoter region from a gene capable of expression in the chloroplast generally is used. The promoter region may include promoters obtainable from chloroplast genes, such as the psbA gene from spinach or pea, the rbcL and atpB promoter region from maize and rRNA promoters. Competent promoters are also described and other literature sources are identified in U.S. Pat. No. 5,693,507.

The flanking sequences shown by U.S. Pat. No. 5,693,507 and the other publications to promote stable integration are not the flanking sequences of the universal expression and integration vector described herein which are highly conserved from plant species to plant species, whereas the flanking sequences of that patent and the other publications are not.

Identification of Intergenic Spacer Sequences. The invention provides methods to identify appropriate untranscribed intergenic spacer sequences in plants which are appropriate to construct the universal vectors. The method comprises isolating plastid genomic DNA, carrying out hybridization with a radioactive labeled probe of a known spacer, detecting and isolating plastid sequences which exhibit the desired degree of homology with the probe. As an illustration, to determine if a plastid genome of unknown structure and sequence possesses the spacer region, Southern blots utilizing the tobacco spacer region as a probe are carried out. Plastid genomic DNA is isolated and cleaved by an appropriate restriction enzyme according to established procedures. Hybridization with the spacer probe is conducted under both stringent (e.g., 50% formamide at 68° C., wash in 0.1×SSC at 68° C.) and non-stringent condition (e.g., 6×SSC, at 68° C., wash in 2×SSC at 50° C.)(1×SSC is 0.15M NaCl, 0.015M sodium citrate) to detect plastid sequences exhibiting approximately 90-100% homology or 60-100% to the tobacco spacer, respectively. The identified plastid sequences are then isolated. If one's requirement of homologous recombination is more permissive, a lower degree of hybridization to the probe, such about 60% can be satisfactory.

Thus, any known or unknown spacer region of sufficient homology for recombination is suitable for the construction of the UV. Likewise, the known sequence of any intergenic highly conserved spacer sequence may be used to identify and isolate plastid sequences which are homologous to a known spacer sequence.

Alternately, the BLAST program as described hereinabove can be used to identify highly conserved regions in plastid genomes of which the sequences are known.

Plants that can be Transformed. Plants which may be transformed by the universal vector of the invention include any lower plants, such as cyanobacteria, any higher plants, such as monocotyledonous and dicotyledonous plant species. The plants to be transformed can be solonacious plants or plants that grow underground. A non-exclusive list of examples of higher plants which may be transformed with the universal vector includes cereals such as barley, corn, oat, rice, and wheat, melons such as cucumber, muskmelon, and watermelon; legumes such as bean, cowpea, pea, peanut; oil crops such as canola and soybean; solanaceous plants such as tobacco, tuber crops such as potato and sweet potato, and vegetables like tomato, pepper and radish; fruits such as pear, grape, peach, plum, banana, apple, and strawberry; fiber crops like the *Gossypium* genus such as cotton, flax and hemp; and other plants such as beet, cotton, coffee, radish, commercial flowering plants, such as carnation and roses; grasses, such as sugar cane or turfgrass; evergreen trees such as fir, spruce, and pine, and deciduous trees, such as maple and oak. Of greatest present interest are the major economically important crops like maize, rice, soybean, wheat and cotton. None of these plants to the inventor's knowledge, other than tobacco, has ever been stably transformed via the chloroplast genome, and none, including tobacco, have been stably transformed by a universal vector, as described herein. A plant from which the DNA sequence is frequently obtained is tobacco because it is the most thoroughly characterized plant, but any other plant chloroplast genome is suitable.

It will be recalled as described above that the vector used to stably transform tobacco was not competent to transform the chloroplast genome of other plants.

Method for Transformation. The expression cassettes may be transformed into a plant cell of interest by any of a number of known methods. These methods include, for example, the following. Transformation by tungsten particle bombardment, polyethylene-glycol-mediated transformation, use of a laser beam, electroporation, microinjection or any other method capable of introducing DNA into a chloroplast. See, for example, Sanford, 1988; Daniell, 1993; Daniell, 1997; U.S. Pat. No. 5,693,507; Kin Ying et al., 1996. The use of these techniques permits the application of the invention described herein to a wide variety of both monocotyledonous and dicotyledonous plants.

Expression of Non-Plant Molecules from Transformed Plants

The increased usefulness of the universal expression integration vector of the invention is clearly shown by the competency of the vector to generate transformed plants to express non-plant and valuable molecules.

Biodegradable Protein-Based Polymers. In accordance with another embodiment of the invention, the universal vector has been used to transform tobacco with a synthetic gene expressing protein-based polymers (PBPs). Such polymers, and the genes expressing them, are known in the literature. (Daniell, et al. 1997). Of particular interest, are protein-based polymers (PBP) which have repeating pentamer sequences like GVGVP (Yeh et al., 1987). These PBP polymers show useful inverse-phase temperature transition property. The protein become insoluble when the temperature is raised above the transition state. PBPs offer a wide range of materials similar to that of the petroleum-based polymers, such as hydrogels, elastomers, and plastics. They also show remarkable biocompatibility, thereby enabling a whole range of medical applications including the prevention of post-surgical adhesions, tissue reconstruction and programmed drug delivery (Urry et al., 1993). On the non-medical side, potential applications include use in transducers, molecular machines, superabsorbents and biodegradable plastics (Daniell et al., 1997). Such polymers include the polymer $(Val'-Pro^2-Glv^3-Val^4-Pro)_n$ $(VPGVP)_n$ SEQ ID NO: 18 wherein "n" can vary from 1 to units in the hundreds, like 250 or their analogs. Important commercial possibility and related aspects are discussed by Daniell, 1995. Useful biodegradable plastics are made from PBPs. The genes experiencing these PBPs are also useful in the invention in that they can be used as carries, i.e. the gene of a molecule of interest can be fused to the PBP gene of chloroplast integration and expression.

In a prior study, the synthetic polymer gene coding for $(GVGVP)_{121}$ SEQ ID NO: 17 was hyperexpressed in *E. coli* to the extent that polymer inclusion bodies occupied nearly 80-90% of the cell volume (Guda et al. 1951; Daniell et al. 1971). The same gene was also expressed in the nuclear compartment of cultured tobacco cells (Zhang et al., 1995) and leaves of transgenic tobacco plants (Zhang et al.), 1996)

In a model system, the intergenic region of the trnI and the trnA genes in the 16S-23S rRNA spacer region of the tobacco genome (FIG. 1) was used to construct an universal vector for integration of the selectable marker gene aadA gene and the synthetic polymer gene (EG121). The vector was inserted into the inverted repeat region of the chloroplast genome. Transformed tobacco plants expressed high level of the polymer protein. Chloroplast genome of other plant species, are also transformable with the synthetic gene to express the protein-based polymer, using the universal vector.

Production of High Value Molecules. The studies with the biopolymer have shown that a non-plant product can be expressed by a synthetic gene, thus making it possible by means of the vectors of the invention to express biologically valuable molecules from transformed plants with a great variety of DNA coding sequences. The DNA coding sequence will be comprised in a universal vector, or, if desired, in an expression cassette, as described above.

Transgenic plants are known to produce valuable biologically active molecules by nuclear transformation but not via chloroplast transformation. See the following literature references, all of which are incorporated by reference. Daniell, 1995; Miele, 1997; Lyons, 1996; Daniell, and Guda, 1997; Arntzen, 1997.

Expression of Biologically Active Molecules. Plants transformed in accordance with the invention with the universal vector or with the expression cassette can be made to express valuable biologically active molecules in chloroplast containing parts of the plants. The plants will then be harvested by known practices. The transformed plants containing these products can thus be administered orally. Arntzen, 1997. Production of pharmaceuticals by transgenic plants has been performed with peptides (proteins) for many pharmaceutical applications, including vaccines, immunomodulators, growth factors, hormones, blood proteins, inhibitors, and enzymes. Typical transgenic plant derived biologicals which have been reported, include vaccines against viral diseases; viral peptide epitopes, like human immunodeficiency virus, non-viral peptide epitopes, bacterial antigenic proteins; bioactive peptides, recombinant toxins, plantibodies (recombinant antibodies), serum proteins, and plant secondary metabolites. All these products can be expressed in chloroplasts of transgenic plants in accordance with the invention.

Typical pharmaceutical peptides or proteins produced in transgenic plants include hepatitis B surface antigen, norwalk virus capsid protein, foot-and-mouth disease virus, human rhinovirus 14, human immunodeficiency virus, S. mutans surface protein, E. coli enterotoxin, B subunit, malarial circumsporozoite epitopes, mouse ZP3 protein epitope (vaccine); mouse catalytic antibody 6D4, mouse mAB Guy's 13, mAB B1-8, anti-phytochrome Fv protein, anti-substance P (antibody); human serum albumin (HSA), human protein C (serum protein); α-trichosanthin, ricin (cytotoxin); human epidermal growth factor (growth factor); leu-enkephalin (neuropeptide) and human acid β-glucosidase (hGC)(enzyme). Many of these molecules have been expressed in tobacco, potato tubers, etc.

Of particular interest, in accordance with the invention is the production of insulin and human serum albumin (HSA) with the universal integration and expression vector or with an expression vector. The HSA has already been produced in transgenic (nuclear) potato and tobacco plants. Sijmons et al, 1990. The aforementioned products can be produced via chloroplast transformation in accordance with the invention.

Insulin. The invention provides a method for expressing insulin as a polymer-fusion protein from a transformed plant. The plant may be transformed with an expression cassette or with the universal integration and expression vector which comprises a synthetic biopolymer gene, line $(GVGVP)_{40}$ SEQ ID NO: 17. A suitable plant is tobacco because of the ease of genetic engineering and the need to find alternative uses of this controversial corp.

For expression in bacteria, the method comprises constructing a vector for expression in E. coli as a polymer $(GVGVP)_{40}$ SEQ ID NO: 17 gene fusion with a pro-insulin gene, expressing the polymer-insulin fusion proteins in E. coli, (grown in a known manner), purifying the recombinant protein utilizing the temperature-transition properties of the protein-based polymer, and cleaving the insulin from the polymer using well known methods.

For plant transformation, an expression cassette or the universal integration and expression vector, which comprises the polymer gene fusion with the pro-insulin gene, is introduced into a target plant, like tobacco. The polymer-insulin fusion protein is expressed from the plant, the polymer fusion protein is extracted from the chloroplast and the cytosol compartments of the plant cells, the insulin is cleaved from the polymer protein with dithiothreitol (DTT) or the other known methods, and the insulin is collected. Alternatively, insulin polymer fusion product can be expressed in an edible crop or edible parts of the crop.

The technique of fusing a DNA sequence coding for a molecule of biological activity to a synthetic gene expressing a protein-based polymer for expressing, in a suitable bacterial or yeast host or a transformed plant, is a highly promising method of wide applicability.

Recombinant Human Serum Albumin in Plants. In nuclear transgenic tobacco and potato plants, recombinant human serum albumin (rHSA) that is indistinguishable from the authentic human protein has been produced (Sijmons et al., 1990). This showed the expression of a valuable protein in transgenic plants, but also that it was possible to achieve proper processing by fusion of HSA to a plant pro-sequence that resulted in cleavage and secretion of the correct protein. The chloroplast genome of a selected plant like tobacco can be readily transformed with a universal vector as described herein and made to express HSA.

General Applicability. As described herein the universal vector permits, in accordance with the invention, the transformation of plants, make the plant to express a biological molecule which can impart a desired phenotype to the plant and/or produce a desired product which may, but need not have biological activity (or a precursor to a final product). The coding nucleotide sequence can be synthetic, or natural. The produced molecule can be foreign to the plants, non-functional in the plant or functional. The universal vector has broad applications in the domain of plant transformation.

It is contemplated that any biologically active molecule (precursor or derivative thereof) can be produced by transgenic plant transformed with the universal vector of the invention, with suitable adaptations as may be required for a particular case.

Herbicide Tolerance of Chloroplast Transformed Plants

Another embodiment of the invention relates to the use of the universal vector to confer herbicide resistance or tolerance to plants. The advancement of gene transfer technology has made possible the introduction of herbicide resistance genes into plants, thereby making the herbicide selective for a particular crop.

Modifications of the Target Enzyme. The first step towards this approach is the identification and necessary modification of the target enzyme (gene) of the herbicide to confer tolerance, which has been performed quite extensively. Sulfometuron methyl is a sulfonylurea herbicide that blocks the growth of bacteria, yeast, and higher plants by inhibiting the first enzyme of the branched chain amino acids pathway, acetolactate synthase (ALS). Mutant genes for ALS were isolated from E. coli and yeast that confer resistance to sulfometuron methyl. Yadav, et al. (1986). Herbicide resistance in tobacco, and several other crops has been achieved by genetic engineering of the ALS gene. Gabard, et al. (1989); Miki, et al. (1990). Yet another approach to engineer herbicide resistance in plants has been the expression of the enzyme phosphinothricin acetyl transferase (PAT) that detoxifies the herbicide phosphinothricin. DeBlock, et al. (1987).

Glyphosate. Glyphosate is a potent, broad spectrum herbicide which is highly effective against annual and perennial grasses and broad leaf weeds. Glyphosate is environmentally safe as it rapidly degrades in soil, has minimal soil mobility, and has very little toxicity to non-plant life forms. Glyphosate works by binding to and inhibiting the enzyme 5-enol-pyruvyl shikimate-3-phosphate (EPSP) synthase. EPSP synthase (EPSPS) catalyzes the formation of EPSP, which is important in the aromatic amino acid biosynthesis pathway, from shikimate-3-phosphate and inorganic phosphate. The non-toxicity of glyphosate to animals is due to the fact that this reaction occurs only in plants and microorganisms. Unfortunately, because the reaction to form EPSP occurs in all plants, glyphosate does not have selectivity between weeds and desirable plants such as crops and ornamentals.

Two approaches have been used to attempt to develop a glyphosate resistant plant by genetic engineering. One approach is based upon overproduction of wild type EPSP synthase, so that after competitive inhibition of EPSP synthase by glyphosate, the residual EPSP synthase confers glyphosate tolerance. The second approach is based upon the expression of a mutant gene (aroA) encoding glyphosate resistant EPSP synthase.

In all of the aforementioned examples, without exception, herbicide resistant genes have been introduced into the nuclear genome.

The Need for Chloroplast Transformation. A serious need exists, to develop a herbicide resistant plant, particularly a plant resistant to the most widely used herbicides, in which the protein conferring herbicide resistance is produced in the chloroplast, and in which the gene conferring herbicide resistance cannot escape by pollen to the environment.

The universal vector of the invention responds to this need by transformation of any target plant to provide tolerance to any selected herbicide like to glyphosate. Important commercial crops like wheat, rice, corn (maize), soybean can be made resistant to a selected herbicide by means of the universal vector.

The invention provides a transgenic herbicide resistant plant in which a foreign transgene conferring resistance to one or more herbicide is integrated into the chloroplast genome by means of the universal vector. The transgenic plant may be a mature plant, an immature plant, such as a seedling, an embryo, a callus, a cultured tissue, or cell suspension, or a portion of a plant such as a cutting or a callus. Herbicides which are suitable for the invention and for which genes conferring resistance may be stably integrated into the chloroplast genome in accordance with the invention include all known (and also to be developed) herbicides.

Class of Herbicides. Herbicides controllable by the invention have been generally grouped into several chemical classes.

A first class includes the PSII (Photosystem II) herbicides which interfere with the reduction of plastoquinone on the acceptor site of PSII which include such chemicals as triazines, triazinones, urea derivatives, biscarmates, nitrites, nitrophenols, substituted pyridazinones, phenylcarbamates, anilides, cyanoacrylate, DCMU, carboanilides, uracils, specifically for example, dichlorophenyldimethylurea, atrazine, metribuzine, lenacil, phenmedipham, ioxynil and dinoseb. These chemicals bind to a 32-kDa binding protein ($Q_B$ protein, D1, herbicide-binding protein) in the thylakoid membrane of chloroplasts, thereby blocking photosynthetic electron transport. The plastid gene which codes for a precursor of the $Q_B$ protein is named psbA, the sequences of which show a very high degree of homology in different plants. The most important PSII herbicide is atrazine, developed by Ciba-Gergy.

Another class are the PSI (Photosystem I) herbicides, a membrane bound protein complex which catalyzes the light-driven oxidation of plastocyanin (PC) and reduction of ferredoxin (Fd). Typical of these chemicals are the bipyridyl herbicides paraquat and diquat.

Another class of herbicides are the aryloxyphenoxypropanoates (APP) or acetyl coenzyme A carboxylase type herbicides, which inhibits acetyl-CoA carboxylase and subsequent fatty acid biosynthesis in plastids. Typical of the APPs are cyclohexanedione (CHD), sethoxydin, haloxyfop, quizalofop, phenoxaprop (and the lower alkyl-substituted molecules thereof), dicolofop, sethoxydin, clethodin and tralkoxydim.

Yet another class of herbicides includes the auxin analogs like macropop, chloramben, dicamba, benazolin, 1-naphthylacetic acid; 3,6-dichloropicolonic acid, picloram, fluoroxypyr, quinclorac, MCPA and 2,4-D.

An additional class are the mitotic herbicides, termed dinitroaniline herbicides, like trifluralin, oryzalin and pendimethalin.

Another chemical class of herbicides to which the invention applies are those acting in the biosynthesis of amino acids, such as tertiary the amino methyl phosphonic acids chlorsulfuron, glufosine and glyphosate.

Another class of herbicides are the acetolactate synthase-inhibiting herbicides (ALS), like the sulfonylureas, imidazolinones, triazolopyrimidines and pyrimidinyl thiobenzoates, such as chlorsulfuron, imazaphyr, flumetsulam (and others listed in chapter 4, Table I of Herbicide Resistance in Plants, 1994, cited below).

Examples of sulfonylurea herbicides are sulfometuron methyl (the active ingredient of Oust™) and chlorsulfuron (the active ingredient of Glean™). Imazapyr, one of the imidazolinones, is the active ingredient of American Cyanamid's herbicide Arsenal™ and imazamethabenz is a mixture of two imidazolinones (Merk Index, 11th Ed. 4825). Mutated forms of ALS located in the structural genes of ALS, ilvG and ILV2 may be used to confer herbicide resistance using the universal vector.

In spite of the chemical differences between the imidazolinones and sulfonylureas, these substances inhibit the same enzyme, ALS. It appears that quinones and an imidazolinone herbicide compete with a sulfonylurea herbicide for a common site on ALS. Accordingly, in accordance with the invention, plants can be transformed which will show a resistance to both groups of these and other herbicides.

Another group of chemicals controllable by the invention using the universal vector which has herbicidal activity is typified by L-phosphinothricin, which is a component of the tripeptide "bialaphos". This tripeptide is marketed under the trade name "Herbiace™" by Meiji Seika, Japan, and as "Basta™" by Hoechst AG, Germany. L-Phosphinothricin is a potent inhibitor of glutamine synthetase, which causes a rapid increase of ammonia concentration plants and leads to the death of the plant cell.

In spite of extensive studies, no satisfactory product has been developed to impart herbicide tolerance to plants by chloroplast transformation. With the glyphosate type herbicide, it has been reported that regenerated nucleus transformed transgenic plants showed tolerance to glyphosate, but also showed impaired growth, and have not resulted in transgenic plants with high level of tolerance to glyphosate, Schultz, et al., 1990.

Chloroplast Transformants. In accordance with the invention, the chloroplast of target plants that are susceptible to herbicides is transformed with a vector of the invention carrying the necessary coding sequence, thereby conferring herbicide resistance. The transformed chloroplast comprises a genome which carries a foreign transgene which confers the herbicide tolerance. The chloroplast may be a mature chloroplast or may be an immature chloroplast, such as an etioplast. Preferably, the gene conferring herbicide resistance codes for EPSP synthase which binds less readily (has reduced affinity) to glyphosate than does wild type the EPSP synthase. If present, the second transgene is generally a gene which confers antibiotic resistance to the plant. Thus, the herbicide resistance can be used by way of lethal selection as a marker for chloroplast transformation by selection of the transformants by exposure to a medium with lethal concentration of the selected herbicide, to which the transformants will survive.

The origin of the second gene can be procaryotic (for example, bacterial) or eucaryotic (for example, plant).

The invention also relates to produce a plant resistant to several herbicides, whether of the same class of herbicide or of different classes of herbicides, and the transformed plant resistant to multiple herbicides.

Some plant species are known to have a developed a natural and non-permanent tolerance to certain types of herbicides. The teaching of this invention is readily applicable thereto.

The invention includes a method for producing a herbicide resistant plant which comprises transforming the chloroplast of the plant by introducing one or more foreign transgenes which code for a protein conferring herbicide resistance to the genome of the chloroplast of the plant. Preferably, the transgene codes for a mutant form of the enzyme which has decreased affinity for a given herbicide than does the naturally occurring enzyme.

The following Table lists a variety of type of resistance determinants, (chemicals or "molecules") which inhibit or which confer resistance, and typical herbicides related thereto.

TABLE I

| RESISTANCE DETERMINANT | HERBICIDES |
|---|---|
| glutathione S-transferase | s-triazine |
| | simazine |
| | chloracetamide |
| | metalachlor |
| Auxin analogs | 2,4-D |
| | MCPA |
| | mecopop |
| | chloramben |
| EPSP synthase | glyphosate |
| $Q_b$ (psbA) - PS II Type | atrazine |
| | terbutyne |
| | dichloropheny- |
| | dimethylurea |
| | metribuzine |
| | lenacil |
| | phenmedipham |
| | loxynil |
| | dinoseb |
| Acetohydroxyacid sythase (ALS) | sulfonylureas |
| | chlorosulfuron |
| | imazapyr |
| | sulfometuron |
| | methyl |
| | imidazolinones |
| Glutamine synthase | phosphinothricin |
| PS I Type | paraquat |
| | diquat |
| Acetyl coenzyme A carboxylase inhibiting enzymes (APP Type) | aryloxyphenoxypropanoate (APR), cyclohexanedione |
| Mitotic disrupters | trifluralin, oryzalin, pendimethalin, dinitroaniline |

For a comprehensive review on the topic of herbicide resistance in plants, see Herbicide Resistance Crops, Agricultural, Environmental, Economic, Regulatory and Technical Aspects, 1996, CRC Press, Inc., Editor, Stephen O. Duke and Herbicide Resistance in Plants, Biology and Biochemistry, 1994, CRC, Press, Edited by Stephen B. Powles and Joseph A. M. Holtum. In the first of these reference books, Chapter 3 on Techniques for Producing Resistant Crops (and the numerous references cited therein) is of particular interest as background to the invention. Both books are incorporated herein by reference in their entirety.

In accordance with the invention it has also been discovered that in the process for expressing a target trait another trait can be expressed by the transformed plant which may be quite desirable, indeed may be more desirable than the initially target trait. In those situations, the plants will be allowed to express and will be selected on the basis of that other trait.

The invention is exemplified in the following non-limiting examples.

EXAMPLE 1

Universal Chloroplast Integration and Expression Vectors

Figure 1:
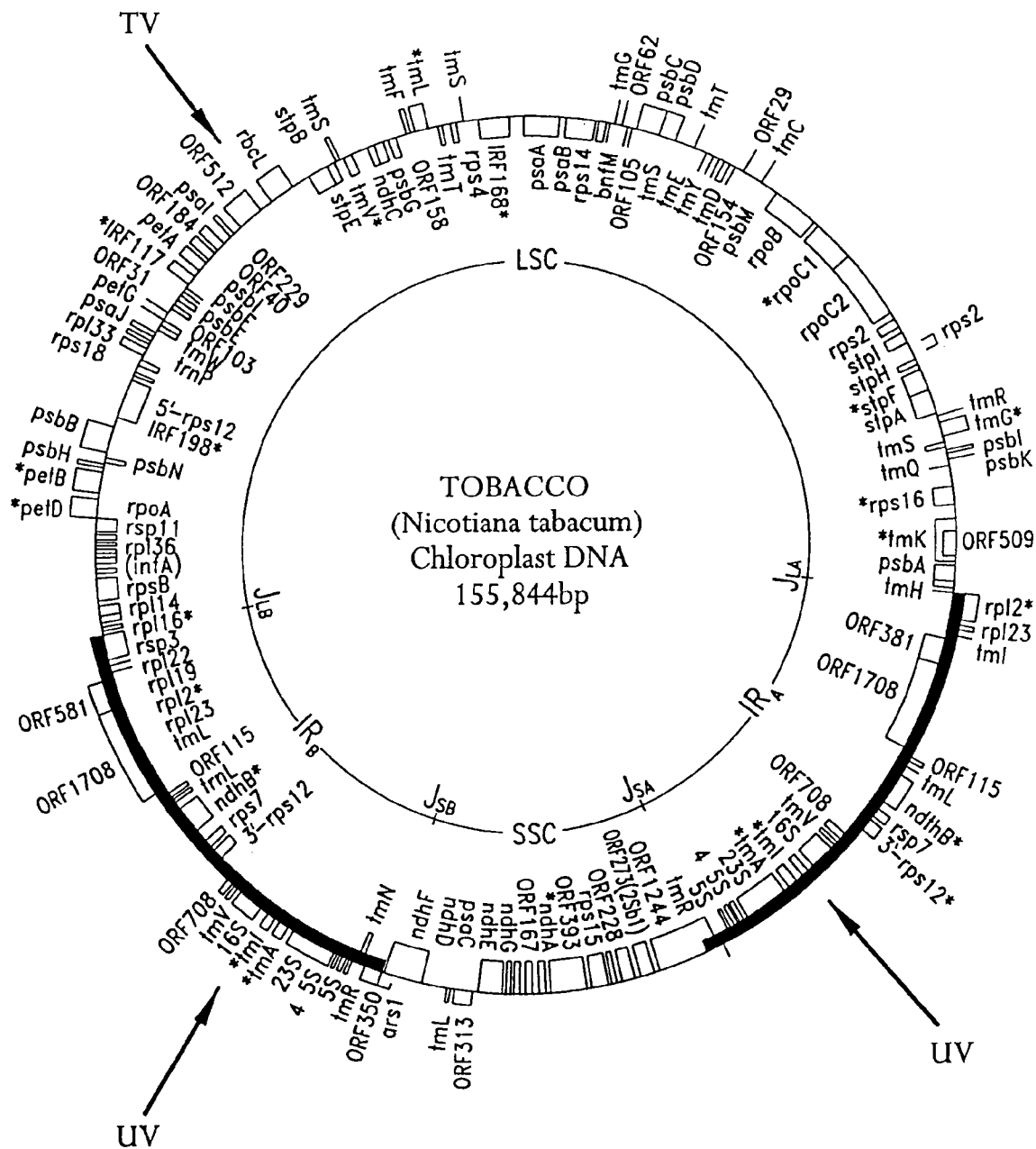
FIG. 1 shows a map of the tobacco chloroplast genome. The thick lines in the genome map represent the inverted repeat regions of the chloroplast genome. The arrows labeled "UV" represent the insertion sequences for the preferred embodiment of the universal integration and expression vector (UV); the arrow labelled "TV" represents the insertion sequence for the tobacco vector (TV).

Tobacco. Exemplary universal chloroplast vectors were constructed by first cutting out the tobacco chloroplast DNA BamHI fragment (130656-140992) containing the 16S and 23S rRNA genes and subcloning it into a commonly available bacterial plasmid pUC19. A map of the tobacco chloroplast genome is shown in FIG. 1. A 2.1 kbp HindIII-EcoRI fragment present within this fragment, containing a universal border sequence comprising trnI and trnA genes, including the spacer region between the genes, was subcloned into the pUC19 plasmid at the PvuII site. The resultant plasmid was designated pSBL-Ct Bor (FIG. 5).

The vector pSBL-RD-EPSPS (FIG. 2B) contains a mutant EPSP synthase gene that codes for the enzyme EPSP synthase. Glyphosate, the active ingredient in Mosanto's ROUND UP™, binds to the protein EPSP-synthase and blocks the synthesis of essential amino acids, resulting in death of a plant. The EPSP synthase coded for by the mutant gene does not bind glyphosate, and therefore confers herbicide resistance to crop plants.

Other genes, such as those that confer resistance to adverse environmental factors such as salt/drought tolerance (osmotolerance genes such as betaine aldehyde dehydrogenase, (BADH), for the overproduction of glycine betaine) or thermotolerance (genes coding for heat shock proteins) or cold shock tolerance proteins, or to pathogen resistance, such as antimicrobial (lytic peptides, chitinase) or antiviral (coat proteins) can be inserted singly or in non-conflicting combinations into the universal chloroplast vector, or into different cassettes of the same universal chloroplast vector to transform the target plant into one with the desired trait.

Construction of a Universal Chloroplast Integration

Vector Containing a Synthetic Spacer 2 Region

A universal chloroplast vector containing only the spacer 2 region of the tobacco chloroplast genome was constructed by first subcloning a synthetic oligonucleotide comprising the spacer 2 region into the bacterial plasmid pUC19. The positive and negative strands of the 64 base pair spacer sequence were synthesized, the sequence of the positive strand was as follows:

5'-GCTGCGCCAGGGAAAAGAATAGAAGAAGCATCTGACTACTTCATGC
ATGCTCCACTTGGCTCGG-3' SEQ ID NO: 5

The synthetic fragments were mixed and allowed to anneal, then ligated into pUC19 at the PvuII site. (FIG. 5B) Insertion of an appropriate selectable marker gene and a heterologous gene were as described above for pSBL-CtBor. (FIG. 5C)

To prepare a longer sequence which includes the tRNA$^{Ile}$ and the tRNA$^{Ala}$ genes, the same methodology is followed.

Transformation of Different Plants

EXAMPLE 2

Chloroplast Transformation of Tobacco. The following example describes a classic protocol for transformation of tobacco chloroplast for which any vector can be used. Two such vectors are identified below. All new chloroplast vectors were first tested in tobacco as described in Daniell, (1997). Tobacco (Nicotiana tabacum var. Petit Havana) plants were grown aseptically by germination of seeds on MSO medium containing MS salts (4.3 g/liter), B5 vitamin mixture (myo-inositol, 100 mg/liter; thiamine-HCl, 10 mg/liter; nicotinic acid, 1 mg/liter; pyridoxine-HCl, 1 mg/liter), sucrose (30 g/liter) and phytagar (6 g/liter) at pH 5.8. Fully expanded green leaves of about two month old plants were selected for bombardment.

Leaves were placed abaxial side up on a Whatman No. 1 filter paper laying on RMOP* medium in standard Petri plates (100×15 mm) for bombardment. Tungsten (1 µm) or Gold (0.6 µm) microprojectiles were coated with plasmid DNA, of interest (e.g. PSBL-RD-EPSPS or pZS-RD-EPSPS) and bombardments were carried out with the biolistic device PDS1000/He (Bio-Rad) as described by Daniell, 1997. Following bombardment, petri plates were sealed with parafilm and incubated at 24° C. under 12 h photoperiod. Two days after bombardment, leaves were chopped into small pieces of about 5 mm² in size and placed on the lethal selection medium (RMOP containing a selectable marker such as about 500 µg/ml of spectinomycin dihydrochloride) with abaxial side touching the medium in deep (100×25 mm) petri plates (about 10 pieces per plate). Selected from the shoots that died, the regenerated spectinomycin resistant shoots were chopped into small pieces (about 2 mm²) and subcloned into fresh deep petri plates (about 5 pieces per plate) containing the same lethal selection medium. Resistant shoots from the second culture cycle were transferred to rooting medium (MSO medium supplemented with IBA, 1 Ag/liter and an appropriate antibiotic like 500 µg/ml of spectinomycin dihydrochloride). Rooted plants were transferred to soil and grown at 26° C. under continuous lighting conditions for further analysis.

After transfer to the lethal selection medium, the explants gradually became pale and in about 3-8 weeks, green calli and shoots developed from the bombarded side of the 0leaf. Resistant shoots from each callus were considered as a clone.

PCR screening for chloroplast transformants after the first culture cycle showed that 12 out of 20 resistant clones integrate the foreign genes like the aadA gene linked to the EG121 gene into the chloroplast genome. These 12 clones were advanced to further steps of regeneration. The entire process of regeneration, starting from bombardment until transfer to soil, takes about 3-5 months.

Figure 9:
FIG. 9 shows transformed and untransformed tobacco plants growing in the presence of spectinomycin indicating non-lethal selection on the medium (500 µg/ml). Note growth of transformed (bleached) and untransformed leaves (green).

FIG. 9 shows transformed and untransformed tobacco plastids growing in the presence of spectinomycin indicating non-lethal selection on the medium (500 µg/ml).

EXAMPLE 3

Figure 10A:
FIGS. 10A-G show corn plastid transformation and regeneration.
Figure 10B:
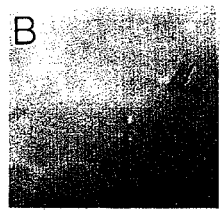

Corn Chloroplast Transformation. Surface sterilization and germination of corn seeds. Corn seeds are surface sterilized in a solution containing 20' (v/v) commercial bleach and 0.5% SDS for 15 min under continuous shaking, then serially rinsed in sterile double-distilled water (sddw) four to five times. Liquid MS-based germination medium (modified CSG) containing MS salts (4.3 g/l), sucrose (30 g/l), DM-vitamins (1.0 mg/l thiamine-HCl, 0.5 mg/l nicotinic acid, 0.5 mg/l pyridoxine-HCl and 100 mg/l myo-inositol) and BA (2.0 mg/l) at pH 5.8 is dispensed per Magenta™ box (45 ml) containing eight layers of cheesecloth, then autoclaved. Seeds are placed in modified CSG (25 seeds of any genotype per box) and cultured for three days (16 h or continuous light; 25 C) for germination. Nodal sections are excised aseptically from three day-old seedlings. The nodal section appears as a clear demarcation on the germinating seedling and represents the seventh node (FIG. 10A). When excised, the nodal cross-sections are approximately 1.2-1.5 mm in length (FIG. 10B).

FIGS. 10A-G shows corn plastid transformation and regeneration scheme. A) Three day-old corn seedling; arrows and line depict the seventh node for explant excission; B) Nodal cross sections prior to bombardment; arrows depict margin of one section; C) GUS-positive nodal section (nuclear transformation); histochemical assay conducted three days post-bombardment; D) Multiple shoot induction from one nodal section (control) after eight weeks in culture; E) Control shoot on elongation medium for three weeks; F) Rooted control plantlet; G) Selection of plastid transformed corn in liquid medium containing spectinomycin and streptomycin for eight weeks.

Figure 10C:
Figure 10D:
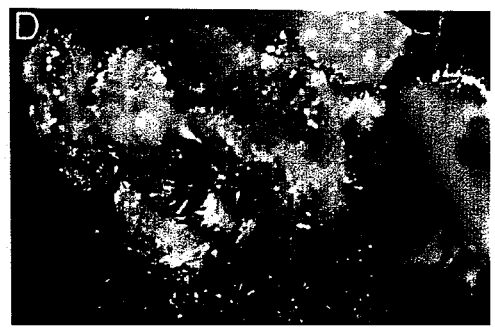
Figure 10E:
Figure 10F:
Figure 10G:
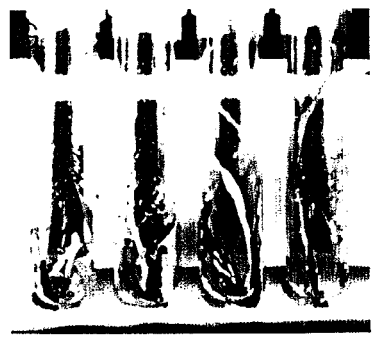

Multiple shoot induction: Nodal section explants are placed on corn shoot induction medium [CSI; MS salts, sucrose and DM-vitamins as above, BA (2.0 mg/l), CPA (0.25 mg/l) and phytagar (8 g/l) at pH 5.8], acropetal end up, and placed under the culture conditions previously mentioned. In all media except modified CSG and RG1 (rice), PGRs and antibiotics are filter-sterilized and added after autoclaving. Tissues are subcultured every two weeks onto fresh CSI medium for multiple shoot formation (FIG. 10D). Adventitious shoots are separated from the shoot clumps after eight weeks of culture and elongated on semi-solid MS-based medium containing sucrose, DM-vitamins, glycine (10 mg/l) and asparagine (150 mg/l) at pH 5.8, for three weeks (FIG. 10E). The plantlets are rooted (FIG. 10F) on the same medium containing IBA (0.5 mg/l). Rooted plantlets can be grown in PGR-free liquid MS in test tubes (150×25 mm) containing cheesecloth as the anchor material to achieve faster growth. Regenerated plantlets are transplanted to potting media, acclimatized then grown to maturity in the greenhouse.

Figure 11:
FIG. 11 shows corn plastid transformation. Transformed corn plants grow normally (middle shoot) while untransformed plants die on the lethal medium, confirming lethal selection by the antibiotic, (1000 µg/ml spectinomycin).

FIG. 11 shows corn plastid transformation. Transformed corn plants grow normally (middle shoot) while untransformed plants die on the lethal medium, confirming lethal selection by the antibiotic spectinomycin (1000 µg/ml).

EXAMPLE 4

Rice Chloroplast Transformation. Surface sterilization of rice seeds and preculture. Dehusked seeds from any genotype (indica or japonica types) are surface sterilized first in 70% ethanol for 10 min under continuous shaking then rinsed with ddw about five times. Seeds are then soaked in a 0.2% Benlate (w/v) solution for 20 min, rinsed with sddw five times, then in 50% bleach for 20 min with the sddw rinses repeated. Seeds are pre-cultured in medium RG1 [MS salts, sucrose and DM-vitamins as above, BA (2.0 mg/l) at pH 5.8]. As with corn, liquid RG1 is dispensed to Magenta™ boxes containing cheesecloth prior to autoclaving. Seeds are placed in RG1 (100 seeds of any genotype per box) and pre-cultured overnight (16 h or continuous light; 23 C) prior to bombardment the following day.

Figure 12A:
FIGS. 12A-F shows rice plastid transformation and regeneration.

Bombardment of embryos on intact rice seeds. Pre-cultured seeds are tightly packed vertically, embryo end up (FIG. 12A), in the central 2.5 cm area of a petri dish (25 per dish) containing medium RG1.1 (RG1 plus 8.0 g/l phytagar) and bombarded with DNA-coated microprojectiles.

DNA precipitation. The procedure is as described for corn with the following modifications. Ten µl DNA (1.0 µg/µl) and 20 µl isopropanol (2×vol of DNA), 60 µl 2.5 M $CaCl_2$ and 15 µl 0.1M spermidine are used. Each shot delivers 2.0 µg DNA and 720 µg tungsten.

FIGS. 12A-F shows rice plastid transformation and regeneration scheme. A) Rice seeds, embryo end up, just prior to bombardment; arrows point to embryo margins; B) Multiple shoot induction from one control embryo after seven weeks in culture; C) Selection of plastid transformed rice shoots arising from one initial rice embryo in media containing spectinomycin and streptomycin after eight weeks in selective medium; arrows point to two putative transformants; D) Control rice regenerants; E) Transgenic Priscilla 2.3; F) Transgenic Priscilla 2.4.

Figure 12B:
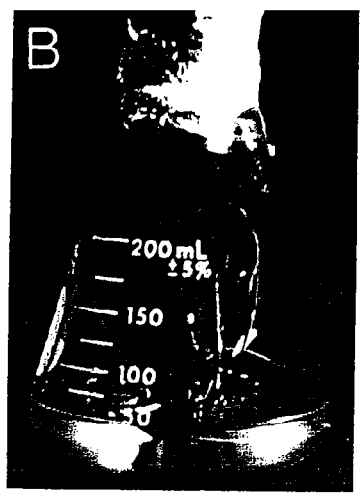
Figure 12C:
Figure 12D:
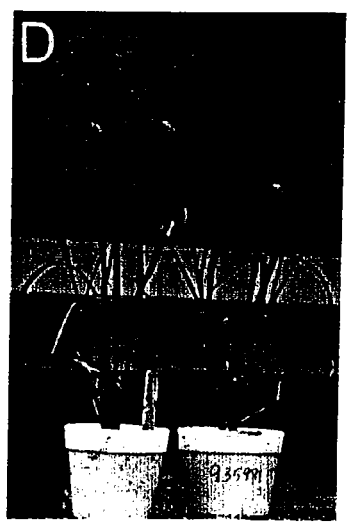
Figure 12E:
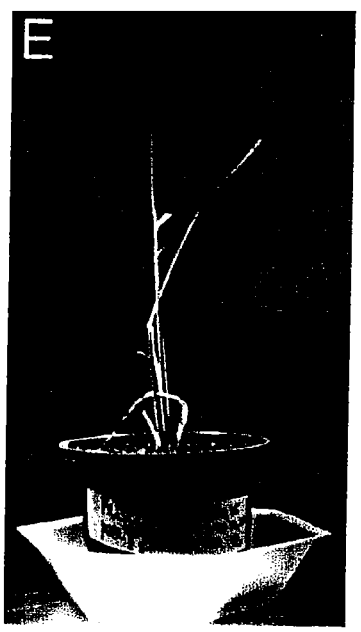
Figure 12F:
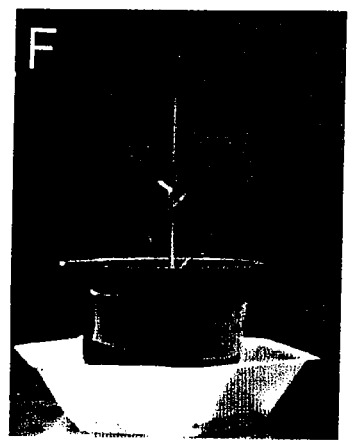

Multiple shoot induction and selection of transplastomics post-bombardment. The rice seeds are separated and spread out on the RG1.1 medium (maintaining the polarity) and placed in the dark for two days post-bombardment. The embryo end of the seed is then cut away (embryo plus small amount of endosperm) from the remainder of endosperm which is discarded. Embryos are placed in 50 ml liquid RG2 medium (in 250 ml flask) for multiple shoot induction (FIG. 12B). RG2 contains MS salts, sucrose and DM-vitamins as above, and BA (6.0 mg/l) at pH 5.8. RG2 used for selection includes spectinomycin (1000 µg/ml) plus streptomycin sulfate (100 µg/ml). The cultures are placed in the growth chamber (16 h photoperiod; 25° C.) and subcultured every two weeks into fresh selection media. Green shoots are selected from the shoot clumps arising from each embryo and placed back in selective media (FIG. 12C). Rooting is achieved in medium RG3 [MS salts, sucrose and DM-vitamins as above, IBA (0.5 mg/l) at pH 5.8] plus antibiotics. (Shoots can be either rooted separately or as multiple shoot clusters). Plantlets are transplanted to potting media, acclimatized then repotted to a clay:sand (1:1) mix and grown to maturity in the greenhouse. (FIGS. 12D,E,F).

Development of plastid transformation and regeneration protocols for corn and rice. As described above unique corn nuclear transformation and regeneration protocols (FIG. 10) were developed (Rudraswamy, 1997) and adapted for plastid transformation. (Previous to this work, nodal section explants had not been used for transformation or regeneration.) Multiple shoots were induced on nodal sections excised from three day-old seedlings of 21 genotypes (none related to A188 or B73) which included hybrid (16 grain, one sweet) and inbred (four) genotypes. After eight weeks in culture, 16-32 shoots (avg. 24) were generated per explant. Shoots were rooted and regenerants did not display aberrant phenotypes in greenhouse analyses (limited study of two plants per genotype). DNA could also be delivered into nodal section explants of all genotypes (FIG. 10C; transient β-glucuronidase expression). For plastid transformation, nodal section explants were bombarded with pSBL-ctV2, then placed on a multiple shoot induction medium containing spectinomycin and streptomycin. Arising shoots could be excised and re-placed on shoot induction medium for subsequent rounds of selection.

As described above unique rice targets dehusked intact mature seeds, embryo end up, not used in previously reported transformation protocols were coupled with a multiple shoot induction protocol (FIG. 12) for mature embryos (excised two days post-bombardment). Multiple shoots were induced on all eight genotypes tested (Litton, Priscilla—two newly released Mississippi cultivars, plus six breeding lines). The noted response should be similar in numerous other cultivars since the initial explant is a mature embryo. Regenerants (non-transformed) are being maintained for collection of F1 seed. After plastid transformation, shoot multiplication occurred in the presence of spectinomycin/streptomycin and, as with corn, shoots could undergo numerous rounds of selection due to shoot proliferation (unknown if axillary or adventitious in origin) from the base of excised shoots. Rooting was also accomplished in selective media.

Figure 13A:
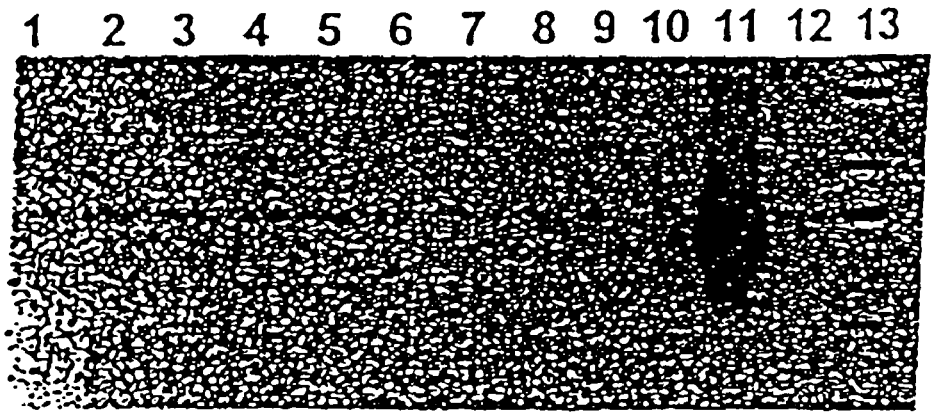
FIGS. 13A and 13B shows PCR analysis of DNA isolated from the leaves of rice transformants.
Figure 13B:
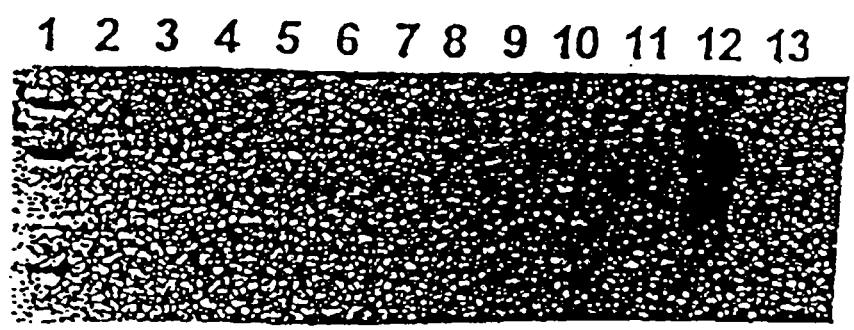

FIGS. 13A-B shows PCR analysis of DNA isolated from first generation leaves of rice transformants. PCR analysis was done with DNA isolated from the first generation leaves. The PCR products were not abundant as observed in tobacco chloroplast transgenic plants (FIGS. 13A, lane 11, 13B, lane 12). This may be because of two reasons. The protocol used to isolate DNA is not suitable for coarse rice leaves or that the primers designed for tobacco do not anneal as well with rice ct DNA. Nevertheless, for preliminary analysis, tobacco primers were used to test integration of the aadA gene into the plant genome from the universal vector. Lack of a product would indicate spontaneous mutants, capable of growing on spectinomycin without the aadA gene (FIG. 13A, lanes 7-10). A PCR product of 1.57 Kb was detected in four lines (FIG. 13A, lanes 2-6) transformed with the universal vector. Under the selection conditions used, four mutants were detected out of ten lines transformed with the universal vector. Primers were also designed to specifically identify integration into the plastid genome. For the universal vector, the primer on the native chloroplast genome landed in the 16s rRNA gene, outside the flanking sequence of the chloroplast vector (1.60 Kb PCR product). The expected products were observed for the transgenic lines obtained using the universal vector (FIG. 13B, lanes 5, 6). Unbombarded plants (controls) did not yield any PCR products, as expected (FIG. 13B, lane 2; FIG. 13A, lane 1). PCR results identified two 'Priscilla' rice plants (2.3 and 2.4) which contain transformed plastids (FIGS. 12 and 13).

EXAMPLE 5

Peanut Chloroplast Transformation

*Arachis hypogaea*

Transgenic peanuts having transformed chloroplast genomes were obtained using the universal vector pSBL-CG-CtV2 (FIG. 7A). Peanut tissue was grown in culture in accordance with the protocol described by Kanyand et al., 1994. Bombardment conditions were the same as for tobacco chloroplast transformation as described above, except that epicotyl sections were used for bombardment while using rupture discs of variable pressure. Peanut chloroplast transformation has never been previously reported.

Figure 14:
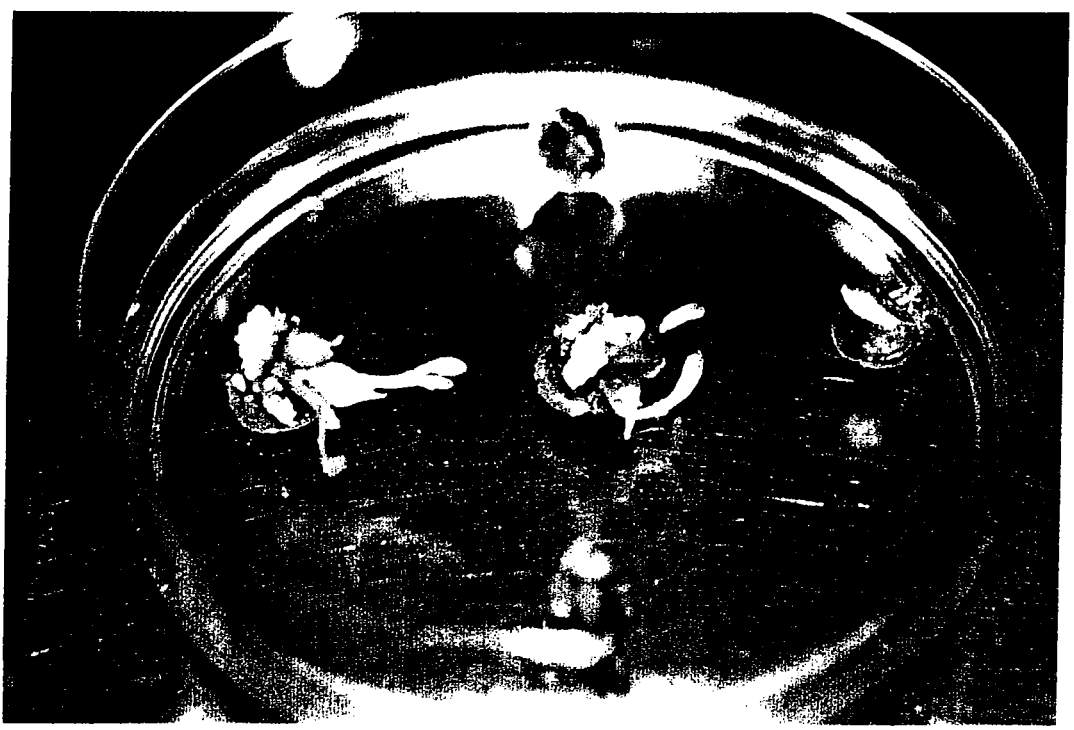
FIG. 14 shows peanut plastid transformation. Transformed peanut plants grow normally (middle and on left side of plate) while untransformed plants die in the lethal medium (500 µg/ml spectinomycin).

FIG. 14 shows peanut plastid transformation. Transformed peanut plants grow normally (middle and on left side of plate) while untransformed plants die in the lethal medium (500 µg/ml).

EXAMPLE 6

Soybean Chloroplast Transformation. Transgenic soybeans having transformed chloroplast genomes were obtained using the universal vector pSBL-CG-CtV2 (FIG. 7A). Bombardment conditions were as for tobacco chloroplast transformation. Soybean chloroplast transformation has never been previously reported.

Figure 15:
FIG. 15 shows soybean plastid transformation. Two transformed plants show shoots, the other plants die on the lethal medium, confirming lethal selection by the antibiotic (500 µg/ml spectinomycin).

FIG. 15 shows soybean plastic transformation. Two transformed plants show shoots, the other plant die on the lethal medium, confirming lethal selection by the antibiotic spectinomycin (500 µg/ml).

EXAMPLE 7

Sweet Potato Chloroplast Transformation. Transgenic sweet potato plants having transformed chloroplast genomes were obtained using the universal vector pSBL-CG-CtV2 (FIG. 7A). Sweet potato tissue were grown in culture in accordance with the protocol described by Zhang et al., 1996. Bombardment conditions were the same as for tobacco chloroplast transformation as described above, except that calli and primary embryos were bombarded and, after bombardment, were transferred to plates containing 100 mg/ml spectinomycin. Sweet potato chloroplast transformation has never been previously reported.

Figure 16:
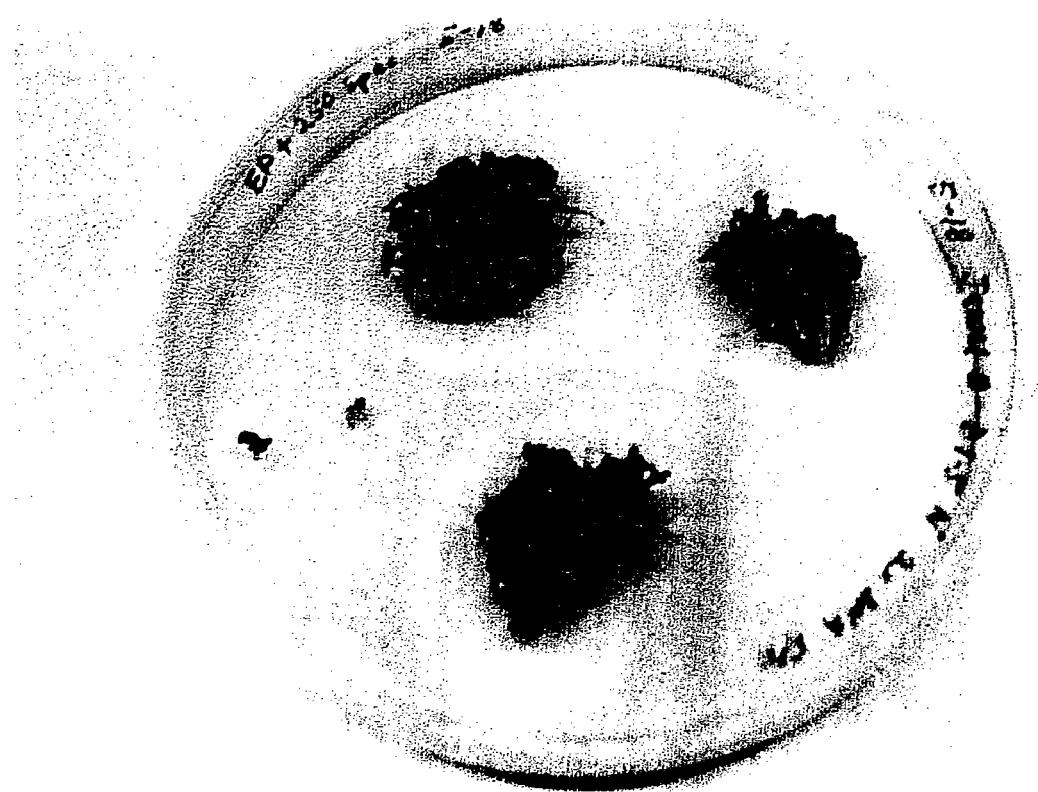
FIG. 16 shows sweet potato embryo transformation on lethal selection medium (500 µg/ml spectinomycin).

FIG. 16 shows sweet potato embryos transformation on the lethal antibiotic spectinomycin selection medium (500 µg/ml). Note bleached calli (right) and green embryos (left).

EXAMPLE 8

Grape Chloroplast Transformation. Transgenic grape plants having transformed chloroplast genomes are obtained using the same universal vector pSBL-CG-CtV2. Grape tissue are grown in culture according to the protocol of Hebert et al., 1993. All chloroplast transformation protocols are as for tobacco, except that cells in the exponential phase of growth, about 4 days after subculturing, were used for bombardment. Grape chloroplast transformation has never been previously reported.

Figure 17:
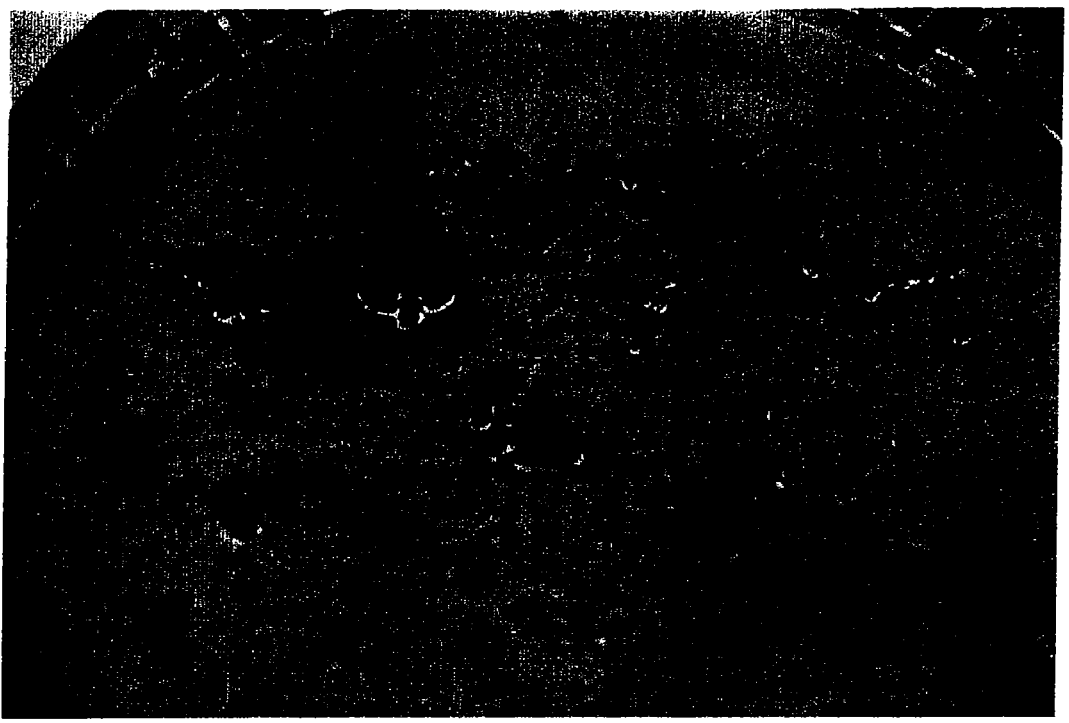
FIG. 17 shows grape cells transformation. The transformed culture cells become green while the untransformed cells die in the lethal selection medium (500 µg/ml spectinomycin).

FIG. 17 shows grape cells transformation. The transformed culture cells become green while the untransformed cells die in the lethal antibiotic spectinomycin selection medium (500 µg/ml).

EXAMPLE 9

Transformation of Other Plants. Transformation of plants by means of microprojectile bombardment is a favored technique to introduce the universal vector carrying the desired nucleotide sequence coding for the molecule of interest into the target plants. Illustrative transgenic plants obtained through microprojectile bombardment are shown in Table II.

TABLE II

Transgenic Plants Recovered
Through Microprojectile Bombardment

| Plant Species | Explant Utilized for Transformation |
|---|---|
| Alfalfa | Cali from petiole, stem sections |
| Arabidopsis | Root sections |
| Barley | Embryogenic callus, immature embryos |
| Banana | Embryogenic suspension cells |
| Bean | Meristems |
| Citrus | Embryogenic cells |
| Cotton | Embryogenic suspensions; meristems |
| Cranberry | Stem sections |
| Cucumber | Cotyledons |
| Dendrobium orchid | Protocorms |
| Eucalyptus | Zygotic embryos |
| Grape | Embryogenic suspension cells |
| Maize | Embryogenic suspensions; immature embryos |
| Oat | Embryogenic |
| Papaya | Zygotic/somatic embryos; hypocotyls |
| Pasture grass | Embryogenic calli |
| Peach | Embryo derived calli |
| Peanut | Meristems |
| Poplar | Embryogenic |
| Rice | Zygotic embryos |

The transformation of plants by the use of the gene gun is described in Daniell, 1997. Each crop that was reported to be nuclear transformable via microprojectile bombardment in that Table can have its chloroplast genome transformed using the universal vector as described herein.

EXAMPLE 10

Expression of Non-Plant Products

The examples that follow, illustrate the expression of biodegradable protein-based biopolymers (PEPs) and analysis of transformants.

Vector pSBL-CG-EG121. The vector pSBL-CG-EG121 (FIG. 3A) contains the gene (GVGVP)$_{121mer}$ (designated EG121) which codes for a biodegradable protein-based biopolymer (PBP) that has many medical and non-medical applications.

Construction of Chloroplast Expression Vectors. Standard protocols for vector construction were as outlined by Sambrook et al., 1989. Chloroplast integration and expression vectors pSBL-CtV2 (FIG. 7A) and pZS197 were digested, respectively, with XbaI (an unique site between the aadA gene and the psbA 3' region) and SpeI (a unique site at 120 bp downstream of the aadA geen in the psbA 3' regulatory region), Klenow filled and dephosphorylated. The polymer gene EG121 along with the Shine-Dalgarno sequence (GAAGGAG) from the pET11d vector was excised as a XbaI-BamHI fragment from the plasmid pET11d-EG121. Sticky ends of the insert fragment were Klenow filled and ligated with vectors pSBL-CtV2 or pZS197 yielding chloroplast expression vectors pSBL-CG-EG121 (FIG. 3A) and pZS-CG-EG121 (FIG. 3B), which integrate the aadA and EG121 genes at the inverted repeat (IR) or into the spacer region between the rbcl and orf 512 genes of the tobacco chloroplast genome. Refer to FIG. 1, for "V" and "TV", integration sites, respectively.

Biopolymer Expression in E. coli and Tobacco. Plasmid vector pSBL-CG-EG121 (FIG. 3A) was transformed into E. coli strain XL-1 Blue and grown in Terrific Broth in the presence of ampicillin (100 μg/ml) at 37° C. for 24 h. SDS-PAGE was carried out according to Laemmli, 1970 using a 12% resolving gel and a 5% stacking gel and run for 5 h at a constant current of 30 mAmps. Crude protein extracts from *E. coli* cells were prepared and electrophoresed as described by Guda et al., 1995. After electrophoresis, polypeptides were visualized by negative staining with $CuCl_2$.

Figure 18:
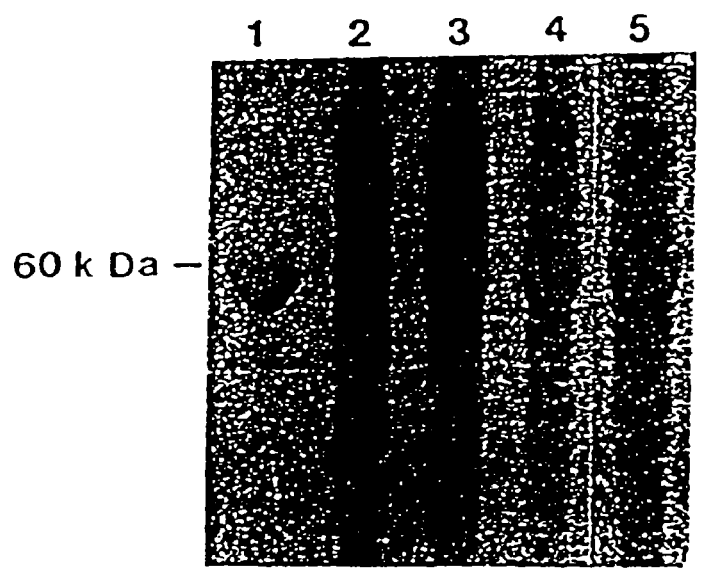
FIG. 18 shows protein-based biopolymer (PBP) expression by chloroplast integration and expression vectors in *E. coli*.

FIG. 18 shows expression of chloroplast integration and expression vectors in *E. coli* strain HMS174 (DE3). Lane 1, shows the purified polymer protein; lane 2, shows the untransformed *E. coli* control; lane 3, shows the *E. coli* strain XL-1 Blue transformed with universal vector PSBL-CG-EG121 (FIG. 3A); lane 4 shows *E. coli* transformed with the tobacco vector and lane 5, shows *E. coli* strain HMS174 (DE3) transformed with pET11d-EG121 vector, in which the T7 promoter transcribes the polymer gene. The level of expression by the Prrn promoter in *E. coli* was almost equivalent to that of the highly efficient T7 promoter driving the polymer gene.

Southern Blot Analysis. Total DNA was extracted from leaves of transformed and wild type plants using the CTAB procedure of Rogers and Bendich, 1988.

Figure 19A:
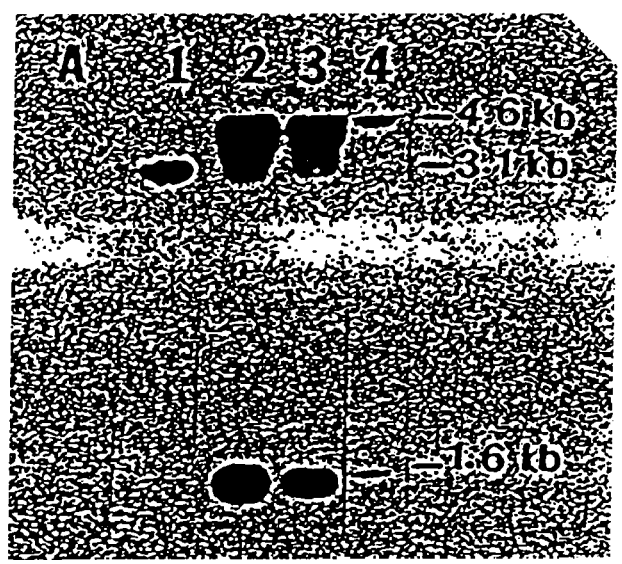
FIGS. 19A-B show Southern blot analysis performed with the transformants from PBP transgenic plants using the tobacco vector (TV). Probes were from chloroplast border sequences (A) or from polymer (EG121) gene sequences (B).
Figure 19B:
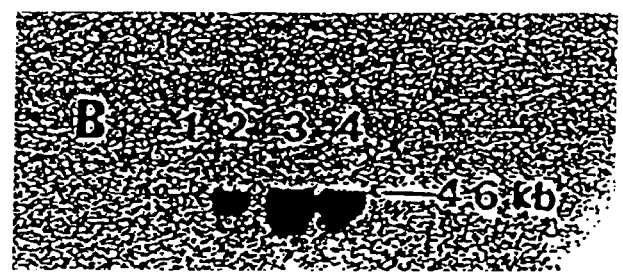
Figure 20A:
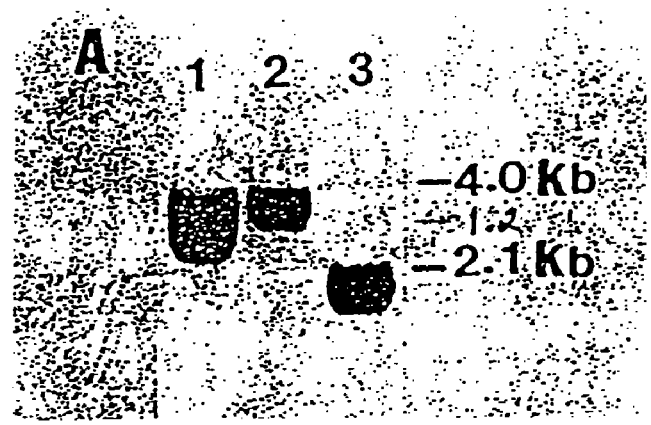
FIGS. 20A-B show Southern blot analysis performed with the transformants from PBP transgenic plants using the universal vector (UV). Probes were from chloroplast border sequences (A) or from the aadA gene (B).
Figure 20B:
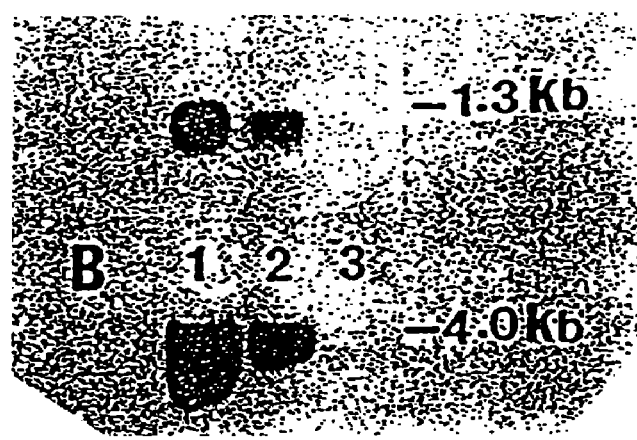

FIGS. 19 and 20 show Southern blot analysis performed independently with the transformants obtained using the tobacco (FIG. 19) and the universal (FIG. 20) vectors. Total DNA was digested with EcoRI and HindIII in case of the universal vector (UV) transformants or EcoRI and EcoRV in case of the tobacco vector (TV) transformants. Presence of an EcoRI site at the 3' end of the polymer gene allowed excision of predicted size fragments in the chloroplast transformants only. To confirm foreign gene integration and homoplasmy, individual blots were probed with corresponding border sequences. In the case of the TV transformants after the second or third round of selection, the border sequence hybridized with 4.6 and 1.6 kbp fragments (FIG. 19A, lanes 2, 3 and 4) and with a 3.1 kbp native fragment in the wild type (FIG. 19A, lane 1). On the other hand, in the case of the UV transformants, after the first round of selection, the border sequence hybridized with 4.0 kbp and 1.2 kbp fragments (FIG. 20A, lanes 1 and 2) while it hybridized with a native 2.1 kbp fragment in the control (FIG. 20A, lane 3). Moreover, TV transformants also showed the native fragment of 3.1 kbp (FIG. 19A, lanes 2 and 3) similar to the wild type plant indicating heteroplasmic condition of the transformed chloroplast genomes, even though they have been under several rounds of selection. However, both UV transformants showed homoplasmic condition, even after the first round of selection (FIG. 20A, lanes 1, 2).

Presence of heteroplasmy even after second selection was reported earlier and it was suggested that selection should be done until attainment of homoplasmy (Svab and Maliga, 1993). This is consistent with the observation that a high degree of heteroplasmy exists after a second selection cycle in the TV transformants (FIG. 19A, lanes 2 and 3). However, no heteroplasmic condition was observed in case of the UV transformants which may be because of the copy correction mechanism between the two IR regions and/or the presence of chloroplast origin of replication (ori) within the border sequence, which should increase the copy number of the introduced plasmid before integration.

DNA gel blots were also probed with either the aadA gene (UV integrated plants) or the EG121 gene (TV integrated plants) to reconfirm integration of foreign genes into the chloroplast genomes. In the TV integrated plants, the polymer gene probe hybridized with a 4.6 kbp fragment, only in the plastid transformant lines (FIG. 19B, lanes 2, 3 and 4). Also, in the UV integrated plants, aadA sequence hybridized with an expected 4.0 kbp fragment (FIG. 20B) which also hybridized with the border sequence in plastid transformant lines (FIG. 20A, lanes 1 and 2).

Analysis of Transcript Levels in Transgenic Tobacco and Northern Blot. Foreign gene transcript levels were analyzed by northern blotting (FIG. 21) using total RNA isolated from the control, chloroplast transformants and a tobacco transgenic plant highly expressing the polymer gene (EG121) via the nuclear genome (Zhang et al., 1996). The polymer gene (EG121) sequence hybridized with a 1.8 kbp fragment in the chloroplast transformants (lanes 1-4, 5-6) and also with larger size fragments in one of the chloroplast transformants (lane 6). In the case of the nuclear transformant, a transcript of about 2.1 kbp was observed (lane 7). This was due to the presence of a poly A tail at the 3' end of the polymer transcript provided by the nos terminator. The larger size fragments observed in lane 6 may be the di-, tri- or polycistronic transcripts which are being processed in chloroplasts. This is a common phenomenon in chloroplast gene expression because many plastid genes are organized into polycistronic transcriptional units that give rise to complex sets of overlapping mRNAs. Quantitation of transcript levels revealed that the chloroplast transformants were producing a 11-fold (lane 5) or more than fifty fold (lane 6) of polymer transcripts over that of a highly expressing nuclear transformant (lane 7, highest expressing plant among thirty five TV nuclear transgenic plants examined). This is directly attributed to the presence of higher gene copy numbers in chloroplasts of transgenic plants. The tobacco vector (TV) integrated plastid transformants showed lower levels of polymer transcript (lanes 1-4) compared to the universal vector integrated transformants (lanes 5, 6) because the polymer gene exists as two copies per transformed plastid genome in universal vector transformants as against a single copy in the TV transformants and the heteroplasmic conditions observed in TV transformants.

Figure 21A:
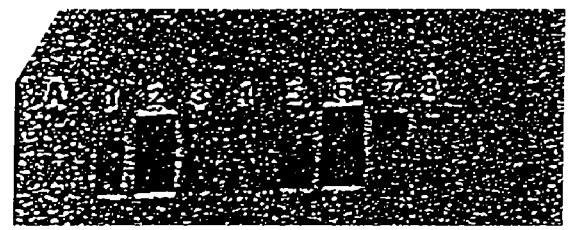
FIG. 21A shows foreign gene transcript levels analyzed by northern blotting using total RNA isolated from the control, chloroplast transformants and a nuclear tobacco transgenic plant highly expressing the synthetic biopolymer gene (EG121).
Figure 21B:
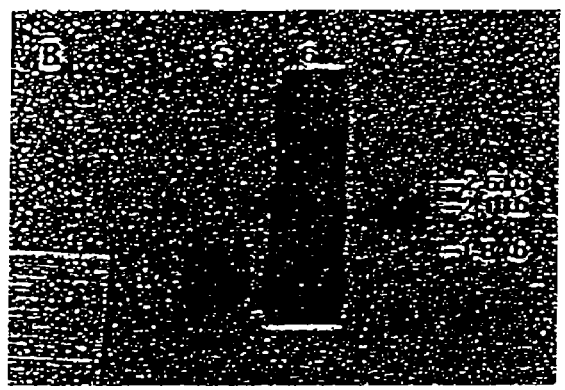
FIG. 21B shows an enlargement of lanes 4-7 of FIG. 21A.
Figure 22:
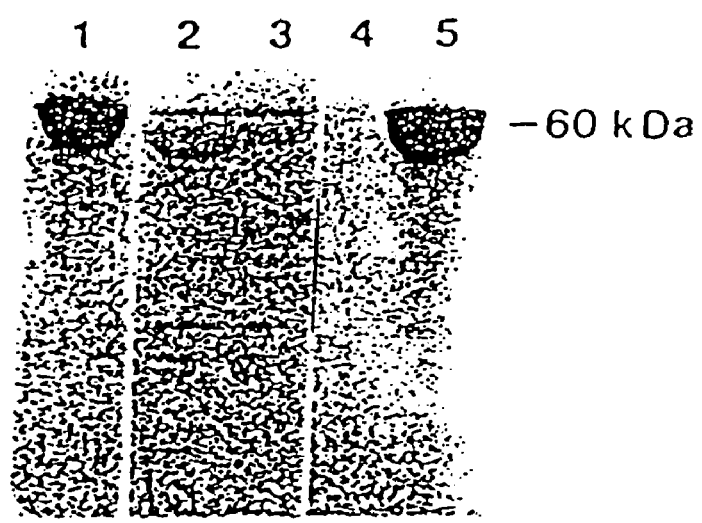
FIG. 22 shows Western blot analysis of purified polymer protein from transgenic plants.

Western Blot Analysis. Polymer protein was purified from leaves from wild type tobacco, chloroplast transformants and nuclear transgenic plants following the method recently described by Zhang et al., 1995. Purified polymer was analyzed by SDS-PAGE according to Laemmli, 1970 using a 120 resolving gel and a 5% stacking gel and run for 5 h at a constant current of 30 mAmps. Polymer polypeptides of about 60 kDa were visualized by negative staining with 0.3 M $CuCl_2$. Gels were destained in 0.25 M sodium EDTA and 0.25 M Tris-Cl, pH 9.0 with three changes of buffer at 10 min intervals. Western immunoblotting and staining (FIG. 22) was carried out as described by Zhang et al., 1996 using a monoclonal antiserum raised against the polymer AVGVP which cross-reacts well with polymer GVGVP and the "Immuno-Blot Assay Kit" (Bio-Rad). The polymer polypeptides running at about 60 kDa are seen in the plastid transformants of IR integrated plants. Polymer expression from a highly expressing F2 generation nuclear transgenic plant (highest expressing plant among 35 transgenic plants examined) is seen in lane 5 (FIG. 22), while no polymer was expressed in the untransformed control as seen in lane 4 (FIG. 22). Eleven to fifty fold higher level of polymer transcripts is shown in the chloroplast transformants (FIG. 21). In the case of chloroplast native occurring proteins like valine and proline whose biosynthetic pathways are compartmentalized in chloroplasts, higher levels of protein can be expected to be produced.

EXAMPLE 11

Genetic Engineering for Glyphosate Tolerance Via the Nuclear and Chloroplast Genomes Chloroplast Integration and Expression Vectors with EPSPS in Tobacco. The EPSPS coding sequence has been recently integrated into the tobacco chloroplast genome (FIG. 1). The chloroplast vector PZS-RD-EPSPS (FIG. 2A) contains the 16S rRNA promoter (Prrn) driving the aadA and EPSPS genes with the psbA 3' region from the tobacco chloroplast genome. This construct integrates the EPSPS and aadA genes into the spacer region between the rbcL and orf512 genes of the tobacco chloroplast genome. FIG. 1, at the "TV" arrow.

Figure 23A:
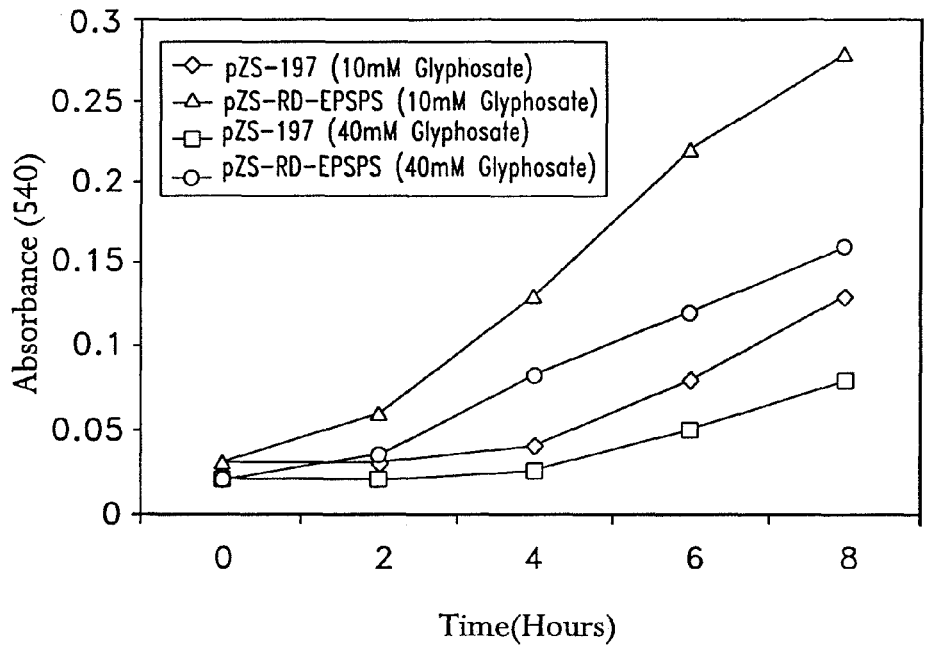
FIG. 23A shows the higher growth rate of *E. coli* containing the tobacco vector with the EPSPS gene.
Figure 23B:
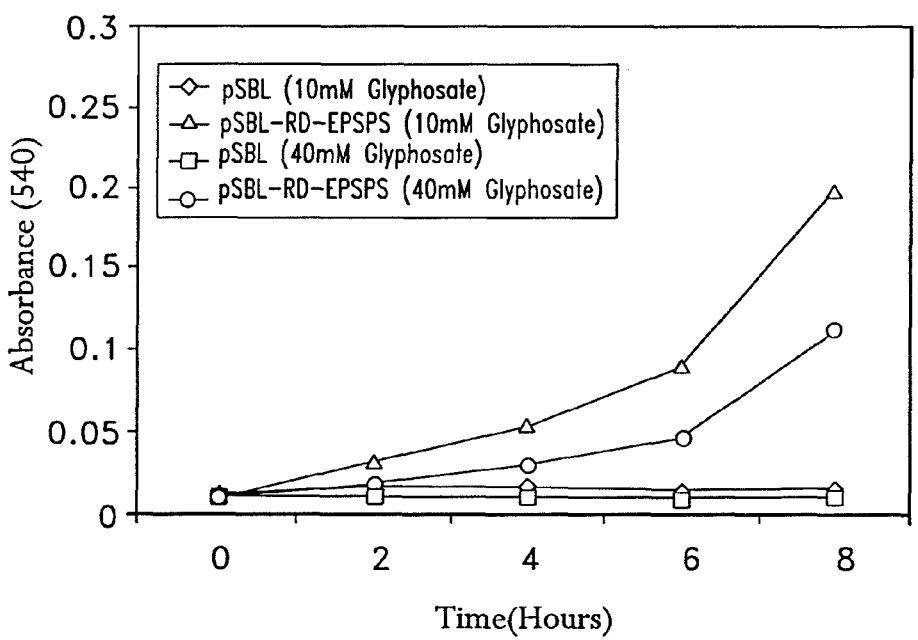
FIG. 23B shows the higher growth rate of *E. coli* containing the universal vector with the EPSPS gene.

Test for Glyphosate Resistance. Gene Expression in *E. coli*. Because of the high similarity in the transcription and translation systems between *E. coli* and chloroplasts (Brixey et al., 1997), chloroplast expression vectors were first tested in *E. coli* for resistance in this case to glyphosate before proceeding with transformation of higher plants. The higher growth rate of *E. coli* containing the tobacco vector compared to the control containing pZS197 (similar to pZS-RD-EPSPS but lacked the EPSPS gene) in the presence of 10 mM and 40 mM glyphosate (FIG. 23A) indicates glyphosate tolerance of *E. coli* expressing the EPSPS gene. Another growth curve (FIG. 23B), confirms the expression of EPSPS via the universal vector in *E. coli*. Thus, glyphosate tolerance of *E. coli* is due to the expression of the EPSPS gene, present in both the tobacco and universal vectors.

Characterization of Tobacco Transgenic Plants

Integration of the Gene. Fully expanded green leaves of *Nicotiana tabaccum* var. *Petit Havana* were bombarded with the tobacco and the universal chloroplast vectors. Two days after bombardment, leaf explants were transferred to selection lethal medium containing spectinomycin (500 μg/ml). Transgenic plants were obtained within 3-5 months after bombardment. Typically, out of 16 bombarded leaves, 10 independently transformed shoots were identified.

PCR analysis was performed with DNA isolated from the first or second generation shoots and also from the mature transgenic plants. Primers were used to confirm integration of the aadA gene into the plant genome from the tobacco as well as universal vectors. Lack of a product would indicate spontaneous mutants, capable of growing on spectinomycin without the aadA gene. The expected PCR product (887 bp) was obtained from six lines (FIGS. 24A-B, lanes 1-6) transformed with the tobacco vector. A PCR product of 1.57 Kb was detected in four lines (FIGS. 24A-B, lanes 1-4) transformed with the universal vector. Under the selection conditions used, four mutants were detected out of ten lines transformed with the tobacco vector. On the other hand, all the transgenic lines transformed with the universal vector showed integration of the aadA gene.

Figure 24A:
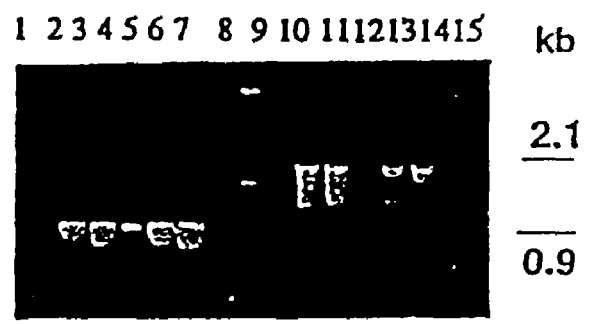
FIGS. 24A-B show the integration of foreign genes into the plastid genome by PCR using rbcl and aadA primers (A), or 16SRNA and aadA primers (B).
Figure 24B:
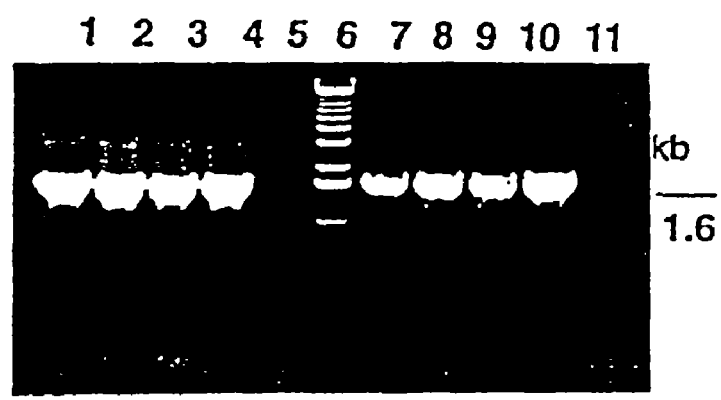

PCR Chloroplast Integration. Primers were also designed to specifically identify integration into the plastid genome. The strategy here was to land one primer on the native chloroplast genome, adjacent to the point of integration of the vector, while landing the other on the aadA gene. A primer was designed to land immediately outside the rbcL gene in the tobacco vector (2.08 Kb PCR product). For the universal vector, the primer on the native chloroplast genome landed in the 16s rRNA gene (1.60 Kb PCR product). The expected products were observed for the transgenic lines obtained using the tobacco vector (FIGS. 24A-B, lanes 2-7) as well as the universal vector (FIGS. 24A-B, lanes 1-4). Unbombarded plants (controls) did not yield any PCR products, as expected (FIGS. 24A, lanes 1 and 9; 24B, lanes 5 and 11). Thus, all transgenic plants examined turned out to be chloroplast and not nuclear transformants perhaps due to the requirement of higher levels of aminoglycoside adenyl transferase (AADA) in transgenic plants under stringent selection conditions. Low levels of AADA present in the codicil of nuclear transgenic plants, should have eliminated nuclear transformants. The results of PCR analysis are conclusive and provide definitive evidence for chloroplast integration of foreign genes using both the tobacco and universal vectors.

Figure 25A:
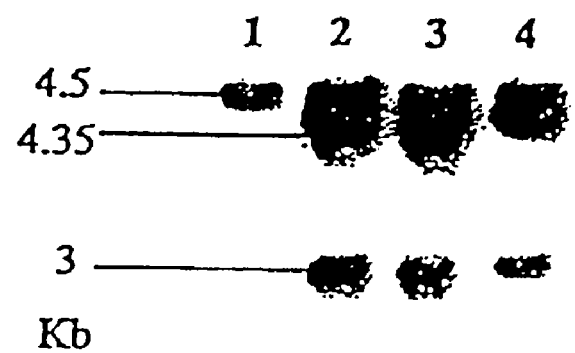
FIGS. 25A-C show the integration of the aroA gene into the chloroplast by Southern analysis and the high generation of homoplasmy using EPSPS probe (A) or rcbL-orf512 probe. The site of integration is shown in (C).

Southern Analysis. The integration of the aroA gene into the chloroplast was also confirmed by Southern analysis. In addition, the high level of resistance to glyphosate observed (FIG. 20A) was confirmed by determination of the copy number of the foreign gene in the transgenic plants. The probe, to determine integration of the foreign gene into the chloroplast genome, comprised 654 bp fragment of the EPSPS gene, random primer labeled with $P^{32}$. The total DNA comprising both organellar and genomic was digested with EcoRI. The presence of an EcoRI site 200 bp upstream from the integration site, in the chloroplast genome, was used to confirm integration of the EPSPS gene into the chloroplast genome in transgenic plants. The probe hybridized to the native EPSPS gene, present in the nuclear genome, is seen as 4.5 Kb fragment. In addition, the probe hybridized to the digested chloroplast genomes of the transgenic tobacco plants, generating the 3.5 kb and 4.35 Kb fragments in FIG. 25A, lanes 2, 3 and 4. The probe did not hybridize to the digested chloroplast genome of the untransformed control plant (FIG. 25A, lane 1) since the foreign gene is not present in the chloroplast genome of tobacco. This clearly establishes the integration, of the EPSPS gene, into the chloroplast genome.

Figure 25B:
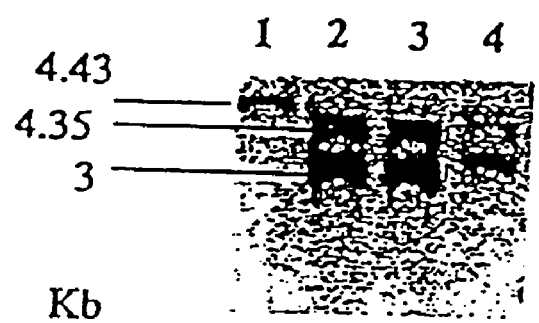
Figure 25C:
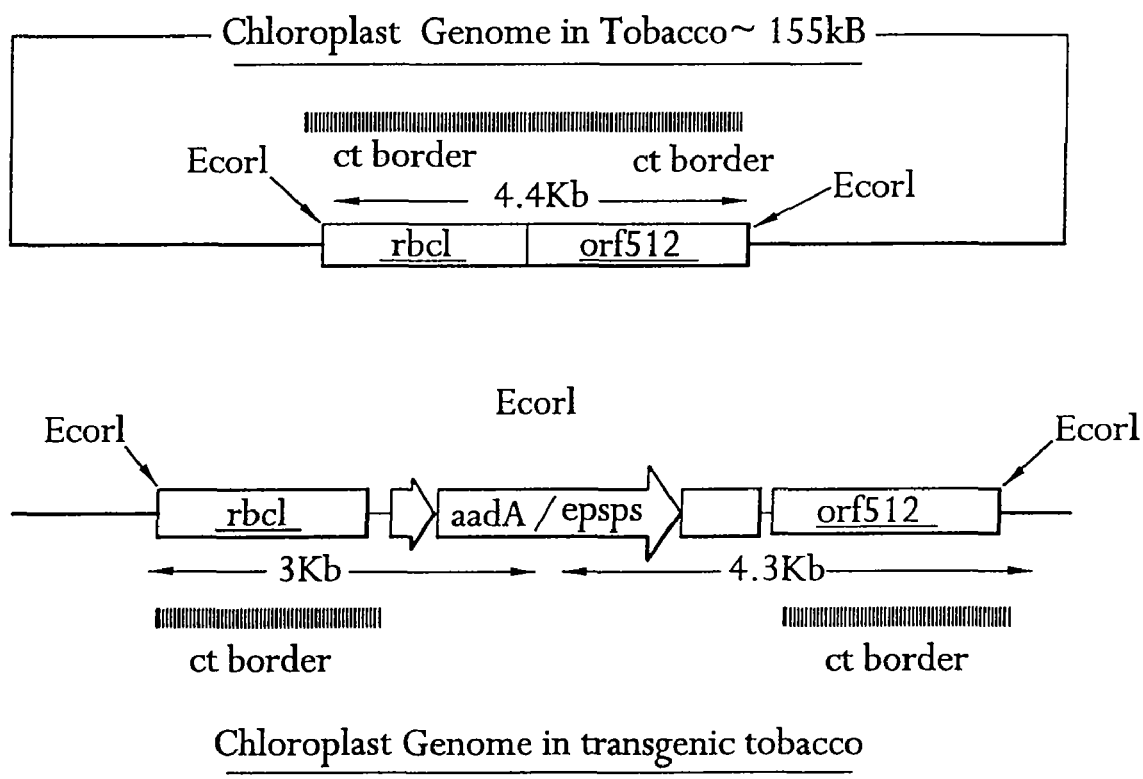

Gene Copy Numbers. The copy number of the integrated gene was determined by establishing homoplasmy for the transgenic chloroplast genome. Tobacco chloroplasts contain 5000-10,000 copies of their genome per cell. (McBride et al, 1995) If only a fraction of the genomes are actually transformed, the copy number, by default, must be less than 10,000. By establishing that in the transgenics the EPSPS transformed genome is the only one present, one could establish that the copy number is 5000-10,000 per cell. This was shown by digesting the total DNA with EcoRI and probing, with the flanking sequences that enable homologous recombination into the chloroplast genome. The probe comprised a 2.9 Kb fragment of the rbcL-orf512 sequences. A chloroplast genome transformed with the EPSPS gene, incorporates an EcoRI site between the rbcL-orf512 region of the chloroplast genome, thereby generating an extra fragment when digested with this enzyme (FIG. 25C). Southern hybridization analysis revealed a 4.43 Kb fragment in FIG. 25B, lane 1 for the untransformed control. In lanes 2, 3 and 4, two fragments (4.35 Kb and 3 Kb) were generated due to the incorporation of the EPSPS gene cassette between the rbcL and orf512 regions (FIG. 25C provides a schematic diagram with the dotted lines in gray signifying the point of integration of the foreign DNA). The 4.43 Kb fragment present in the control is absent in the transgenics. This proves that only the transgenic chloroplast genome is present in the cell and there is no native, untransformed, chloroplast genome, without the EPSPS gene present. This establishes the homoplasmic nature of the transformants, simultaneously providing an estimate of 5000-10,000 copies of the foreign EPSPS gene per cell. This would then explain the high levels of tolerance of glyphosate that was observed in the transgenic tobacco plants (FIG. 20A).

Figures 26A, 26B:
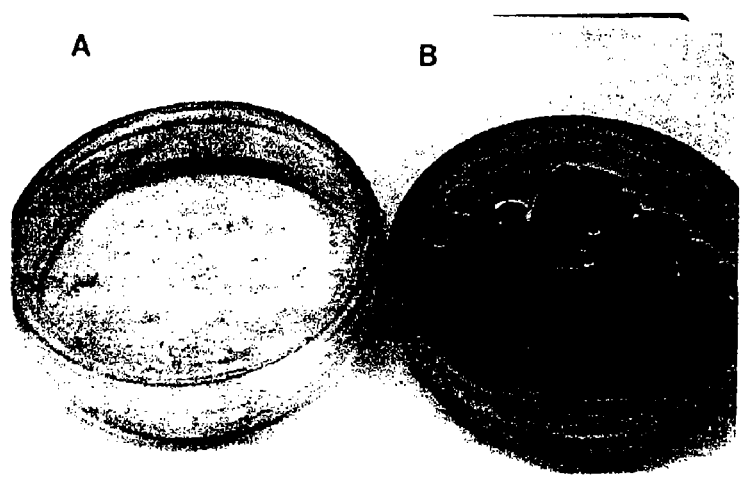
FIGS. 26A and 26B show generation of seeds collected from control and transformed tobacco plants, respectively, in the presence of the selectable markers.

Progeny. Seeds collected from self-pollinated transgenic plants were germinated in the presence of spectinomycin (500 μg/ml). All seeds germinated, remained green and grew normally (FIG. 26B). Uniform spectinomycin resistance indicated that the aadA gene was transmitted to all progeny. Lack of variegation suggested homoplasmy because a heteroplasmic condition would have given rise to variegated progeny on spectinomycin (Svab et al., 1990; Svab and Maliga, 1993). The lack of variation in chlorophyll pigmentation among the progeny also underscores the absence of position effect, an artifact of nuclear transformation. All control seedlings are bleached, and did not grow in the presence of spectinomycin (FIG. 26A).

Figures 27A, 27B:
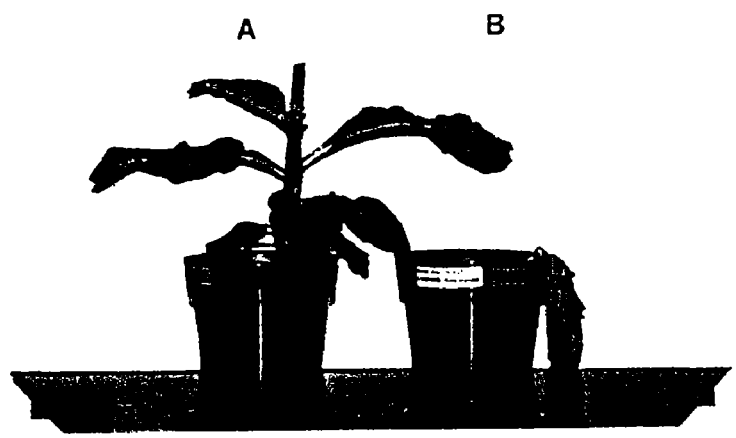
FIGS. 27A and 27B show transgenic and control tobacco plants sprayed with glyphosate.

Tolerance of Glyphosate. Eighteen week old control and transgenic plants were sprayed with equal volumes of glyphosate at different concentrations (0.5 to 5 mM). Control tobacco plants were extremely sensitive to glyphosate; they died within seven days even at 0.5 mM glyphosate (FIG. 27B). On the other hand, the chloroplast transgenic plants survived concentrations as high as 5 mM glyphosate (FIG. 27A). These results are intriguing, considering the fact that the EPSPS gene from petunia used in these chloroplast vectors has a low level of tolerance to glyphosate and also contains the transit peptide for targeting into chloroplasts.

This is the first report of a eukaryotic nuclear gene expression within the prokaryotic chloroplast compartment. It is well known that the codon preference is significantly different between the prokaryotic chloroplast compartment and the eukaryotic nuclear compartment. Ideally, a mutant aroA gene (which does not bind glyphosate) from a prokaryotic system should be expressed in the chloroplast compartment. Such genes are now available and exhibit a thousand fold higher level of resistance to glyphosate than the petunia gene used in this work. In light of these observations, it is possible that integration of prokaryotic herbicide resistance genes into the chloroplast genome as performed herein can result in incredibly high levels of resistance to herbicides while still maintaining the efficacy of biological containment, i.e., avoid dissemination by pollen.

EXAMPLE 12

Tolerance of Corn to Glyphosate. A universal chloroplast vector using corn chloroplast DNA is constructed as follows. First, vector pSBL-Ct-bor (FIG. 5C) is constructed as follows: Corn chloroplast DNA subclone containing one of the inverted repeat regions is constructed with bacterial plasmid pUC19. Second, a smaller subclone containing only the rRNA operon is constructed from the first subclone and the fragment present in the second subclone containing the trnA and trnI genes and spacer regions representing the universal border are subcloned into a pUC19 plasmid at the PvuII site. The resultant plasmid is designated pSBL-Ct-bor. Within plasmid pSBL-Ct-bor, a selectable maker gene cassette containing a chloroplast 16S rRNA promoter, the aadA gene (encoding aminoglycoside 3'adenyl transferase conferring resistance for streptomycin/spectinomycin) and a 3' untranslated region of the chloroplast psbA gene is inserted to construct vector pSBL-CORN. The selectable maker gene cassette is inserted between the trnI and trnA genes in the spacer region, in the direction of the 16S rDNA transcription.

The vector pSBL-CORN-aroA, which contains a mutant aroA gene from *Salmonella typhimurium* (Stalker et al. 1985; Comai et al. 1983) that encodes the enzyme EPSPS synthase, is constructed by inserting the mutant aroA gene into the pSBL-CORN vector. Transgenic corn plants expressing the mutant aroA gene are resistant to glyphosate treatment like "Roundup™" whereas the untransformed control plants are not.

EXAMPLE 13

Chloroplast Transformation for Tolerance to Imidizolinones or Sulfonylureas. Plasmid pSBL-CORN is modified by insertion of a DNA fragment containing a mutated form of the acetolactate synthase gene of *Saccharomyces cerevisiae* (Falco and Dumas. 1985; Yadav et al. 1986) to generate plasmid pSBL-CORN-ASL1. This gene encodes an acetolactate synthase that is not inhibited by imidizolinones or sulfonylureas and confers tolerance to herbicides containing sulfometuron methyl and herbicides containing Imazapyr. Transformed tobacco plants expressing the mutant acetolactate synthase gene are resistant to imidizolinone and sulfonylurea herbicide sprays.

The vector pSBL-CORN-ALS2 is a derivative of pSBL-CORN that contains mutated copies of the tobacco suRA and suRB genes (Chaleff and Ray. 1984). These genes encode the tobacco acetolactate synthase polypeptide. The plasmid pSBL-CORN-ALS2 is constructed by ligating the suRA and suRB genes, isolated from tobacco genomic DNA into the PSBL-CORN vector. The resulting vector confers resistance to imidazolinone and sulfonylurea herbicides.

EXAMPLE 14

Chloroplast Transformation for Tolerance to Photosystem II Inhibitors. Photosystem (PS) II herbicide resistance occurs from mutations within the psbA gene, which enclosed the $Q_B$ protein and is highly conserved among many plants. Resistant plants possess mutations that alter amino acids at specific positions within the $Q_B$ proteins, e.g., residues 219, 251, 255, 264, and 275 (Hirschberg and McIntosh. 1993; Galloway and Mets. 1984; Gloden and Haselkorn. 1985; Erickson et al. 1984; Johanningmeier et al. 1987). Genes possessing these mutations can thus be utilized to confer resistance to herbicides that function by inhibiting electron transport carried out by the PS II system.

Examples of these herbicides include dichlorophenyldimethylurea (DCMU), atrazine, metribuzine, lenacil, phenmedipham, loxynil and dinoseb.

The mutant psbA gene containing a serine to glycine mutation at residue 264 is isolated from genomic DNA of *Chlamydomonas* using the appropriate restriction endonucleases. The resulting fragment can be ligated into the universal chloroplast expression vector pSBL-ctV2 and introduced into *E. coli* XL1Blue. Purified plasmid from this *E. coli* strain is utilized to transform plants. Daniell (1997). Incorporation of the mutant psbA genes into the chloroplast genome and selection of the appropriate transformants are carried out as previously described. Transformed plants producing the mutated psbA protein containing the serine to glycine substitution are resistant to Atrazine™ whereas control plants are not.

The mutant psbA gene containing a valine to isoleucine mutation at residue 219 is isolated from genomic DNA of *Chlamydomonas* using the appropriate restriction endonucleases. A universal vector is constructed as described above. Transgenic plants like corn expressing psbA containing the valine to isoleucine mutation at residue 219 are expected to be resistant to DCMU sprays.

EXAMPLE 15

Tolerance to Auxin Analogs. 2,4-D. The universal chloroplast expression vector psbL-ctV2 can be cleaved with XbaI and ligated with a DNA fragment containing a gene encoding monooxygenase. The resulting construct can be transformed into chloroplasts to generate transgenic plants that contain multiple copies of the monooxygenase gene. The resulting plants expressing high levels of monooxygenase and are expected to be tolerant to 2,4-D.

EXAMPLE 16

Chloroplast Transformation for Insect Resistance. Tobacco plants can be transformed with universal vector pSBL-CtVHBt (FIG. 8A) which contain the cryIIA gene and expresses the CryIIA protoxin, thereby conferring resistance to insects pests like of the family Pyralidoe, such as the tobacco hornworm. Even insects which have developed a resistance or are less susceptible to Bt toxin are killed by the Bt toxin expressed by the gene in the chloroplast vector described herein.

Figures 8A, 8B:
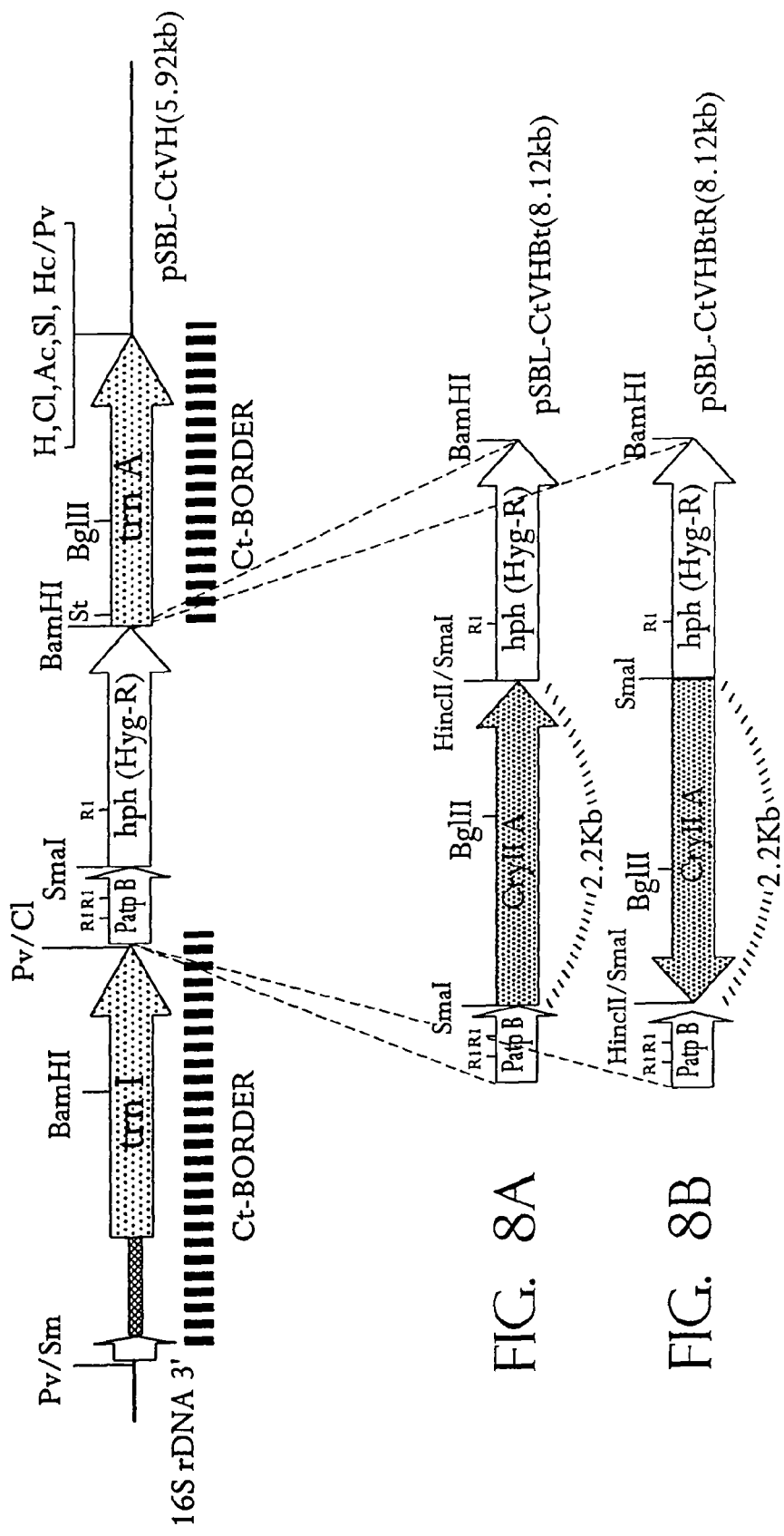
FIGS. 8A and 8B show vectors pSBL-CtVHBt and pSBL-CtVHBtR, respectively.

Vector pSBL-CtVHBt is constructed by cleaving pSBL-CtVH with SmaI and ligating the product with the cryIIA gene encoding the CryIIA protein. The product contained the cryIIA gene in the correct transcriptional orientation (FIG. 8A)

Integration of the cryIIA gene into the tobacco chloroplast genome has been confirmed by PCR analysis. Copy number of cryIIA per cell was estimated to be 10,000 by performing Southern blots. The CryIIA protein was estimated to be between 5 and 10% of total cellular protein by performing Western blots. This is the highest level of CryIIA protein ever reported in Bt transgenic plants. Excised leaf bioassays were performed using non-transformed "Petit Havana" and cryIIA-transformed tobacco. Five to ten larvae were placed on each leaf and evaluated for mortality and leaf damage after 3-5 days. Using susceptible *H. virescens* (YDK), all larvae died within 3 days on cryII-A-transformed tobacco whereas there was no mortality and essentially 100% defoliation on the non-transformed "Petit Havana". Similar results were obtained using CryIAc-resistant (YHD2, 40-50,000 fold resistant) and CryII-A-resistant (CXC, 2000 fold resistant) *H. virescens*. In addition 100% mortality was observed against *Helicoverpa zea* (cotton bollworm), and *Spodoptera exigua* (beet armyworm), neither of which has been previously shown to be killed by any Cry protein.

Figure 28A:
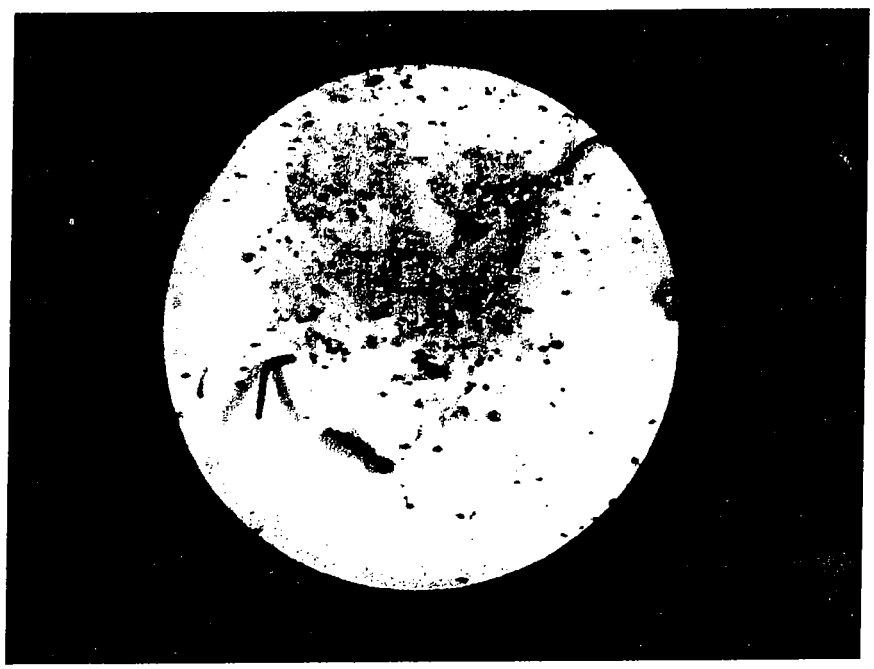
FIGS. 28A and 28B show tobacco susceptibility (control) and resistance (transformed) to insects.
Figure 28B:
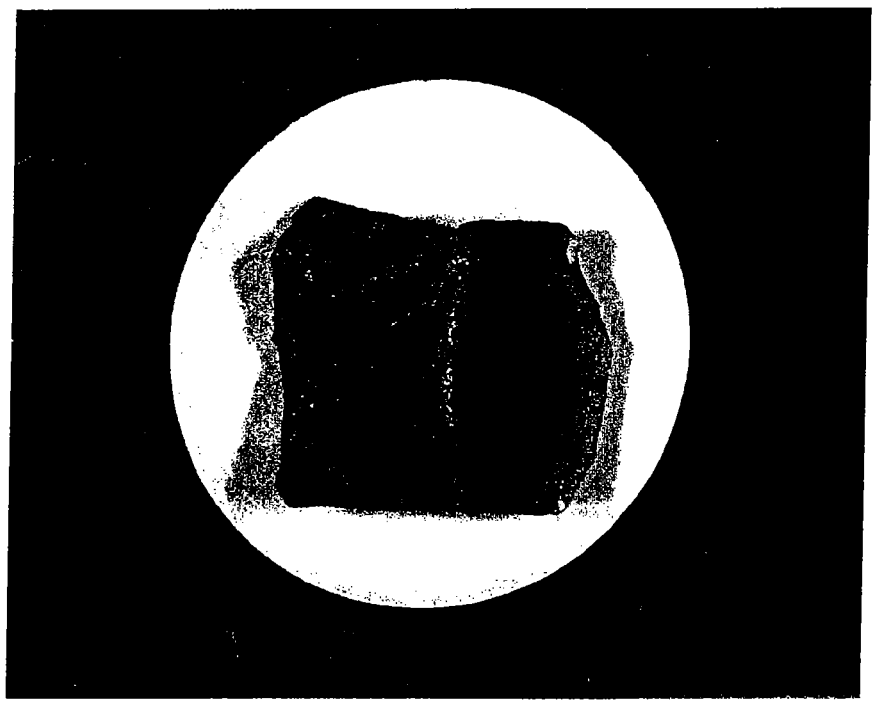

FIGS. 28A and 28B show a bioassay of (A) Control untransformed plant and (B) transgenic plant. Insects tested, demonstrated 100% mortality: Tobacco budworm susceptible to CryI, cotton bollworm and beet armyworm resistant to CryI and CryII.

Figure 29:
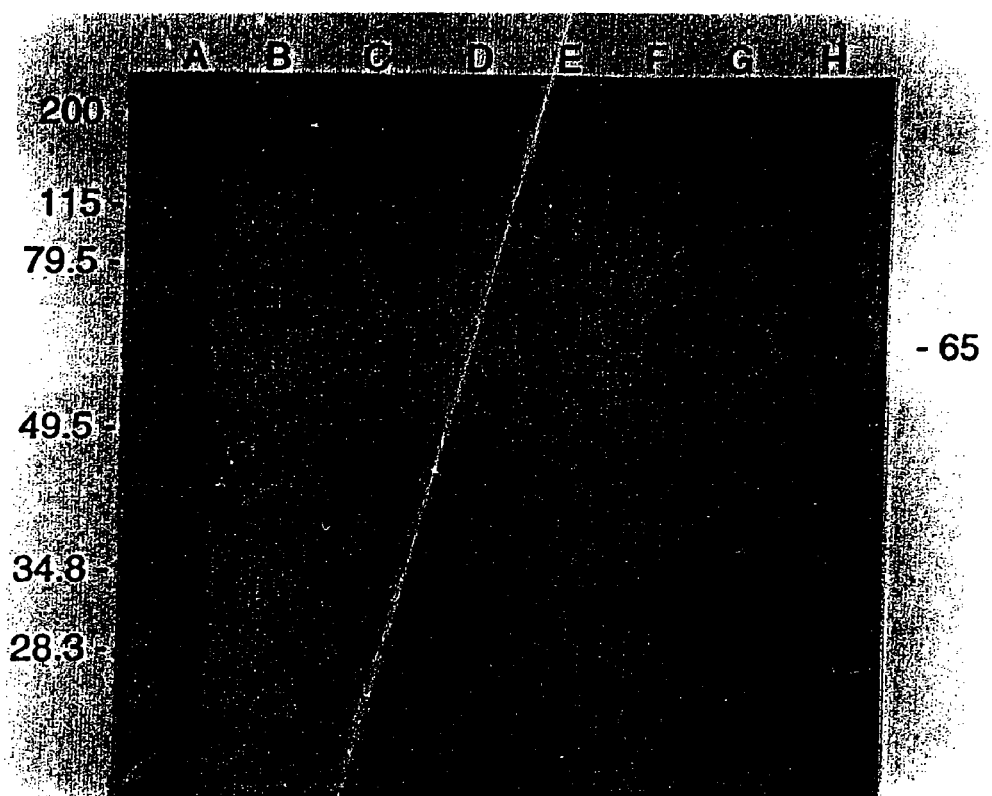
FIG. 29 shows (Western blot analysis) total protein isolated from control and transgenic tobacco plants.

FIG. 29 shows total protein isolated by Western blot analysis from Control (lane C) and transgenic plants (lane B). Lanes D-H represent different concentrations of purified CryIIA protein (1-20%). Lane A shows protein standards.

Other controllable insects are described earlier in the description of the invention.

As will be apparent to those skilled in the art, in light of the foregoing description, many modifications, alterations, and substitutions are possible in the practice of the invention without departing from the spirit or scope thereof. It is intended that such modifications, alterations, and substitutions be included in the scope of the claims.

All references cited in this text are expressly incorporated herein by reference.

REFERENCES

Arntzen Ph.D., Charles J. (1997) *Public Health Reports* 112: 190-197.
Brixey, P. J., Guda, H. and Daniell, H. (1997) *Biotechnol. Lett.* 19, 395-399.
Carlson, P. S. (1973) *Proc. Natl. Acad. Sci. USA* 70:598-602.
Chaleff and Ray. (1984) *Science* 223:1148.
Comai, L., Faciotti, D., Hiatt, W., Thomson, G., Rose, R., and Stalker, D. (1983) *Science* 221:370.
Daniell, H., Guda, C., McPherson, D. T., Xu, J., Zhang, X. and Urry, D. W. (1997) *Meth. Mol. Biol.*, 63:359-371.
Daniell, H., and Guda, C. (1997) *Chemistry and Industry*, pages 555-558.
Daniell, H., Krishnan, M. and McFadden, B. A. (1991) *Plant Cell Rep.* 9: 615-619.
Daniell, H., and McFadden. (1987) *Proc. Nat. Acad. Sci. (USA)* 84: 6349-6353.
Daniell, H., Vivekananda, J., Neilson, B., Ye, G. N., Tewari, K. K., and Sanford, J. C. (1990) *Proc. Nat. Acad. Sci. (USA)* 87: 88-92.
Daniell, H. Porobo Dessai, A., Prakash, C. S. and Moar, W. J. (1994) *NATO Asi Series*. Ed., J. H. Cherry. H86: 598-604.
Darkocsik, C., Donovan, W. P. and Jany, C. S. (1990) *Mol. Microbiol.* 4: 2087-2094.
Daniell, H., (1995) *Inform.* 6: 1365-1370.
Daniell, H., Ramanujan, P., Krishnan, M., Gnanam, A. and Rebeiz, C. A. (1983) *Biochem. Biophys. Res. Comun* 111: 740-749.
Daniell, H. and Rebeiz, C. A. (1982) *Biochem. Biophys. Res. Comun.* 106:466-471.
Daniell, H. (1993) *Methods in Enzymology.* 217:536-556.
Daniell, H. (1997a) *Meth. Mol. Biol.* 62: 453-488.
DeBlock, M., Botterman, J., Vandewiele, M., Docky, J., Thuen, C., Gossele, V., Movva, N. R., Thomson, C., Van Montagu, M., and Leemans, J. (1987) *EMBO J.* 6: 2513-2518.
Erickson et al. (1984) *Proc. Nat. Acad. Sci.* (USA) 81:3617.
Falco and Dumas. (1985) *Genetics* 109: 21.
Gabard, J. M., Charest, P. J., Iyer, V. N. and Miki, B. L. (1989) *Plant Phys.* 91:574-580.
Galloway and Mets. (1984) *Plant Physiol.* 74: 469.
Gloden and Haselkorn. (1985) *Science* 229: 1104.
Guda, C., Zhang, X., McPherson, D. T., Xu, J., Cherry, J., Urry, D. W. and Daniell, H. (1995) *Biotechnol. Lett.* 17: 745-750.
Hirschberg and McIntosh. (1993) *Science* 222: 1346.
Johanningmeier et al. (1987) *FEBS Lett* 211: 221.
Kanyand et al. (1994) *Plant Cell Reports* 14: 1-5.
Kin Ying et al. (1996) *The Plant Journal* 10: 737-743.
King, J. (1996) *Science* 274: 180-181.
Laemmli, U. K. (1970) *Nature* 227: 680-685.
Langevin, S. A., Clay, K. and Grace, J. B. (1990) *Evolution* 44: 1000-1008.
Lewellyn and Fitt (1996) *Molecular Breeding* 2: 157-166.
Lu, Z., Kunnimalaiyaan, M. and Nielsen, B. L. (1996) *Plant Mol. Biol.* 32: 693-706.
Lyons, P. C., May, G. D., Mason, H. S., and Arntzen, C. J., (1996) *Pharmaceutical News* 3: 7-12.
Maier, R. M., Neckerman, K., Igloi, G. L. and Kössel, H. (1995) *J. Mol. Biol.* 251: 614-628.
May, G. D., Mason, H. S., Lyons, P. C. (1996) *American Chemical Society*, pp. 194-204.
Miele, L. (1997) *Elsevier Trends Journals*, Vol. 15.
Mikkelson, T. R., Anderson, B. and Jörgenson, R. B. (1996) *Nature* 380: 31.

Miki, B. I., Labbe, H., Hatori, J., Ouellet, T., gabard, J., Sunohara, G., Charest, P. J. and Iyer, V. N. (1990) *Theoretical Applied Genetics* 80: 449-458.

McBride, K. E., Svab, Z., Schaaf, D. J., Hogan, P. S., Stalker, D. M. and Maliga, P. (1995) *Bio/Technology* 13: 362-365.

Nielsen, B. L., Lu, Z. and Tewari, K. K. (1993) *Plasmid* 30: 197-211.

Oard, J. H., Linscombe, S. D., Braveramn, M. P., Jodari, F., Blouin, D. C., Leech, M., Kohli, A., Vain, P. Cooley, J. C. and Christou, P. (1996) *Mol. Breed.* 2: 359-368.

Penazloza, V., et al. (1995) *Plant Cell Reports* 14:482-487.

Rudraswamy, V., and Reichert, N. A. (1997) M. S. Thesis. Mississippi State Univ.

Rogers, S. O., and Bendich, A. J. (1988) in *Plant Molecular Biology Manual*, ed. Gelvin, S. B. and Schilperoot, R. A. (Kulwer Academic Publishers, Dordrecht, Netherlands) pp. A6:1-10.

Sambrook, J., Fritch, E. F. and Maniatis, T. (1989) in *Molecular cloning*. Cold Spring Harbor Press, Cold Spring Harbor, N.Y.

Sanford, J. C. (1988) *Trends In Biotech.* 6: 299-302.

Sankula, S., Braverman, M. P., Jordari, F., Linscombe, S. D. and Oard, J. A. (1996) *Weed Technol.* 11: 70-75.

Schultz, A., Wengenmayer, F. and Goodman, H. (1990) *Critical Review in Plant Sciences* 9: 1-15.

Shaner and Anderson, P. C., (1985), *Biotechnology in Plant Science*, 287.

Sijmons, P. C., Cekker, B. M. M., Schrammeijer, B., Verwoerd, T. C., van den Elzen, P. J. M., Hoekema, A. (1990) *Biotechnology* 8: 217-221.

Stalker, et al. (1985) *J. Biol. Chem.* 260: 4724.

Stummann et al. (1988) *Physiologia Plantarum* 72:139-146.

Svab, Z. and Maliga, P. (1993) *Proc. Natl. Acad. Sci.* (USA) 90: 913-917.

Svab, Z., Hajdukiewicz, P. and Maglia, P. (1990) *Proc. Nat. Acad. Sci.* (USA) 87: 8526-8530.

Umbeck, P. F., et al. (1991) *Econ. Entomology* 84: 1943-1950.

Urry, D. W., Nicol, A., Gowda, D. C., Hoban, L. D., McKee, A., Williams, T., Olsen, D. B. and Cox, B. A. (1993) in *Biotechnological Polymers Medical. Pharmaceutical and Industrial Applications*, ed. Gebelein, C. G. (Technomic Publishing Co., Inc., Atlanta, Ga.), pp. 82-103.

Widner, W. R. and Whiteley, H. R. (1989) *J. Bacteriol.* 171: 961-974.

Yadav, et al. (1986) *Proc. Natl. Acad.* (USA) 83: 4418-4422.

Ye, G. N., Daniell, H. and Sanford, J. C. (1990) *Plant Mol. Biol.* 15: 809-819.

Yeh, H., Ornstein-Goldstein, N., Indik, Z., Sheppard, P., Anderson, N., Rosenbloom, J., Cicilia, G., Yoon, K. and Rosenbloom, J. (1987) *Collagen Related Res.* 7: 235-247.

Zhang, X., Guda, C., Datta, R., Dute, R., Urry, D. W. and Daniell, H. (1996) *Plant Cell Reports* 15: 381-385.

Zhang, X., Guda, C., Datta, R., Dute, R., Urry, D. W., Danell, H. (1995) *Biotechnology Letters* 17: 1279-1284.

Zhang, X., Urry, D. W. and Daniell, H. (1996) *Plant Cell Rep.* 16: 174-179.

*Current Protocols in Molecular Biology*, Asubel et al., eds., John Wiley and Sons, Inc. (1997) Vol. I, II and III.

*Herbicide Resistance Crops, Agricultural, Environmental, Economic, Regulatory and Technical Aspects*, Duke, S. O., edt., CRC Press, Inc. (1996).

*Herbicide Resistance in Plants, Biology and Biochemistry*, Powles, S. B., and Holtum, J. A. M., eds., CRC, Press, Inc. (1994.

---

The invention claimed is:

1. A stably transformed herbicide resistant target plant species, or the progeny thereof, which comprises a chloroplast stably transformed with a universal integration and expression vector competent for stable transformation of the chloroplast of different plant species, which vector comprises an expression cassette which encodes a heterologous protein of interest expressed by a heterologous DNA sequence in the chloroplast genome of the target plant species, which heterologous DNA confers tolerance to said herbicide, and flanking each side of the expression cassette, flanking DNA sequences derived from a transcriptionally active spacer region of a chloroplast genome, whereby stable integration of the heterologous DNA encoding the heterologous protein into a transcriptionally active spacer region of the chloroplast genome of the target plant was facilitated through homologous recombination of the flanking sequences with the homologous sequences in the target chloroplast genome.

2. The herbicide resistant target plant of claim 1 in which the protein of interest is a mutant form of an enzyme which has decreased affinity for the herbicide than does the naturally occurring enzyme.

3. The herbicide resistant target plant of claim 1 wherein the herbicide is glyphosate.

4. The herbicide resistant target plant of claim 3 wherein the enzyme is EPSP synthase.

5. The herbicide resistant target plant of claim 2 wherein the herbicide is selected from at least one of the following types: PSI, PSII, APP, auxin analog, mitotic, tertiary amino methyl phosphoric acids type and ALS inhibiting types.

6. The herbicide resistant target plant of claim 5 wherein the herbicide is the PSI type selected from paraquat and diquat.

7. The herbicide resistant target plant of claim 5 wherein the herbicide is selected from atrazine, dinoseb, lenacil and metribuzine.

8. The herbicide resistant target plant of claim 5 wherein the herbicide is of the APP type selected from cyclohexanedione, haloxyfop, clethodim and phenoxaprop, and the lower alkyl-substituted compound thereof.

9. The herbicide resistant target plant of claim 5 wherein the herbicide is an auxin analog selected from MCPA and 2,4-D.

10. The herbicide resistant target plant of claim 5 wherein the herbicide is a mitotic type herbicide, which is dinitroahiline.

11. The herbicide resistant target plant of claim 2 wherein the herbicide is a tertiary amino methyl phosphoric acid type, which is glyphosate.

12. The herbicide resistant target plant of claim 5 wherein the herbicide is an ALS inhibiting type selected from sulfonylureas and imidazolines.

13. The herbicide resistant target plant of claim 5 wherein the herbicide is selected from bromoxynil, methyl sulfuron, chlorsulfuron, phosphinothricin and imazapyr.

14. The herbicide resistant target plant of claim 5 which is maize, rice, grass, rye, barley, oat, wheat, soybean, peanut, grape, potato, sweet potato, pea, canola, tobacco, tomato or cotton.

15. The herbicide resistant target plant of claim 14 which is a homoplasmic plant.

16. A process for conferring herbicide resistance to a target plant species, which process comprises introducing into a plant cell of the target plant an integration and expression vector which vector comprises an expression cassette that comprises, operably joined, a heterologous DNA sequence coding for a protein of interest which confers resistance to a herbicide and control sequences positioned upstream from the 5' and downstream from the 3' ends of the coding sequence to provide expression of the coding sequence in the chloroplast of the target plant, a heterologous nucleotide sequence that confers a selectable phenotype other than tolerance to said herbicide, and flanking each side of the expression cassette, flanking sequences which are derived from a transcriptionally active spacer region of which are homologous to a transcriptionally active spacer sequence of the target chloroplast genome of the target plant, whereby stable integration of the heterologous coding sequence into a transcriptionally active spacer region of the chloroplast genome of the target plant is facilitated through homologous recombination of the flanking sequences with the homologous sequences in the target chloroplast genome; and growing the transformed plant.

17. The process of claim 16 wherein the DNA sequence codes for a mutant form of an enzyme which has decreased affinity for the herbicide than does the naturally occurring enzyme.

18. The process of claim 17 wherein the enzyme is EPSP synthase and the herbicide is glyphosate.

19. The process of claim 18 wherein the DNA sequence is the EPSP synthase gene which is a mutant EPSP synthase gene.

20. The process of claim 16 which comprises selecting the viable, transformed target plants on a medium which is lethal to non-transformed plants.

21. The process of claim 20 wherein the viable transformed target plants are homoplasmic plants.

22. The process of claim 20 wherein the viable transformed target plants are heteroplasmic plants.

23. The process of claim 16 wherein the herbicide resistant target plant is tobacco, and the nucleotide sequence confers a selectable phenotype which is lethal to tobacco or confers a visual trait that permits selection of the transformed tobacco plants from the non-transformed plants.

24. The process of claim 23 wherein the lethal selectable phenotype is resistance to hygromycin to which tobacco is not naturally resistant.

25. The process of claim 23 wherein the visual trait is the expression of a color.

26. The process of claim 16 for stably transforming the phenotype of a target plant species, whereby the grown transformed plant expresses the selectable phenotype and another trait in addition to the expression of that phenotype.

27. The process of claim 26 wherein the selected phenotype is conferred by expression of the hygromycin β-phosphotransferase gene and the additional trait that is conferred is resistance to the herbicide glyphosate.

28. A process of determining chloroplast transformation and expression of a target trait on the basis of a target plant species' acquisition of resistance to a selected herbicide due to the transformation of the plant species, which process comprises introducing into the plant a universal integration, and expression vector competent for stably transforming the chloroplast of different plant species, which vector comprises an expression cassette which comprises, operably joined, a heterologous DNA sequence coding for a protein conferring the desired target trait and control sequences positioned upstream from the 5' and downstream from the 3' ends of the coding sequence to provide expression of the coding sequence in the chloroplast of a target plant, a heterologous nucleotide sequence conferring herbicide resistance and flanking each side of the expression cassette, flanking DNA sequences which comprise each one a portion of the intergenic spacer 2 region between the tRNA$^{Ile}$ and the tRNA$^{Ala}$ genes of the chloroplast genome, which are homologous to a spacer sequence of the target chloroplast genome, which spacer sequence is conserved in the chloroplast genome of different plant species, whereby stable integration of the heterologous coding sequence into the chloroplast genome of the target plant is facilitated through homologous recombination of the flanking sequences with the homologous sequences in the target chloroplast genome; and exposing the plants into which the vector has been introduced to a lethal concentration of the herbicide and selecting the plants which do not die from exposure thereto, thereby having selected the transformed plants which express the desired target trait.

29. The process of claim 28 wherein the selected herbicide is selected from at least one of the following types: PSI, PSII, APP, auxin analog, mitotic, tertiary amino methyl phosphoric acids and ALS inhibiting types.

* * * * *